US009278146B2

(12) United States Patent
Saji et al.

(10) Patent No.: US 9,278,146 B2
(45) Date of Patent: Mar. 8, 2016

(54) PEPTIDE DERIVATIVE AND USE OF THE SAME

(75) Inventors: Hideo Saji, Kyoto (JP); Nobuya Inagaki, Kyoto (JP); Hiroyuki Kimura, Kyoto (JP); Kentaro Toyoda, Kyoto (JP); Konomu Hirao, Kyoto (JP); Hirokazu Matsuda, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 244 days.

(21) Appl. No.: 13/269,345

(22) Filed: Oct. 7, 2011

(65) Prior Publication Data

US 2012/0087863 A1   Apr. 12, 2012

Related U.S. Application Data

(60) Provisional application No. 61/391,374, filed on Oct. 8, 2010, provisional application No. 61/496,831, filed on Jun. 14, 2011.

(51) Int. Cl.
| | | |
|---|---|---|
| *A61K 51/00* | (2006.01) | |
| *A61M 36/14* | (2006.01) | |
| *A61K 51/08* | (2006.01) | |
| *C07K 14/575* | (2006.01) | |

(52) U.S. Cl.
CPC ............... *A61K 51/08* (2013.01); *A61K 51/088* (2013.01); *C07K 14/57563* (2013.01)

(58) Field of Classification Search
CPC ..... A61K 51/088; A61K 51/08; A61K 51/04; A61K 51/0497; A61K 51/00; A61K 51/02; A61K 51/041; A61K 51/06; A61K 2121/00; A61K 2123/00; A61K 38/00; A61K 38/03; A61K 38/10; A61K 38/12; A61K 38/16; A61K 49/00; A61K 49/001; A61K 49/04; A61K 49/06; A61K 49/08; A61K 49/085; A61K 49/10; A61K 49/14; A61K 49/22; C07K 14/00; C07K 13/00; C07K 13/005; C07K 14/57563
USPC .......... 424/1.11, 1.65, 1.69, 9.1, 9.2, 9.3, 9.4, 424/9.5, 9.6; 514/1, 1.1, 21.3; 530/300, 530/317, 324
See application file for complete search history.

(56) References Cited

U.S. PATENT DOCUMENTS

| | | | |
|---|---|---|---|
| 8,642,008 B2 * | 2/2014 | Inagaki et al. ............... | 424/1.85 |
| 2009/0180953 A1 | 7/2009 | Gotthardt et al. | |
| 2011/0171129 A1 | 7/2011 | Inagaki et al. | |

FOREIGN PATENT DOCUMENTS

| | | | |
|---|---|---|---|
| EP | 1867634 A1 | 12/2007 | |
| EP | 2418216 A1 | 2/2012 | |
| EP | 2484386 A1 | 8/2012 | |
| JP | 09-292466 A | 11/1997 | |
| JP | 2008-511557 A | 4/2008 | |
| WO | 2004/035744 A2 | 4/2004 | |
| WO | 2006/107106 A1 | 10/2006 | |
| WO | 2010/032509 A1 | 3/2010 | |
| WO | 2010/107256 A2 | 9/2010 | |

OTHER PUBLICATIONS

Goke et al, The Journal of Biological Chemistry, 1993, vol. 268, No. 26, pp. 19650-19655.*
Eng et al, The Journal of Biological Chemistry, 1992, vol. 267, No. 11, pp. 7402-7405.*
Office Action issued in corresponding Japanese Patent Application No. 2011-554317 dated Sep. 3, 2013.
Al-Sabah et al., "The positive charge at Lys-288 of the glucagon-like peptide-1 (GLP-1) receptor is important for binding the N-terminus of peptide agonists," FEBS Letters 553: 342-346 (2003).
Arkray, Inc., "Leading research relating to a molecular imaging device for assisting treatment of malignant tumors, etc./development of ultra-early diagnosis of diabetes by noninvasive in-vivo pancreatic islets imaging," Interim report of Heisei 19 (2007) fiscal year, out of Heisei 19 to 20 (2007-2008) Fiscal years (Partial (pp. 1, 5) translation provided.
Behe et al., "Are radiolabeled GLP-1 receptor antagonists useful for scintigraphy?", 2009 SNM Annual Meeting, Abstract, Oral Presentations, No. 327 (2009).
Blakely et al., "Formulation and characterization of radio-opaque conjugated in situ gelling materials," Journal of Biomedical Materials Research Part B: Applied Biomaterials, 93: 9-17 (2010).
Brom et al., "68Ga-labelled exendin-3, a new agent for the detection of insulinomas with PET," Eur J Nucl Med Mol Imaging 37: 1345-1355 (2010).
Cheng, "[18F]FB-NH-mini-PEG-E{E[c(RGDyK)]2}2.", Molecular Imaging and Contrast Agent Database (MICAD) [Internet]., NCBI, Feb. 20, 2008, Bookshelf ID: NBK23235, PMID: 20641437.
Christ et al., "Glucagon-Like Peptide-1 Receptor Imaging for Localization of Insulinomas," J. Clin. Endocrinol Metab. 94: 4398-4405 (2009).

(Continued)

*Primary Examiner* — D L Jones
(74) *Attorney, Agent, or Firm* — Morgan, Lewis & Bockius LLP

(57) ABSTRACT

A new peptide derivative is provided. The peptide derivative is represented by the following general formula (I), (I)

where polypeptide ExP is polypeptide that contains completely or partially the amino acid sequence of exendin-4, and a -L-Z group represents a group represented by the following formula (II) that is bonded to an amino acid side chain of or the α-amino group at the N-terminus of the polypeptide ExP, (II)

36 Claims, 9 Drawing Sheets

(56) References Cited

OTHER PUBLICATIONS

Goke et al., "Exendin-4 is a High Potency Agonist and Truncated Exendin-(9-39)-amide an Antagonist at the Glucagon-like Peptide 1-(7-36)-amide Receptor of Insulin-secreting β-Cells," J. Biol. Chem. 268: 19650-19655 (1993).

Gotthardt et al., "A new technique for in vivo imaging of specific GLP-1 binding sites: First results in small rodents," Regulatory Peptides 137: 162-167 (2006).

Gotthardt et al., "Use of the incretin hormone glucagon-like peptide-1 (GLP-1) for the detection of insulinomas: initial experimental results," European Journal of Nuclear Medicine 29: 597-606 (2002).

Green et al., "Chronic treatment with exendin(9-39)amide indicates a minor role for endogenous glucagon-like peptide-1 in metabolic abnormalities of obesity-related diabetes in ob/ob mice," J. Endocrinol., 185: 307-317 (2005).

Hirao, "Leading research relating to a molecular imaging device for assisting treatment of malignant tumors, etc., / devlopment of ultra-early diagnosis of diabetes by noninvasive in-vivo pancreatic islet imaging," Interim report of Heisei 20 (2008) Fiscal Year, out of Heisei 19 to 20 (2007-2008) years (Partial (pp. 1, 2) translation provided.

Inagaki "Research on development of method for ultra-early diagnosis of diabetes by noninvasive in-vivo pancreatic islet imaging," Heisei 19 (2007) Fiscal Year Overview Research Report, Research Project for Medical Equipment Development Promotion, Grants-in-Aid for Scientific Research from Ministry of Health, Labor and Welfare (Apr. 20, 2008) (Partial (pp. 1-7, 10-15, 24, 25) translation provided.

Inagaki, "Research on development of method for ultra-early diagnosis of diabetes by noninvasive in-vivo pancreatic islet imaging," Heisei 20 (2008) Fiscal Year Overview Research Report, Research Project for Medical Equipment Development Promotion, Grants-in-Aid for Scientific Research from Ministry of Health, Labor and Welfare (Apr. 21, 2009) (Partial (pp. 1-7, 10-17, 23, 24) translation provided.

Inagaki, "Development of method for ultra-early diagnosis of diabetes by noninvasive in-vivo pancreatic islet imaging," Research of New Medical Devices 13 (21): 72-73 (Mar. 25, 2008) (Partial (pp. 72, 73) translation provided.

Kimura et al., "Development of in vivo imaging agents targeting glucagon-like peptide-1 receptor (GLP-1R) in pancreatic islets," 2009 SNM Annual Meeting, Abstract, Oral Presentations, No. 326 (2009).

Leung, "3-(4-Hydroxy-3-[125I]iodophenyl)propionate-exendin(9-39)," Molecular Imaging and Contrast Agent Database (MICAD)[Internet], NCBI, Bookshelf, Bookshelf ID: NBK44BIB, PMID: 2064-2016 (Apr. 6, 2010).

Leung, "111In-Diethylenetriaminepentaacetic acid-aminohexanoic acid-Lys40-exendin-4," MICAD Molecular Imaging & Contrast Agent Database, 2007.

Liu, et al., "(68)Ga-labeled cyclic RGD dimers with Gly3 and PEG4 linkers: promising agents for tumor integrin αvβ3 PET imaging," Eur J of Nucl Med Mol Imaging, 36: 947-957 (2009).

Melendez-Alafort et al., "Detection of sites of inflection in mice using 99mTc-labeled PN(2)S-PEG conjugated to UBI and 99mTc-UBI: a comparative biodistribution study," Nuclear Medicine and Biology, 36: 57-64 (2009).

Mukai et al., "Non-invasive imaging of pancreatic islets targeting glucagon-like peptide-1-receptors", 44th EASD Annual Meeting (Rome), abstract, Presentation No. 359 (2008).

Mukai et al., "GLP-1 receptor antagonist as a potential probe for pancreatic β-cell imaging," Biochemical and Biophysical Research Communications, 389: 523-526 (2009).

Neidigh et al., "Exendin-4 and Glucagon-like peptide-1: NMR Structural Comparisons in the Solution and Micelle-Associated States," Biochemistry 40: 13188-13200 (2001).

Ritzel et al., "A synthetic glucagon-like peptide-1 analog with improved plasma stability," Journal of Endocrinology 159: 93-102 (1998).

Schirra et al., "Exendin(9-39)amide Is an Antagonist of Glucagon-like Peptide-1(7-36)amide in Humans," J. Clin. Invest. 101: 1421-1430 (1998).

Vaidyanathan et al., "Radioiodination of Proteins Using N-Succinimidyl 4-Hydroxy-3-iodobenzoate," Bioconjug. Chem., 4: 78-84 (1993).

Vaidyanathan et al., "Protein Radiohalogenation: Observations on the Design of N-Succinimidyl Ester Acylation Agents," Bioconjug. Chem., 1: 269-273 (1990).

Wicki et al., "[Lys40(Ahx-DTPA-111In)NH2]-Exendin-4 Is a Highly Efficient Radiotherapeutic for Glucagon-Like Peptide-1 Receptor-Targeted Therapy for Insulinoma," Clin. Cancer Research, 13: 3696-3705 (2007).

Wild et al., "Exendin-4-based radiopharmaceuticals for glucagonlike peptide-1 receptor PET/CT and SPECT/CT," Journal of Nuclear Medicine, 51: 1059-1067 (2010).

Wild et al., "[Lys40(Ahx-DTPA-111In)NH2]Exendin-4, a Very Promising Ligand for Glucagon-like Peptide-1 (GLP-1) Receptor Targeting," J. Nucl. Med. 47: 2025-2033 (2006).

Extended European Search Report issued in counterpart European Patent Application No. 11830776.8 dated Mar. 14, 2014.

Office Action issued in counterpart European Patent Application No. 11830776.8 dated Jul. 10, 2015.

* cited by examiner

SEQUENCE LISTING

```
<160> NUMBER OF SEQ ID NOS: 39

<210> SEQ ID NO 1
<211> LENGTH: 39
<212> TYPE: PRT
<213> ORGANISM: Heloderma suspectum

<400> SEQUENCE: 1
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 39
<212> TYPE: PRT
<213> ORGANISM: Artificial
<220> FEATURE:
<223> OTHER INFORMATION: A peptide derivate

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 3
<211> LENGTH: 40
<212> TYPE: PRT
<213> ORGANISM: Artificial Sequence
<220> FEATURE:
<223> OTHER INFORMATION: A peptide derivate

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35                  40

<210> SEQ ID NO 4
<211> LENGTH: 31
<212> TYPE: PRT
<213> ORGANISM: Artificial Sequence
<220> FEATURE:
<223> OTHER INFORMATION: A peptide derivate

<400> SEQUENCE: 4

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: A pepitde derivate

<400> SEQUENCE: 5

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser Lys
            20                  25                  30

```
<210> SEQ ID NO 6
<211> LENGTH: 31
<212> TYPE: PRT
<213> ORGANISM: Artificial Sequence
<220> FEATURE:
<223> OTHER INFORMATION: A peptide derivate of formula (6)
<220> FEATURE:
<221> NAME/KEY: MOD_RES
<222> LOCATION: (4)..(4)
<223> OTHER INFORMATION: An amino group of a side chain is bound to
      [125I]IB-PEG3.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 6

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: A protected peptide resin A
<220> FEATURE:
<221> NAME/KEY: MOD_RES
<222> LOCATION: (1)..(1)
<223> OTHER INFORMATION: An alpha-amino group of an N-terminus is
      protected by a Fmoc.  A functional group of a side chain is
      protected by a OBu.
<220> FEATURE:
<221> NAME/KEY: MOD_RES
<222> LOCATION: (3)..(3)
<223> OTHER INFORMATION: A functional group of a side chain is protected
      by a OBu.
<220> FEATURE:
<221> NAME/KEY: MOD_RES
<222> LOCATION: (4)..(4)
<223> OTHER INFORMATION: An amino group of a side chain is bound to
      Boc-PEG3.
<220> FEATURE:
<221> NAME/KEY: MOD_RES
<222> LOCATION: (5)..(5)
<223> OTHER INFORMATION: A functional group of a side chain is protected
      by a Trt.
<220> FEATURE:
<221> NAME/KEY: MOD_RES
<222> LOCATION: (7)..(9)
<223> OTHER INFORMATION: A functional group of a side chain is protected
      by a OBu.
<220> FEATURE:
<221> NAME/KEY: MOD_RES
<222> LOCATION: (12)..(12)
<223> OTHER INFORMATION: A functional group of a side chain is protected
      by a Pdf.
<220> FEATURE:
<221> NAME/KEY: MOD_RES
<222> LOCATION: (16)..(16)
<223> OTHER INFORMATION: A functional group of a side chain is protected
      by a OBu.
<220> FEATURE:
<221> NAME/KEY: MOD_RES
<222> LOCATION: (17)..(17)
<223> OTHER INFORMATION: A functional group of a side chain is protected
      by a Boc.
<220> FEATURE:
<221> NAME/KEY: MOD_RES
<222> LOCATION: (19)..(19)
<223> OTHER INFORMATION: An amino group of a side chain is protected by
      a Fmoc
```

```
<220> FEATURE:
<221> NAME/KEY: MOD_RES
<222> LOCATION: (20)..(20)
<223> OTHER INFORMATION: A functional group of a side chain is protected
      by a Trt.
<220> FEATURE:
<221> NAME/KEY: MOD_RES
<222> LOCATION: (24)..(25)
<223> OTHER INFORMATION: A functional group of a side chain is protected
      by a OBu.
<220> FEATURE:
<221> NAME/KEY: MOD_RES
<222> LOCATION: (31)..(31)
<223> OTHER INFORMATION: A functional group of a side chain is protected
      by a OBu. A carboxyl group of a C-terminus is bound to Rink Amide
      MBHA.

<400> SEQUENCE: 7

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 8
<211> LENGTH: 27
<212> TYPE: PRT
<213> ORGANISM: Artificial Sequence
<220> FEATURE:
<223> OTHER INFORMATION: A protected peptide resin A1
<220> FEATURE:
<221> NAME/KEY: MOD_RES
<222> LOCATION: (1)..(1)
<223> OTHER INFORMATION: An alpha-amino group of an N-terminus is
      protected by a Fmoc. A functional group of a side chain is
      protected by a Trt.
<220> FEATURE:
<221> NAME/KEY: MOD_RES
<222> LOCATION: (3)..(5)
<223> OTHER INFORMATION: A functional group of a side chain is protected
      by a OBu.
<220> FEATURE:
<221> NAME/KEY: MOD_RES
<222> LOCATION: (8)..(8)
<223> OTHER INFORMATION: A functional group of a side chain is protected
      by a Pdf.
<220> FEATURE:
<221> NAME/KEY: MOD_RES
<222> LOCATION: (13)..(13)
<223> OTHER INFORMATION: A functional group of a side chain is protected
      by a OBu.
<220> FEATURE:
<221> NAME/KEY: MOD_RES
<222> LOCATION: (14)..(14)
<223> OTHER INFORMATION: A functional group of a side chain is protected
      by a Boc.
<220> FEATURE:
<221> NAME/KEY: MOD_RES
<222> LOCATION: (16)..(16)
<223> OTHER INFORMATION: An amino group of a side chain is protected by
      a Mmt.
<220> FEATURE:
<221> NAME/KEY: MOD_RES
<222> LOCATION: (17)..(17)
<223> OTHER INFORMATION: A functional group of a side chain is protected
      by a Trt.
<220> FEATURE:
<221> NAME/KEY: MOD_RES
<222> LOCATION: (20)..(21)
<223> OTHER INFORMATION: A functional group of a side chain is protected
      by a OBu.
<220> FEATURE:
<221> NAME/KEY: MOD_RES
<222> LOCATION: (27)..(27)
<223> OTHER INFORMATION: A functional group of a side chain is protected
      by a OBu. A carboxyl group of a C-terminus is bound to Rink Amide
      MBHA
```

-continued

```
<400> SEQUENCE: 8

Gln Met Glu Glu Glu Ala Val Arg Leu Phe Ile Glu Trp Leu Lys Asn
1               5                   10                  15

Gly Gly Pro Ser Ser Gly Ala Pro Pro Pro Ser
            20                  25

<210> SEQ ID NO 9
<211> LENGTH: 31
<212> TYPE: PRT
<213> ORGANISM: Artificial Sequence
<220> FEATURE:
<223> OTHER INFORMATION: A protected peptide resin A2
<220> FEATURE:
<221> NAME/KEY: MOD_RES
<222> LOCATION: (1)..(1)
<223> OTHER INFORMATION: An alpha-amino group of an N-terminus is
      protected by a Fmoc.  A functional group of a side chain is
      protected by a OBu.
<220> FEATURE:
<221> NAME/KEY: MOD_RES
<222> LOCATION: (3)..(3)
<223> OTHER INFORMATION: A functional group of a side chain is protected
      by a OBu.
<220> FEATURE:
<221> NAME/KEY: MOD_RES
<222> LOCATION: (4)..(4)
<223> OTHER INFORMATION: An amino group of a side chain is bound to
      Boc-PEG3.
<220> FEATURE:
<221> NAME/KEY: MOD_RES
<222> LOCATION: (5)..(5)
<223> OTHER INFORMATION: A functional group of a side chain is protected
      by a Trt.
<220> FEATURE:
<221> NAME/KEY: MOD_RES
<222> LOCATION: (7)..(9)
<223> OTHER INFORMATION: A functional group of a side chain is protected
      by a OBu.
<220> FEATURE:
<221> NAME/KEY: MOD_RES
<222> LOCATION: (12)..(12)
<223> OTHER INFORMATION: A functional group of a side chain is protected
      by a Pdf.
<220> FEATURE:
<221> NAME/KEY: MOD_RES
<222> LOCATION: (16)..(16)
<223> OTHER INFORMATION: A functional group of a side chain is protected
      by a OBu.
<220> FEATURE:
<221> NAME/KEY: MOD_RES
<222> LOCATION: (17)..(17)
<223> OTHER INFORMATION: A functional group of a side chain is protected
      by a Boc.
<220> FEATURE:
<221> NAME/KEY: MOD_RES
<222> LOCATION: (19)..(19)
<223> OTHER INFORMATION: An amino group of a side chain is protected by
      a Mmt.
<220> FEATURE:
<221> NAME/KEY: MOD_RES
<222> LOCATION: (20)..(20)
<223> OTHER INFORMATION: A functional group of a side chain is protected
      by a Trt.
<220> FEATURE:
<221> NAME/KEY: MOD_RES
<222> LOCATION: (24)..(25)
<223> OTHER INFORMATION: A functional group of a side chain is protected
      by a OBu.
<220> FEATURE:
<221> NAME/KEY: MOD_RES
<222> LOCATION: (31)..(31)
<223> OTHER INFORMATION: A functional group of a side chain is protected
      by a OBu.  A carboxyl group of a C-terminus is bound to Rink Amide
      MBHA.
```

```
<400> SEQUENCE: 9

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: A peptide derivate of formula (10)
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (4)..(4)
<223> OTHER INFORMATION: An amino group of a side chain is bound to
      PEG3.
<220> FEATURE:
<221> NAME/KEY: MOD_RES
<222> LOCATION: (19)..(19)
<223> OTHER INFORMATION: An amino group of a side chain is bound to
      Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 10

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: A peptide derivate of reference production
      example 1
<220> FEATURE:
<221> NAME/KEY: MOD_RES
<222> LOCATION: (4)..(4)
<223> OTHER INFORMATION: An amino group of a side chain is labeled by
      [125I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 11

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: A precursor of a peptide derivate of reference
      production example 1
<220> FEATURE:
<221> NAME/KEY: MOD_RES
```

```
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 12

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: A peptide derivate of formula (13)
<220> FEATURE:
<221> NAME/KEY: MOD_RES
<222> LOCATION: (32)..(32)
<223> OTHER INFORMATION: An amino group of a side chain is bound to
      [125I]IB-PEG3.  A carboxyl group of a C-terminus is amidated.

<400> SEQUENCE: 13

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: A protected peptide resin B
<220> FEATURE:
<221> NAME/KEY: MOD_RES
<222> LOCATION: (1)..(1)
<223> OTHER INFORMATION: An alpha-amino group of an N-terminus is
      protected by a Fmoc.  A functional group of a side chain is
      protected by a OBu.
<220> FEATURE:
<221> NAME/KEY: MOD_RES
<222> LOCATION: (3)..(3)
<223> OTHER INFORMATION: A functional group of a side chain is protected
      by a OBu.
<220> FEATURE:
<221> NAME/KEY: MOD_RES
<222> LOCATION: (4)..(4)
<223> OTHER INFORMATION: An amino group of a side chain is protected by
      a Fmoc.
<220> FEATURE:
<221> NAME/KEY: MOD_RES
<222> LOCATION: (5)..(5)
<223> OTHER INFORMATION: A functional group of a side chain is protected
      by a Trt.
<220> FEATURE:
<221> NAME/KEY: MOD_RES
<222> LOCATION: (7)..(9)
<223> OTHER INFORMATION: A functional group of a side chain is protected
      by a OBu.
<220> FEATURE:
<221> NAME/KEY: MOD_RES
<222> LOCATION: (12)..(12)
<223> OTHER INFORMATION: A functional group of a side chain is protected
```

```
      by a Pdf.
<220> FEATURE:
<221> NAME/KEY: MOD_RES
<222> LOCATION: (16)..(16)
<223> OTHER INFORMATION: A functional group of a side chain is protected
      by a OBu.
<220> FEATURE:
<221> NAME/KEY: MOD_RES
<222> LOCATION: (17)..(17)
<223> OTHER INFORMATION: A functional group of a side chain is protected
      by a Boc.
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (20)..(20)
<223> OTHER INFORMATION: A functional group of a side chain is protected
      by a Trt.
<220> FEATURE:
<221> NAME/KEY: MOD_RES
<222> LOCATION: (24)..(25)
<223> OTHER INFORMATION: A functional group of a side chain is protected
      by a OBu.
<220> FEATURE:
<221> NAME/KEY: MOD_RES
<222> LOCATION: (32)..(32)
<223> OTHER INFORMATION: An amino group of a side chain is bound to
      Boc-PEG3. A carboxyl group of a C-terminus is bound to Rink Amide
      MBHA.

<400> SEQUENCE: 14

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: A peptide derivate of formula (15)
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (4)..(4)
<223> OTHER INFORMATION: An amino group of a side chain is bound to a
      Fmoc.
<220> FEATURE:
<221> NAME/KEY: MOD_RES
<222> LOCATION: (19)..(19)
<223> OTHER INFORMATION: An amino group of a side chain is bound to a
      Fmoc.
<220> FEATURE:
<221> NAME/KEY: MOD_RES
<222> LOCATION: (32)..(32)
<223> OTHER INFORMATION: An amino group of a side chain is bound to
      PEG3. A carboxyl group of a C-terminus is amidated.

<400> SEQUENCE: 15

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 16
```

```
<211> LENGTH: 32
<212> TYPE: PRT
<213> ORGANISM: Artificial Sequence
<220> FEATURE:
<223> OTHER INFORMATION: A peptide derivate of reference production
      example 2
<220> FEATURE:
<221> NAME/KEY: MOD_RES
<222> LOCATION: (32)..(32)
<223> OTHER INFORMATION: An amino group of a side chain is labeled by
      [125I]3-iodobenzoyl.  A carboxyl group of a C-terminus is
      amidated.

<400> SEQUENCE: 16

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: A precursor of a peptide derivate of reference
      production example 2
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (4)..(4)
<223> OTHER INFORMATION: An amino group of a side chain is protected by
      a Fmoc.
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (32)..(32)
<223> OTHER INFORMATION: A carboxyl group of a C-terminus is amidated.

<400> SEQUENCE: 17

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: A peptide derivate of formula (18)
<220> FEATURE:
<221> NAME/KEY: MOD_RES
<222> LOCATION: (4)..(4)
<223> OTHER INFORMATION: An amino group of a side chain is bound to
      [123I]IB-PEG3.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 18

Asp Leu Ser Lys Gln Met Glu Glu Glu Ala Val Arg Leu Phe Ile Glu
1               5                   10                  15
```

```
Trp Leu Lys Asn Gly Gly Pro Ser Ser Gly Ala Pro Pro Pro Ser
            20                  25                  30
```

<210> SEQ ID NO 19
<211> LENGTH: 32
<212> TYPE: PRT
<213> ORGANISM: Artificial Sequence
<220> FEATURE:
<223> OTHER INFORMATION: A peptide derivate of formula (19)
<220> FEATURE:
<221> NAME/KEY: MOD_RES
<222> LOCATION: (32)..(32)
<223> OTHER INFORMATION: An amino group of a side chain is bound to
      [123I]IB-PEG3. A carboxyl group of a C-terminus is amidated.

<400> SEQUENCE: 19

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30
```

<210> SEQ ID NO 20
<211> LENGTH: 31
<212> TYPE: PRT
<213> ORGANISM: Heloderma suspectum
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 20

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 21
<211> LENGTH: 39
<212> TYPE: PRT
<213> ORGANISM: Artificial Sequence
<220> FEATURE:
<223> OTHER INFORMATION: A peptide derivate of formula (21)
<220> FEATURE:
<221> NAME/KEY: MOD_RES
<222> LOCATION: (12)..(12)
<223> OTHER INFORMATION: An amino group of a side chain is bound to
      [18F]FB-PEG3.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 21

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 22
<211> LENGTH: 39
<212> TYPE: PRT
<213> ORGANISM: Artificial Sequence
<220> FEATURE:
<223> OTHER INFORMATION: A peptide derivate of formula (22)
<220> FEATURE:
<221> NAME/KEY: MOD_RES

```
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (12)..(12)
<223> OTHER INFORMATION: An amino group of a side chain is bound to
      PEG3.
<220> FEATURE:
<221> NAME/KEY: MOD_RES
<222> LOCATION: (27)..(27)
<223> OTHER INFORMATION: An amino group of a side chain is bound to
      Fmoc.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: A precursor of peptide derivate of reference
      production example 3
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (27)..(27)
<223> OTHER INFORMATION: An amino group of a side chain is bound to
      Fmoc.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: A peptide derivate of reference production
      example 3
<220> FEATURE:
<221> NAME/KEY: MOD_RES
<222> LOCATION: (12)..(12)
<223> OTHER INFORMATION: An amino group of a side chain is bound to
      [18F]FB.
<220> FEATURE:
<221> NAME/KEY: MOD_RES
<222> LOCATION: (39)..(39)
```

<223> OTHER INFORMATION: A carboxyl group of a C-terminus is amidated.

<400> SEQUENCE: 24

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: A peptide derivate of formula (25)
<220> FEATURE:
<221> NAME/KEY: MOD_RES
<222> LOCATION: (12)..(12)
<223> OTHER INFORMATION: An amino group of a side chain is bound to
      [125I]IB-PEG3.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 25

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: A peptide derivate of reference production
      example 4
<220> FEATURE:
<221> NAME/KEY: MOD_RES
<222> LOCATION: (12)..(12)
<223> OTHER INFORMATION: An amino group of a side chain is bound to
      [125I]IB.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 26

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 27
<211> LENGTH: 40
<212> TYPE: PRT
<213> ORGANISM: Artificial Sequence
<220> FEATURE:
<223> OTHER INFORMATION: A peptide derivate of formula (27)
<220> FEATURE:
<221> NAME/KEY: MOD_RES
<222> LOCATION: (40)..(40)
<223> OTHER INFORMATION: An amino group of a side chain is bound to
      [125I]IB-PEG3. A carboxyl group of a C-terminus is amidated.

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 28
<211> LENGTH: 40
<212> TYPE: PRT
<213> ORGANISM: Artificial Sequence
<220> FEATURE:
<223> OTHER INFORMATION: A peptide derivate of formula (28)
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (12)..(12)
<223> OTHER INFORMATION: An amino group of a side chain is bound to a
      Fmoc.
<220> FEATURE:
<221> NAME/KEY: MOD_RES
<222> LOCATION: (27)..(27)
<223> OTHER INFORMATION: An amino group of a side chain is bound to a
      Fmoc.
<220> FEATURE:
<221> NAME/KEY: MOD_RES
<222> LOCATION: (40)..(40)
<223> OTHER INFORMATION: An amino group of a side chain is bound to
      PEG3. A carboxyl group of a C-terminus is amidated.

<400> SEQUENCE: 28

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 29
<211> LENGTH: 40
<212> TYPE: PRT
<213> ORGANISM: Artificial Sequence
<220> FEATURE:
<223> OTHER INFORMATION: A peptide derivate of formula (29)
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (12)..(12)
<223> OTHER INFORMATION: An amino group of a side chain is bound to a
      Fmoc.
<220> FEATURE:
<221> NAME/KEY: MOD_RES
<222> LOCATION: (27)..(27)
<223> OTHER INFORMATION: An amino group of a side chain is bound to a
      Fmoc.
<220> FEATURE:
<221> NAME/KEY: MOD_RES
<222> LOCATION: (40)..(40)

<223> OTHER INFORMATION: A carboxyl group of a C-terminus is amidated.

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 30
<211> LENGTH: 40
<212> TYPE: PRT
<213> ORGANISM: Artificial Sequence
<220> FEATURE:
<223> OTHER INFORMATION: A peptide derivate of formula (30)
<220> FEATURE:
<221> NAME/KEY: MOD_RES
<222> LOCATION: (40)..(40)
<223> OTHER INFORMATION: An amino group of a side chain is bound to
      [125I]IB. A carboxyl group of a C-terminus is amidated.

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 31
<211> LENGTH: 31
<212> TYPE: PRT
<213> ORGANISM: Artificial Sequence
<220> FEATURE:
<223> OTHER INFORMATION: A peptide derivate of formula (31)
<220> FEATURE:
<221> NAME/KEY: MOD_RES
<222> LOCATION: (4)..(4)
<223> OTHER INFORMATION: An amino group of a side chain is bound to
      IB-PEG3.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 31

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: A peptide derivate of formula (32)
<220> FEATURE:
<221> NAME/KEY: MOD_RES
<222> LOCATION: (32)..(32)
<223> OTHER INFORMATION: An amino group of a side chain is bound to
      IB-PEG3. A carboxyl group of a C-terminus is amidated.

<400> SEQUENCE: 32

Asp Leu Ser Lys Gln Met Glu Glu Glu Ala Val Arg Leu Phe Ile Glu
1               5                   10                  15

```
Trp Leu Lys Asn Gly Gly Pro Ser Ser Gly Ala Pro Pro Ser Lys
            20                  25                  30
```

```
<210> SEQ ID NO 33
<211> LENGTH: 39
<212> TYPE: PRT
<213> ORGANISM: Artificial Sequence
<220> FEATURE:
<223> OTHER INFORMATION: A peptide derivate of formula (33)
<220> FEATURE:
<221> NAME/KEY: MOD_RES
<222> LOCATION: (12)..(12)
<223> OTHER INFORMATION: An amino group of a side chain is bound to
      IB-PEG3.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 33

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

```
<210> SEQ ID NO 34
<211> LENGTH: 40
<212> TYPE: PRT
<213> ORGANISM: Artificial Sequence
<220> FEATURE:
<223> OTHER INFORMATION: A peptide derivate of formula (34)
<220> FEATURE:
<221> NAME/KEY: MOD_RES
<222> LOCATION: (40)..(40)
<223> OTHER INFORMATION: An amino group of a side chain is bound to
      IB-PEG3.  A carboxyl group of a C-terminus is amidated.

<400> SEQUENCE: 34

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35                  40
```

```
<210> SEQ ID NO 35
<211> LENGTH: 39
<212> TYPE: PRT
<213> ORGANISM: Artificial Sequence
<220> FEATURE:
<223> OTHER INFORMATION: A peptide derivate of formula (35)
<220> FEATURE:
<221> NAME/KEY: MOD_RES
<222> LOCATION: (12)..(12)
<223> OTHER INFORMATION: An amino group of a side chain is bound to
      [123I]IB-PEG3.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 35

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

```
                20                  25                  30

Ser Gly Ala Pro Pro Pro Ser
        35

<210> SEQ ID NO 36
<211> LENGTH: 40
<212> TYPE: PRT
<213> ORGANISM: Artificial Sequence
<220> FEATURE:
<223> OTHER INFORMATION: A peptide derivate of formula (36)
<220> FEATURE:
<221> NAME/KEY: MOD_RES
<222> LOCATION: (40)..(40)
<223> OTHER INFORMATION: An amino group of a side chain is bound to
      [123I]IB-PEG3.  A carboxyl group of a C-terminus is amidated.

<400> SEQUENCE: 36

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Lys
        35                  40

<210> SEQ ID NO 37
<211> LENGTH: 39
<212> TYPE: PRT
<213> ORGANISM: Artificial Sequence
<220> FEATURE:
<223> OTHER INFORMATION: A peptide derivate of formula (37)
<220> FEATURE:
<221> NAME/KEY: MOD_RES
<222> LOCATION: (12)..(12)
<223> OTHER INFORMATION: An amino group of a side chain is bound to
      [125I]IB-ePEG12.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 37

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: A peptide derivate of formula (38)
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (12)..(12)
<223> OTHER INFORMATION: An amino group of a side chain is bound to
      ePEG12.
<220> FEATURE:
<221> NAME/KEY: MOD_RES
<222> LOCATION: (27)..(27)
<223> OTHER INFORMATION: An amino group of a side chain is bound to
      Fmoc.
```

```
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: A peptide derivate of formula (39)
<220> FEATURE:
<221> NAME/KEY: MOD_RES
<222> LOCATION: (12)..(12)
<223> OTHER INFORMATION: An amino group of a side chain is bound to
      [123I]IB-ePEG12.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 39

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

PEPTIDE DERIVATIVE AND USE OF THE SAME

CROSS-REFERENCE TO RELATED APPLICATIONS

This application claims priority to Provisional Application No. 61/391,374, filed Oct. 8, 2010 and Provisional Application No. 61/496,931, filed Jun. 14, 2011; each of which is hereby incorporated by reference in its entirety.

SEQUENCE LISTING SUBMISSION VIA EFS-WEB

A computer readable text file, entitled "068022-5039-SequenceListing.txt," created on or about Oct. 7, 2011 with a file size of about 30 kb contains the sequence listing for this application and is hereby incorporated by reference in its entirety.

BACKGROUND OF INVENTION

1. Field of the Invention

The present invention relates to a peptide derivative, and to the use of the same.

2. Description of Related Art

Today, the estimated number of type-II diabetics in Japan exceeds 8,800,000 according to the statistic in fiscal 2007, and has been increasing further continuously, as compared with fiscal 2002. As a measure against this increase, interventions for preventing diabetes from developing have been made based on the glucose tolerance test, resulting, however, in unsatisfactory effects. The cause is as follows: at such a borderline stage that functional abnormalities are found by the glucose tolerance test, disorders of pancreatic islets have already advanced to a high degree, and this stage possibly is too late as a time for starting interventions.

Recently, it has been reported at home and overseas that even in type-II diabetics the amount of pancreatic islets already has decreased upon the development, and it has been considered that a further decrease in pancreatic β-cells after the development is one of the resistance factors against treatment for type-II diabetics. Therefore, if the amount of pancreatic islets and/or the amount of pancreatic β-cells is detected, there is possibility for the clarification of pathogenesis, the ultra-early diagnosis, and the prevention of development of type-I and type-II diabetes. For this purpose, molecular probes for imaging that allow determination of the amount of pancreatic islets and/or the amount of pancreatic β-cells have been researched and developed.

In designing a molecular probe for imaging, various target molecules in pancreatic cells, particularly functional proteins specific in the β-cells, are being researched. Among these, GLP-1R (glucagon-like peptide-1 receptor) is being researched as a target molecule; GLP-1R is distributed in pancreatic β-cells, and is a seven-transmembrane G protein coupled receptor.

As molecular probes for imaging that use GLP-1R as a target molecule, the following are researched: a peptide derivative of GLP-1 having a C-terminus to which a labeling molecule is bonded; a peptide derivative of exendin-3 having a C-terminus to which a labeling molecule is bonded; and a peptide derivative of exendin-4 having a C-terminus to which a labeling molecule is bonded (e.g., JP 2008-511557 A; M. Gotthardt et al., "A new technique for in vivo imaging of specific GLP-1 binding sites": First results in small rodents, Regulatory Peptides 137 (2006) 162-267; and M. Beche et al., "Are radiolabeled GLP-1 receptor antagonists useful for scintigraphy?": 2009 SNM Annual Meeting, abstract, Oral Presentations No. 327). In addition, a derivative of exendin (9-39) is proposed (e.g., WO 2010/032509; M. Beche et al., "Are radiolabeled GLP-1 receptor antagonists useful for scintigraphy?": 2009 SNM Annual Meeting, abstract, Oral Presentations No. 327; and H. Kimura et al., Development of in vivo imaging agents targeting a glucagon-like peptide-1 receptor (GLP-1R) in pancreatic islets. 2009 SNM Annual Meeting, abstract, Oral Presentations No. 326).

SUMMARY OF THE INVENTION

The present invention provides a peptide derivative useful for imaging of pancreatic β-cells.

The present invention relates to a peptide derivative represented by the following general formula (I):

(I)

where ExP represents polypeptide that is represented by an amino acid sequence of the following formula (1) and contains completely or partially the amino acid sequence of exendin-4

```
                                          (SEQ ID NO. 1)
(HGEGTFTSDLSKQMEEEAVRLFIEWLKNGGPSSGAPPPS),

Ex4(x-y)-K_n  (1)
``` where Ex4(x-y) represents the amino acid sequence of SEQ ID No. 1 between positions x and y, x is an integer of 1 to 9, y is an integer of 30 to 39, K represents lysine, and n is 0 or 1, the α-amino group at the N-terminus of the polypeptide ExP is not modified, modified with a modifying group having no electric charge, or bonded to a -L-Z group, the carboxylic group at the C-terminus of the polypeptide ExP is amidated, and the -L-Z group represents a group represented by the following formula (II) that is bonded to an amino acid side chain of or the α-amino group at the N-terminus of the polypeptide represented by the amino acid sequence of the formula (1),

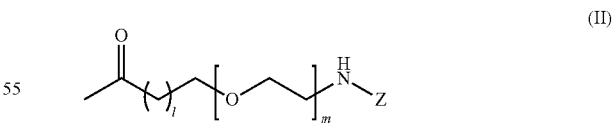

(II)

where l is 0, 1 or 2 and m is an integer of 1 to 30 when n in the formula (1) is 1, l is an integer of 0 to 8 and m is an integer of 0 to 30 when n in the formula (1) is 0, and Z represents a labeling group containing a radionuclide or isotope thereof.

Another aspect of the present invention relates to a peptide derivative as the labeling precursor of the peptide derivative of the present invention (hereinafter simply referred also to as the "labeling precursor"), which is represented by the following general formula (IV)

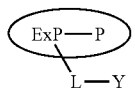

(IV)

where ExP-P is polypeptide that is represented by an amino acid sequence of the following formula (1) and contains completely or partially the amino acid sequence of exendin-4

(SEQ ID NO. 1)
(HGEGTFTSDLSKQMEEEAVRLFIEWLKNGGPSSGAPPPS),

Ex4(x-y)-K$_n$ (1)

where Ex4(x-y) represents the amino acid sequence of SEQ ID No. 1 between positions x and y, x is an integer of 1 to 9, y is an integer of 30 to 39, K represents lysine, and n is 0 or 1, the α-amino group at the N-terminus of the polypeptide ExP-P is bonded to a protecting group or -L-Y group, modified with a modifying group having no electric charge, or not modified, the carboxylic group at the C-terminus of the polypeptide ExP-P is amidated, and the -L-Y group represents a group represented by the following formula (V) that is bonded to an amino acid side chain of or the α-amino group at the N-terminus of the polypeptide represented by the formula (1),

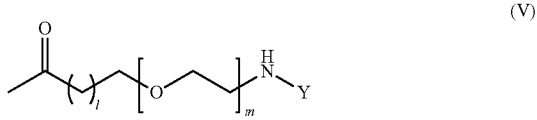

(V)

where l is 0, 1 or 2 and m is an integer of 1 to 30 when n in the formula (1) is 1, l is an integer of 0 to 8 and m is an integer of 0 to 30 when n in the formula (1) is 0, and Y represents a hydrogen atom or radioactive labeling introduction group.

According to the present invention, it is possible to provide a peptide derivative useful for imaging of pancreatic β-cells, preferably imaging of GLP-1R of pancreatic β-cells.

DETAILED DESCRIPTION OF THE EMBODIMENTS

Figure 1:
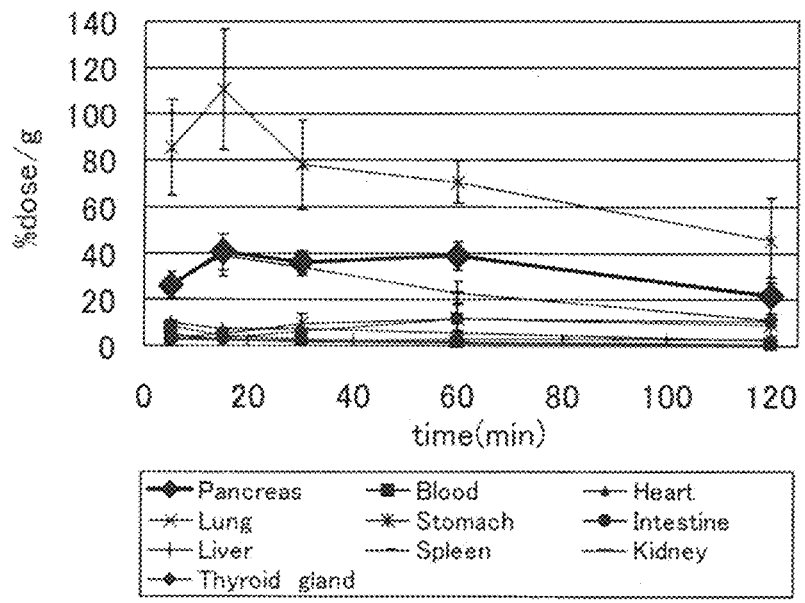
FIG. 1 is a graph showing exemplary time-variations of biodistribution of a peptide derivative of Example 1.

The diameter of a pancreatic islet is, for example, approximately 50 to 500 μm in the case of a human. In order to noninvasively image or quantify such pancreatic islets in vivo, a molecular probe, for example, is considered to be necessary that can accumulate specifically in pancreatic islets, thereby making contrast between pancreatic islets and surrounding tissues. The aforementioned various researches and developments of molecular probes therefore have been made, but from the viewpoint of clearer imaging or more accurate quantification, a new molecular probe has been desired that accumulates more specifically in the pancreas and provides a desired contrast (S/N ratio) with respect to the organs surrounding the pancreas.

The present invention is based on the finding that, with the peptide derivative represented by the general formula (I), it is possible to provide a molecular probe that exhibits improved specificity to pancreatic β-cells, preferably to GLP-1R of pancreatic β-cells and/or an improved blood clearance, provides a desired S/N ratio and useful for imaging by positron emission tomography (PET) or single photon emission computed tomography (SPECT).

Also, the present invention is based on the finding that, with use of the peptide derivative represented by the general formula (IV) as the labeling precursor, the above-described peptide derivative represented by the general formula (I) can be produced with ease, and moreover, yields at the time of labeling can be improved and the time involved in the labeling can be reduced.

In other words, the present invention relates to the following:

[1] A peptide derivative represented by the following general formula (I)

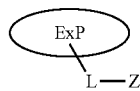

(I)

where ExP represents polypeptide that is represented by an amino acid sequence of the following formula (1) and contains completely or partially the amino acid sequence of exendin-4

(SEQ ID NO. 1)
(HGEGTFTSDLSKQMEEEAVRLFIEWLKNGGPSSGAPPPS),

Ex4(x-y)-$K_n$ (1)

where Ex4(x-y) represents the amino acid sequence of SEQ ID No. 1 between positions x and y, x is an integer of 1 to 9, y is an integer of 30 to 39, K represents lysine, and n is 0 or 1, the α-amino group at the N-terminus of the polypeptide ExP is not modified, modified with a modifying group having no electric charge, or bonded to a -L-Z group, the carboxylic group at the C-terminus of the polypeptide ExP is amidated, and the -L-Z group represents a group represented by the following formula (II) that is bonded to an amino acid side chain of or the α-amino group at the N-terminus of the polypeptide represented by the amino acid sequence of the formula (1),

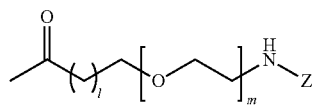
(II)

where l is 0, 1 or 2 and m is an integer of 1 to 30 when n in the formula (1) is 1, l is an integer of 0 to 8 and m is an integer of 0 to 30 when n in the formula (1) is 0, and Z represents a labeling group containing a radionuclide or isotope thereof.

[2] The peptide derivative according to [1], wherein Ex4(x-y)-$K_n$ is any of the amino acid sequences of the following formulae (2) to (5):

(SEQ ID NO. 2)
HGEGTFTSDLSKQMEEEAVRLFIEWLKNGGPSSGAPPPS (2)

(SEQ ID NO. 3)
HGEGTFTSDLSKQMEEEAVRLFIEWLKNGGPSSGAPPPSK (3)

(SEQ ID NO. 4)
DLSKQMEEEAVRLFIEWLKNGGPSSGAPPPS (4)

(SEQ ID NO. 5)
DLSKQMEEEAVRLFIEWLKNGGPSSGAPPPSK (5).

[3] The peptide derivative according to [1] or [2], wherein the -L-Z group is bonded to the amino group of the side chain of lysine that corresponds to position 12 of the amino acid sequence of SEQ ID NO. 1 or to the amino group of the side chain of K in the formula (1).

[4] The peptide derivative according to any one of [1] to [3], wherein Z is a group represented by the following formula (III),

(III)

where Ar represents an aromatic hydrocarbon group or aromatic heterocyclic group, $R^1$ represents a substituent containing a radionuclide or isotope thereof, $R^2$ represents a hydrogen atom or one or more substituents different from the substituent represented by $R^1$, and $R^3$ represents a bond, alkylene group having 1 to 6 carbon atoms or oxyalkylene group having 1 to 6 carbon atoms.

[5] The peptide derivative according to any one of [1] to [4], Z represents a labeling group containing a radionuclide.

[6] A composition comprising the peptide derivative according to any one of [1] to [5].

[7] A reagent for imaging comprising the peptide derivative according to [5].

[8] A peptide derivative represented by the following general formula (IV),

(IV)

where ExP-P represents polypeptide that is represented by an amino acid sequence of the following formula (1) and contains completely or partially the amino acid sequence of exendin-4

(SEQ ID NO. 1)
(HGEGTFTSDLSKQMEEEAVRLFIEWLKNGGPSSGAPPPS),
Ex4(x-y)$K_n$ (1)

where Ex4(x-y) represents the amino acid sequence of SEQ ID No. 1 between positions x and y, x is an integer of 1 to 9, y is an integer of 30 to 39, K represents lysine, and n is 0 or 1, an α-amino group at an N-terminus of the polypeptide ExP-P is bonded to a protecting group or -L-Y group, modified with a modifying group having no electric charge, or not modified, a carboxylic group at a C-terminus of the polypeptide ExP-P is amidated, and the -L-Y group represents a group represented by the following formula (V) that is bonded to an amino acid side chain of or the α-amino group at the N-terminus of the polypeptide represented by the formula (1),

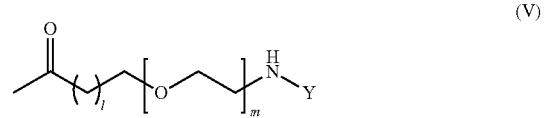
(V)

where l is 0, 1 or 2 and m is an integer of 1 to 30 when n in the formula (1) is 1, l is an integer of 0 to 8 and m is an integer of 0 to 30 when n in the formula (1) is 0, and Y represents a hydrogen atom or radioactive labeling introduction group.

[9] The peptide derivative according to [8], wherein Ex4(x-y)-$K_n$ is any of the amino acid sequences of the following formulae (2) to (5):

```
                                              (SEQ ID NO. 2)
HGEGTFTSDLSKQMEEEAVRLFIEWLKNGGPSSGAPPPS    (2)

(SEQ ID NO. 3)
HGEGTFTSDLSKQMEEEAVRLFIEWLKNGGPSSGAPPPSK   (3)

(SEQ ID NO. 4)
DLSKQMEEEAVRLFIEWLKNGGPSSGAPPPS            (4)

(SEQ ID NO. 5)
DLSKQMEEEAVRLFIEWLKNGGPSSGAPPPSK           (5).
```

[10] A kit for producing the peptide derivative according to [5], comprising the peptide derivative according to any one of [1] to [4] in which Z represents a labeling group containing a non-radioisotope of a radionuclide, and/or the peptide derivative according to [8] or [9].

[11] A method for imaging pancreatic β-cells, comprising
detecting a signal of a radionuclide of the peptide derivative according to [5] from an analyte to which the peptide derivative has been administered in advance.

[12] The method according to [11], further comprising reconfiguring the detected signal to convert the signal into an image, and displaying the image.

[13] A method for determining an amount of pancreatic islets, the method comprising: detecting a signal of the peptide derivative according to [5] from an analyte to which the peptide derivative has been administered; and calculating an amount of pancreatic islets from the detected signal of the peptide derivative.

[14] The method according to [13], further comprising presenting the calculated amount of pancreatic islets.

The present invention achieves the effect of providing a molecular probe useful for imaging that accumulates specifically in pancreatic β-cells and has an excellent blood clearance. Further, the present invention can also achieve the effect of, for example, detecting an amount of pancreatic β-cells, and moreover, allowing the clarification of pathogenesis, the ultra-early diagnosis, and/or the prevention of development of diseases such as type-I and type-II diabetes.

Further, the present invention achieves the effect of providing a molecular probe useful for imaging at low production cost in an efficient manner because of its high labeling yields at the time of radioactive labeling and the reduced time involved in the labeling.

[Peptide Derivative]

The peptide derivative of the present invention is represented by the following general formula (I).

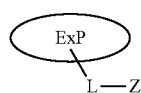

(I)

For example, the peptide derivative according to the present invention has excellent specificity to pancreatic β-cells, preferably to GLP-1R of pancreatic β-cells. Also, the peptide derivative of the present invention has an excellent blood clearance. For these reasons, the peptide derivative of the present invention can be used for imaging of pancreatic β-cells, preferably for quantification of pancreatic β-cells and/or imaging of GLP-1R of pancreatic β-cells.

In the general formula (I), ExP represents polypeptide that is represented by the amino acid sequence of the following formula (1) and contains completely or partially the amino acid sequence of exendin-4 (SEQ ID NO. 1):

Ex4(x-y)-$K_n$           (1).

Ex4(x-y) is the amino acid sequence of SEQ ID No. 1 between positions x and y. Both x and y represent the number of amino acid residues counted from the N-terminus side of the amino acid sequence of SEQ ID No. 1. x is an integer of 1 to 9 and y is an integer of 30 to 39. Although combinations of x and y are not particularly limited and can be selected appropriately, x preferably is an integer of 1 or 9 and y preferably is 39. For example, Ex4(x-y) preferably is Ex4(1-39) or Ex4 (9-39). When x is 9 and y is 39, the amino acid sequence of Ex4(x-y) corresponds with the amino acid sequence of exendin(9-39) as the GLP-1R antagonist.

K of $K_n$ represents a lysine residue that can be bonded to the C-terminus of Ex4(x-y) and n is 0 or 1. That is, when n is 1 (i.e., $K_1$), it means that lysine is bonded to the C-terminus of Ex4(x-y) and when n is 0 (i.e., $K_0$), it means that no lysine is bonded to the C-terminus of Ex4(x-y). Although the lysine to be bonded to the C-terminus may be in L-form (L-lysine) or D-form (D-lysine), the lysine preferably is in D-form in terms of suppressing peptide decomposition in vivo from the C-terminus side so as to prevent detection of signals from the decomposition products.

A -L-Z group represents a group represented by the following formula (II) that is bonded to an amino acid side chain of or the α-amino group at the N-terminus of the polypeptide ExP (the polypeptide having the amino acid sequence of the formula (1)), preferably to the amino group of the side chain of lysine of or the α-amino group at the N-terminus of the polypeptide ExP. Specifically, a -L- group is represented by the following formula (II').

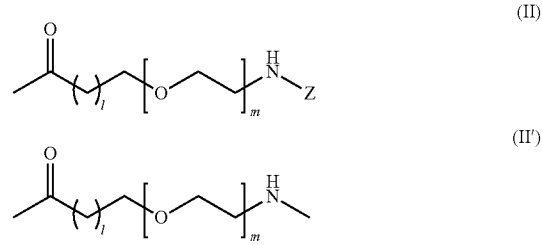

In the formula (II), l represents the number of methylene groups and m represents the number of oxyethylene groups. When n in the formula (1) is 1, l is 0, 1 or 2, and preferably 0 or 1. In the same instance, m is an integer of 1 to 30. In terms of suppressing the accumulation of the peptide derivative in liver, kidney, lungs and intestines and improving the ratio of pancreas/liver and the ratio of pancreas/kidney, m preferably is an integer of 3 to 30 and more preferably is an integer of 4 or more, 6 or more, 8 or more, 10 or more or 12 or more. An upper limit to m preferably is an integer of 28 or less, 26 or less, 24 or less, 22 or less, 20 or less, 18 or less, 16 or less, 14 or less or 12 or less. Further, in terms of improving the accumulation in pancreas, m is, for example, an integer of 1 to 14, preferably an integer of 2 to 12 and more preferably an integer of 2 to 8. Further, when n in the formula (1) is 0, l is an integer of 0 to 8, preferably an integer of 0 to 5, more preferably an integer of 0 to 3, and even more preferably 0 or 1. In the same instance, m is an integer of 1 to 30. In terms of suppressing the accumulation of the peptide derivative in liver, kidney, lungs and intestines and improving the ratio of pancreas/liver and the ratio of pancreas/kidney, m preferably is an integer of 4 to 30 and more preferably is an integer of 6 or more, 8 or more, or 10 or more. An upper limit to m preferably is an integer of 28 or less, 26 or less, 24 or less, 22 or less, 20 or less, 18 or less, 16 or less, or 14 or less. Further, in terms of improving the accumulation in pancreas, m is, for example, an integer of 0 to 14, preferably an integer of 0 to 12, and more preferably an integer of 2 to 8.

Z represents a labeling group containing a radionuclide or isotope thereof. In the present specification, the "labeling group containing a radionuclide or isotope thereof" include radionuclides and isotopes thereof. The isotopes include radioisotopes and non-radioisotopes of radionuclides. The labeling group containing a radionuclide or isotope thereof is not particularly limited as long as it is a group that can be bonded to an amino group as shown in the formula (II), and any of various known labeling groups can be used.

Examples of the radionuclide include $^{11}C$, $^{13}N$, $^{15}O$, $^{18}F$, $^{64}Cu$, $^{67}Ga$, $^{68}Ga$, $^{75}Br$, $^{76}Br$, $^{77}Br$, $^{82}Rb$, $^{99m}Tc$, $^{111}In$, $^{123}I$, $^{124}I$, $^{125}I$, $^{131}I$, and $^{186}Re$. From the viewpoint of performing PET, the radionuclide preferably is a positron emission nuclide such as $^{11}C$, $^{13}N$, $^{15}O$, $^{18}F$, $^{62}Cu$, $^{64}Cu$, $^{68}Ga$, $^{75}Br$, $^{76}Br$, $^{82}Rb$, or $^{124}I$. From the viewpoint of performing SPECT, the radionuclide preferably is a γ-emission nuclide such as $^{67}Ga$, $^{99m}Tc$, $^{77}Br$, $^{111}In$, $^{123}I$, or $^{125}I$, and more preferably is $^{77}Br$, $^{99m}Tc$, $^{111}In$, $^{123}I$, or $^{125}I$. Among these, radioactive halogen nuclides such as $^{18}F$, $^{75}Br$, $^{76}Br$, $^{77}Br$, $^{123}I$, and $^{124}I$ are preferred more, and $^{18}F$, $^{123}I$, and $^{124}I$ are preferred particularly as the radionuclide. The non-radioisotope of the radionuclide is any of non-radioisotopes of the above-mentioned radionuclides, and examples of the same include $^{13}C$, $^{14}N$, $^{16}O$, $^{17}F$, $^{63}Cu$, $^{70}Ga$, $^{80}Br$, $^{99m}Tc$, $^{115}In$ and $^{127}I$.

In terms of the affinity between the peptide derivative and pancreatic β-cells, preferably the affinity between the peptide derivative and GLP-1R of pancreatic β-cells, the labeling group containing a radionuclide or isotope thereof preferably is a group represented by the following formula (III).

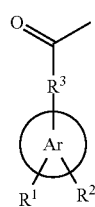

(III)

Ar represents an aromatic hydrocarbon group or aromatic heterocyclic group. The aromatic hydrocarbon group preferably is an aromatic hydrocarbon group having a carbon number of 6 to 18, and examples of the same include phenyl group, o-tolyl group, m-tolyl group, p-tolyl group, 2,4-xylyl group, p-cumenyl group, mesityl group, 1-naphthyl group, 2-naphthyl group, 1-anthryl group, 2-anthryl group, 9-anthryl group, 1-phenanthryl group, 9-phenanthryl group, 1-acenaphthyl group, 2-azulenyl group, 1-pyrenyl group, 2-triphenylenyl group, o-biphenylyl group, m-biphenylyl group, p-biphenylyl group, and terphenyl group. The aromatic heterocyclic group preferably is a 5 to 10-membered heterocyclic group having one or two nitrogen atoms, oxygen atoms, or sulfur atoms, and examples of the same include triazolyl group, 3-oxadiazolyl group, 2-furyl group, 3-furyl group, 2-thienyl group, 3-thienyl group, 1-pyrrolyl group, 2-pyrrolyl group, 3-pyrrolyl group, 2-pyridyl group, 3-pyridyl group, 4-pyridyl group, 2-pyradyl group, 2-oxazolyl group, 3-isoxyazolyl group, 2-thiazolyl group, 3-isothiazolyl group, 2-imidazolyl group, 3-pyrazolyl group, 2-quinolyl group, 3-quinolyl group, 4-quinolyl group, 5-quinolyl group, 6-quinolyl group, 7-quinolyl group, 8-quinolyl group, 1-isoquinolyl group, 2-quinoxalynyl group, 2-benzofuryl group, 2-benzothienyl group, N-indolyl group, and N-carbazolyl group. Ar preferably is, among these, phenyl group, triazolyl group, or pyridyl group, and more preferably, phenyl group.

$R^1$ represents a substituent containing a radionuclide or isotope thereof, and examples of the same include radionuclides, radionuclide-substituted $C_1$-$C_3$ alkyl groups, radionuclide-substituted $C_1$-$C_3$ alkoxy groups, isotopes of radionuclides, radionuclide-isotope-substituted $C_1$-$C_3$ alkyl groups, and radionuclide-isotope-substituted $C_1$-$C_3$ alkoxy groups.

In the present specification, the "$C_1$-$C_3$ alkyl groups" refer to alkyl groups that have 1 to 3 carbon atoms, and examples of the same include methyl group, ethyl group, and propyl group. In the present specification, the "radionuclide-substituted or radionuclide-isotope-substituted $C_1$-$C_3$ alkyl groups" refer to alkyl groups that have 1 to 3 carbon atoms and in which the aforementioned radionuclide or isotope thereof substitutes for a hydrogen atom. In the present specification, the "$C_1$-$C_3$ alkoxy groups" refer to alkoxy groups that have 1 to 3 carbon atoms, and examples of the same include methoxy group, ethoxy group, and propoxy group. In the present specification, the "radionuclide-substituted or radionuclide-isotope-substituted $C_1$-$C_3$ alkoxy groups" refer to alkoxy groups that have 1 to 3 carbon atoms and in which the aforementioned radionuclide or isotope thereof substitutes for a hydrogen atom.

$R^1$ preferably represents a substituent containing a radioactive halogen nuclide, and more preferably a substituent containing $^{18}F$, $^{75/76/77}Br$, or $^{123/124/125/131}I$, for example. From the viewpoint of performing PET, $R^1$ preferably represents a substituent containing a radioactive halogen nuclide that emits positron, that is, for example, a substituent containing $^{18}F$, $^{75}Br$, $^{76}Br$, or $^{124}I$. From the viewpoint of performing SPECT, $R^1$ preferably represents a substituent containing a radioactive halogen nuclide that emits γ-rays, that is, for example, a substituent containing $^{77}Br$, $^{123}I$, or $^{125}I$. $R^1$ may be at any of an ortho-position, a meta-position, and a para-position. The meta-position is preferred when $R^1$ represents $^{123/124/125/131}I$ or isotope thereof, and the para-position is preferred when $R^1$ represents $^{18}F$ or isotope thereof. It should be noted that, in the present specification, "$^{75/76/77}Br$" refers to $^{75}Br$, $^{76}Br$ or $^{77}Br$ and "$^{123/124/125/131}I$" refers to $^{123}I$, $^{124}I$, $^{125}I$ or $^{131}I$.

$R^2$ represents a hydrogen atom or one or more substituents different from the substituent represented by $R^1$. Although $R^2$ can be a hydrogen atom or substituents, a hydrogen atom is preferred. That is, in the formula (I), Ar preferably is not replaced with a substituent other than the substituent represented by $R^1$. When $R^2$ represents two or more substituents, the substituents may all be the same or they may be different from each other. Examples of the substituent include hydroxyl group, electron attractive groups, electron donative groups, $C_1$-$C_6$ alkyl groups, $C_2$-$C_6$ alkenyl groups, and $C_2$-$C_6$ alkynyl groups. Examples of electron attractive groups include cyano group, nitro group, halogen atoms, carbonyl group, sulfonyl group, acetyl group, and phenyl group. Examples of halogen atoms include fluorine atom, chlorine atom, bromine atom, and iodine atom. In the present specification, the "$C_1$-$C_6$ alkyl group" refers to an alkyl group having 1 to 6 carbon atoms, and examples of the same include methyl group, ethyl group, propyl group, isopropyl group, butyl group, isobutyl group, sec-butyl group, tert-butyl group, pentylene group, isopentyl group, and hexylene group. In the present specification, the "$C_2$-$C_6$ alkenyl group" refers to an alkenyl group having 2 to 6 carbon atoms, and examples of the same include vinyl group, 1-propenyl group, 2-propenyl group, isopropenyl group, 1-butenyl group, 2-butenyl group, and 3-butenyl group. In the present specification, the "$C_2$-$C_6$ alkynyl group" refers to an alkynyl group having 2 to 6 carbon atoms, and examples of the same include ethynyl group, 1-propynyl group, 2-propynyl group, 1-butynyl group, 2-butynyl group, and 3-butynyl group. Among these, the substituent preferably is a hydroxyl group or electron attractive group.

$R^3$ preferably represents a bond, alkylene group having 1 to 6 carbon atoms, or oxyalkylene group having 1 to 6 carbon atoms. Examples of the alkylene group having 1 to 6 carbon atoms include straight-chain or branched-chain alkylene groups, such as methylene group, ethylene group, propylene group, butylene group, pentyl group, and hexyl group. Examples of the oxyalkylene group having 1 to 6 carbon atoms include oxymethylene group, oxyethylene group, oxypropylene group, oxybutylene group, and oxypentylene group. $R^3$ preferably is a bond, methylene group, or ethylene group, and more preferably, a bond, in terms of the affinity between the peptide derivative and pancreatic islets, preferably the affinity between the peptide derivative and pancreatic β-cells, and more preferably the affinity between the peptide derivative and GLP-1R of pancreatic β-cells.

In terms of the affinity between the peptide derivative and pancreatic β-cells, preferably the affinity between the peptide derivative and GLP-1R of pancreatic β-cells, the group represented by the formula (III) preferably is a group represented by the formula (IIIa), and more preferably a group represented by the formula (IIIb) or (IIIc). In the formula (IIIa), $R^1$ is as described above. Further, the group represented by the formula (III) preferably is a group represented by the formula (IIId) in terms of the general versatility.

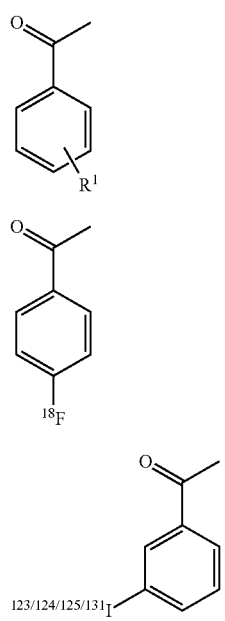

From the viewpoint of performing labeling with a metal radioisotope (radioactive metal nuclide), the labeling group containing a radionuclide or isotope thereof may contain a radioactive metal nuclide and a chelating site that can chelate the radioactive metal nuclide. Examples of compounds that can form a chelating site include diethylenetriaminepentaacetic acid (DTPA), 6-hydrazinopyridine-3-carboxylic acid (HYNIC), tetraazacyclododecanetetraacetic acid (DOTA), dithisosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO).

The carboxylic group at the C-terminus of the polypeptide ExP is amidated with an amino group in terms of improving the bonding to pancreatic β-cells and/or the stability in vivo. Although the amino acid positioned at the C-terminus of the polypeptide ExP can be in L-form (L-amino acid) or D-form (D-amino acid), D-form is preferred in terms of suppressing peptide decomposition in vivo from the C-terminus side.

When the polypeptide ExP is polypeptide that is represented by Ex4(x-y)-$K_1$ and the -L-Z group is bonded to K (lysine) at the C-terminus, the lysine to which the -L-Z group is bonded preferably is D-lysine in terms of suppressing peptide decomposition in vivo from the C-terminus side so as to prevent detection of signals from the decomposition products. In this case, although the amino acid next to the lysine at the C-terminus to which the -L-Z group is bonded, namely, the amino acid at position (y-(x-1)) may be either in L-form or D-form, D-form is more preferable in terms of suppressing peptide decomposition in vivo from the C-terminus side so as to prevent detection of signals from the decomposition products. For example, when y is 39, the serine at position (40-x) may be either L-serine or D-serine but D-serine is preferable in terms of the same reason as mentioned above.

The α-amino group at the N-terminus of the polypeptide ExP may be not modified or modified, in terms of canceling the positive electric charge of the α-amino group at the N-terminus to prevent the accumulation of the peptide derivative in the kidney, with a modifying group having no electric charge. Or, the α-amino group at the N-terminus may be bonded to the -L-Z group.

Examples of modifying groups having no electric charge include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having a carbon number of 3 to 20, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy-2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene) ethyl group (Dde), 2,6-dichlorobenzyl group (2,6-DiCl-Bzl), 2-chlorobenzyloxycarbonyl group (2-Cl—Z), 2-bromobenzyloxycarbonyl group (2-Br—Z), benzyloxymethyl group (Bom), cyclohexyloxy group (cHxO), t-butoxymethyl group (Bum), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl (Cl-z) group, cyclohexyl group, cyclopentyl group, isopropyl group, pivalyl group, tetrahydropyran-2-yl group, and trimethylsilyl group. Among these, preferably, the modifying group is acetyl group, benzyl group, benzyloxymethyl group, o-bromobenzyloxycarbonyl group, t-butyl group, t-butyldimethylsilyl group, 2-chlorobenzyl group, 2,6-dichlorobenzyl group, cyclohexyl group, cyclopentyl group, isopropyl group, pivalyl group, tetrahydropyran-2-yl group, tosyl group, trimethylsilyl group, or trityl group. More preferably, the modifying group is acetyl group.

For example, Ex4(x-y)-$K_n$ preferably is Ex4(1-39), Ex4(1-39)-K, Ex4(9-39), or Ex4(9-39)-K. Specifically, Ex4(x-y)-$K_n$ preferably is any of the amino acid sequences of the following formulae (2) to (5):

```
                                                    (SEQ ID NO. 2)
HGEGTFTSDLSKQMEEEAVRLFIEWLKNGGPSSGAPPPS (2)

(SEQ ID NO. 3)
HGEGTFTSDLSKQMEEEAVRLFIEWLKNGGPSSGAPPPSK (3)

(SEQ ID NO. 4)
DLSKQMEEEAVRLFIEWLKNGGPSSGAPPPS (4)

(SEQ ID NO. 5)
DLSKQMEEEAVRLFIEWLKNGGPSSGAPPPSK (5).
```

When Ex4(x-y)-$K_n$ is the amino acid sequence of the formula (2), the -L-Z group preferably is bonded to, for example, the amino group of the side chain of lysine at position 12 (hereinafter referred also to as "Lys12") of or the α-amino group of the amino acid sequence of the formula (2), and more preferably is bonded to the amino group of the side chain of Lys12. When Ex4(x-y)-$K_n$ is the amino acid sequence of the formula (3), the -L-Z group preferably is bonded to the amino group of the side chain of lysine at position 40 of the amino acid sequence of the formula (3) (hereinafter referred also to as "Lys40") and Lys40 preferably is D-lysine in terms of suppressing peptide decomposition in vivo from the C-terminus side so as to prevent detection of signals from the decomposition products. In this case, the serine at position 39 preferably is D-serine in terms of the same reason as mentioned above.

When Ex4(x-y)-$K_n$ is the amino acid sequence of the formula (4), the -L-Z group preferably is bonded to, for example, the amino group of the side chain of lysine at position 4 (hereinafter referred also to as "Lys4") of or the α-amino group at the N-terminus of the amino acid sequence of the formula (4), and more preferably is bonded to the amino group of the side chain of Lys4. When Ex4(x-y)-$K_n$ is the amino acid sequence of the formula (5), the -L-Z group preferably is bonded to the amino group of the side chain of lysine at position 32 of the amino acid sequence of the formula (5) (hereinafter referred also to as "Lys32") and Lys 32 preferably is D-lysine in terms of suppressing peptide decomposition in vivo from the C-terminus side so as to prevent detection of signals from the decomposition products. In this case, the serine at position 31 preferably is D-serine in terms of the same reason as mentioned above.

The peptide derivative of the present invention can be used for imaging of pancreatic islets, preferably for imaging of pancreatic β-cells, and more preferably for a molecular probe for imaging GLP-1R of pancreatic β-cells. Further, the peptide derivative of the present invention can be used for imaging for prevention, treatment, or diagnosis of diabetes. Further, the peptide derivative of the present invention can be used for, for example, a composition, a reagent for imaging, a contrast medium and an diagnostic imaging agent that contain the peptide derivative of the present invention as an effective ingredient and are used for the variety of imagings as described above. Although the composition, the diagnostic imaging agent and the like may be in the form of a solution or powder, for example, they are preferably in the form of a solution, and more preferably in the form of a parenteral solution in consideration of the half-life and radioactive decay of the radionuclide.

[Labeling Precursor]

Another aspect of the present invention relates to the peptide derivative represented by the following general formula (IV). For example, the peptide derivative according to this aspect can be utilized as the labeling precursor of the peptide derivative of the present invention.

(IV)

ExP-P represents polypeptide that is represented by the amino acid sequence of the following formula (1) and contains completely or partially the amino acid sequence of exendin-4 (SEQ ID NO. 1):

Ex4(x-y)-$K_n$ (1).

Ex4(x-y)-$K_n$ is the same as that in the peptide derivative of the present invention described above, and particularly, Ex4 (1-39), Ex4(1-39)-K, Ex4(9-39) or Ex4(9-39)-K is preferred. Specifically, it is preferable that Ex4(x-y)-$K_n$ represents any of the amino acid sequences of the formulae (2) to (5). Further, the carboxyl group at the C-terminus of the polypeptide ExP-P is amidated.

A -L-Y group represents a group represented by the following formula (V) that is bonded to an amino acid side chain of or the α-amino group at the N-terminus of the polypeptide ExP-P represented by the amino acid sequence of the formula (1), and preferably is bonded to the amino group of the side chain of lysine of or the α-amino group at the N-terminus of the polypeptide ExP-P. A -L- group, l and m are the same as those in the peptide derivative of the present invention described above.

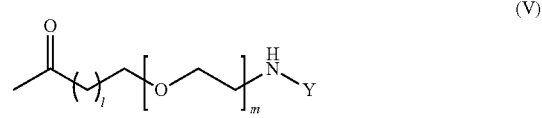

(V)

Y represents a hydrogen atom or radioactive labeling introduction group. Y preferably represents a hydrogen atom in terms of allowing the production of the peptide derivative of the present invention with ease, preferably performing labeling in a short time, and moreover achieving excellent labeling yields.

In the present specification, the "radioactive labeling introduction group" refers to a group capable of introducing a radionuclide or a radioactive labeling group containing a radionuclide. In the present specification, examples of being "capable of introducing a radionuclide or a radioactive labeling group containing a radionuclide" include a radioactive labeling introduction group or a specific functional group having a radioactive labeling introduction group being replaceable with a radionuclide, bondable to or chelatable of a radionuclide, and bondable to a radioactive labeling group containing a radionuclide.

From the viewpoint of performing labeling with a radioactive metal nuclide, the radioactive labeling introduction group may contain a radioactive metal nuclide and a chelating site that can chelate the radioactive metal nuclide. Chelate compounds that form a chelating site are as described above.

Examples of the radioactive labeling introduction group include a group represented by the following formula (VI) in terms of the affinity between the peptide derivative to be obtained after the labeling and pancreatic β-cells, preferably the affinity between the peptide derivative and GLP-1R of pancreatic β-cells.

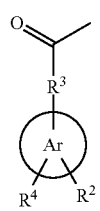

(VI)

In the formula (VI), Ar, $R^2$ and $R^3$ are the same as those in the formula (III). $R^4$ represents a substituent having a mesylate (OMs) group, tosylate (OTs) group, triflate (OTf) group, [$^{80}$Br]bromine atom, [$^{127}$I]iodine atom, chlorine atom, nitro group, trimethylammonium group, tin atom, alkyltin group, or alkylsilicon group. An OMs group, OTs group, OTf group, [$^{80}$Br]bromine atom, [$^{127}$I]iodine atom, tin atom, alkyltin group or alkylsilicon group is preferred, and [$^{80}$Br]bromine atom, [$^{127}$I]iodine atom or tin atom is more preferred. The alkyltin group may be tin-atom-substituted $C_1$-$C_6$ alkyl group, preferably a tributyl tin group ($Sn(C_4H_9)_3$). The alkylsilicon group may be silicon-atom-substituted $C_1$-$C_6$ alkyl group, preferably a tributyl silicon group. $R^4$ may be at an ortho-position, meta-position, or para-position. The para-position is preferred in terms of producing a labeling precursor in a fluorine-labeled form. $R^4$ may be at an ortho-position, meta-position, or para-position in terms of producing a labeling precursor in iodine-labeled form.

The group represented by the formula (VI) preferably is a group represented by the following formula (VIa), and more preferably a group represented by the formula (VIa) where $R^4$ is a group representing [$^{80}$Br]bromine atom, [$^{127}$I]iodine atom or tin atom. In the formula (VIa), $R^4$ is as described above.

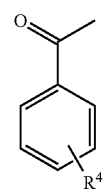

(VIa)

The α-amino group at the N-terminus of the polypeptide ExP-P may be bonded to a protecting group or -L-Y group, modified with a modifying group having no electric charge or not modified. In terms of allowing more selective labeling, the α-amino group at the N-terminus preferably is protected by a protecting group or modified with a modifying group having no electric charge. The modifying group having no electric charge is as described above.

When Ex4(x-y)-$K_n$ is the amino acid sequence of the formula (2), the -L-Y group preferably is bonded to, for example, the α-amino group at the N-terminus of the polypeptide ExP-P or to the amino group of the side chain of Lys12, and more preferably is bonded to the amino group of the side chain of Lys12. When Ex4(x-y)-$K_n$ is the amino acid sequence of the formula (3), the -L-Y group preferably is bonded to the amino group of the side chain of Lys40 and Lys 40 preferably is D-lysine in terms of obtaining a peptide derivative that is prevented from decomposing in vivo from the C-terminus side so as to prevent detection of signals from the decomposition products. In this case, the serine at position 39 preferably is D-serine in terms of the same reason as mentioned above.

When Ex4(x-y)-$K_n$ is the amino acid sequence of the formula (4), the -L-Y group preferably is bonded to, for example, the α-amino group at the N-terminus of the polypeptide ExP-P or to the amino group of the side chain of Lys4, and more preferably is bonded to the amino group of the side chain of Lys4. When Ex4(x-y)-$K_n$ is the amino acid sequence of the formula (5), the -L-Y group preferably is bonded to the amino group of the side chain of Lys32 and Lys32 preferably is D-lysine in terms of obtaining a peptide derivative that is prevented from decomposing in vivo from the C-terminus side so as to prevent detection of signals from the decomposition products. In this case, the serine at position 31 preferably is D-serine in terms of the same reason as mentioned above.

In the polypeptide ExP-P, amino acid side chains to which the -L-Y group is not bonded may be each bonded to a protecting group so as to be protected by it or may not be protected. In terms of allowing more selective labeling, it is preferable that functional groups of amino acid side chains to which the -L-Y group is not bonded are each bonded to a protecting group so as to be protected by it, and it is more preferable that the amino groups of side chains of lysines to which the -L-Y group is not bonded are each protected. In terms of simplifying the operation after the labeling to reduce the production time, amino acid side chains to which the -L-Y group is not bonded preferably are not protected and are being free. For the protecting group, any of known protecting groups capable of protecting functional groups of amino acid side chains to which the -L-Y group of the labeling precursor is not bonded during labeling, preferably those capable of protecting amino groups to which the -L-Y group is not bonded can be used. The protecting group is not particularly limited, and examples of the same include Fmoc, Boc, Cbz, Troc, Alloc, Mmt, amino group, alkyl group having a carbon number of 3 to 20, 9-fluoreneacetyl group, 1-fluorenecarboxylic acid group, 9-fluorenecarboxylic acid group, 9-fluorenone-1-carboxylic acid group, benzyloxycarbonyl group, Xan, Trt, Mtt, Mtr, Mts, Mbh, Tos, Pmc, MeBzl, MeOBzl, BzlO, Bzl, Bz, Npys, Dde, 2,6-DiCl-Bzl, 2-Cl—Z, 2-Br—Z, Bom, cHxO, Bum, tBuO, tBu, Ac and TFA. Fmoc and Boc are preferred in terms of handing.

When $Ex4(x-y)-K_n$ is the amino acid sequence of the formula (2), it is preferable that the -L-Y group is bonded to the amino group of the side chain of Lys12 or to the α-amino group at the N-terminus. In terms of allowing selective labeling, it is more preferable that the -L-Y group is bonded to the amino group of the side chain of Lys12 or to the α-amino group at the N-terminus and a protecting group is bonded to each of the amino groups of side chains of lysines to which the -L-Y group is not bonded. In terms of obtaining a peptide derivative having excellent specificity to pancreatic β-cells, it is more preferable that the -L-Y group is bonded to the amino group of the side chain of Lys12 and a protecting group is bonded to the amino group of the side chain of lysine at position 27 (Lys27), and it is still more preferable that the -L-Y group is bonded to the amino group of the side chain of Lys12 and a protecting group is bonded to each of the amino group of the side chain of Lys27 and the α-amino group at the N-terminus.

When $Ex4(x-y)-K_n$ is the amino acid sequence of the formula (3), it is preferable that the -L-Y group is bonded to the amino group of the side chain of Lys40. In terms of allowing more selective labeling, it is more preferable that the -L-Y group is bonded to the amino group of the side chain of Lys40 and a protecting group is bonded to each of the amino group of the side chain of Lys12 and that of Lys27, and it is still more preferable that the -L-Y group is bonded to the amino group of the side chain of Lys40 and a protecting group is bonded to each of the α-amino group at the N-terminus, the amino group of the side chain of Lys12 and that of Lys27.

When $Ex4(x-y)-K_n$ is the amino acid sequence of the formula (4), it is preferable that the -L-Y group is bonded to the amino group of the side chain of Lys4 or to the α-amino group at the N-terminus. In terms of allowing selective labeling, it is more preferable that the -L-Y group is bonded to the amino group of the side chain of Lys4 or to the α-amino group at the N-terminus and a protecting group is bonded to each of the amino groups of side chains of lysines to which the -L-Y group is not bonded. In terms of obtaining a polypeptide derivative having excellent specificity to pancreatic β-cells, it is more preferable that the -L-Y group is bonded to the amino group of the side chain of Lys4 and a protecting group is bonded to the amino group of the side chain of lysine at position 19 (Lys19), and it is still more preferable that the -L-Y group is bonded to the amino group of the side chain of Lys4 and a protecting group is bonded to each of the amino group of the side chain of Lys19 and the α-amino group at the N-terminus.

When $Ex4(x-y)-K_n$ is the amino acid sequence of the formula (5), the -L-Y group preferably is bonded to the amino group of the side chain of Lys32. In terms of allowing more selective labeling, it is more preferable that the -L-Y group is bonded to the amino group of the side chain of Lys32 and a protecting group is bonded to each of the amino group of the side chain of Lys4 and that of Lys19, and it is still more preferable that the -L-Y group is bonded to the amino group of the side chain of Lys32 and a protecting group is bonded to each of the α-amino group at the N-terminus, the amino group of the side chain of Lys4 and that of Lys19.

Examples of forms of the labeling precursor include a solution and a powder. The labeling precursor preferably is in the form of a powder, and more preferably in the form of a freeze-dried powder (freeze-dried formulation) in terms of the handling.

The labeling precursor can be synthesized using, for example, amino acid in which the α-amino group at the N-terminus is protected by a protecting group (hereinafter, amino acid in which the α-amino group at the N-terminus is protected by a protecting group will be referred to as "protected amino acid") and protected amino acid whose side chain is bonded to the -L-Y group. In terms of synthesizing a labeling precursor that can be labeled more selectively, the labeling precursor preferably is synthesized using protected amino acid whose side chain is bonded to the -L-Y group and protected amino acid with the functional group of its side chain being protected by a protecting group. The synthesis of the labeling precursor preferably includes synthesizing the polypeptide represented by the amino acid sequence of the formula (1), removing protecting groups protecting functional groups of amino acid side chains in the synthesized polypeptide to which the -L-Y group is not bonded and that can be labeled, reprotecting the deprotected functional groups of the amino acids with protecting groups different from those removed, and removing protecting groups to deprotect functional groups of the amino acids other than those reprotected. When Y represents a hydrogen atom, the amino group at the end of the -L-Y group preferably is protected.

[Method for Producing Peptide Derivative]

Still another aspect of the present invention relates to a method for producing a peptide derivative, which includes labeling the labeling precursor of the present invention.

In the method for producing the peptide derivative of the present invention, in terms of allowing the production of the peptide derivative of the present invention with ease, preferably performing labeling in a short time, and moreover achieving excellent labeling yields, it is preferable that, in the labeling precursor represented by the formula (IV), Y is a hydrogen atom. Specifically, a peptide derivative represented by the following formula (VII) is preferred. With the production method according to this aspect, labeling can be performed in a short time, and moreover, excellent labeling yields can be achieved because the peptide derivative represented by the formula (VII) is used as the labeling precursor. Furthermore, with the production method according to this aspect, it is possible to preferably suppress labeling by-products. In the formula (VII), the polypeptide ExP-P, l and m are as described above.

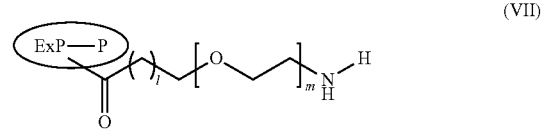

(VII)

For example, a labeling compound having the group represented by the formula (III) can be used to label the labeling precursor. The labeling compound having the group represented by the formula (III) preferably is a succinimidyl ester compound in which the group represented by the formula (III) is bonded to succinimide via ester bond, and more preferably, a succinimidyl ester compound represented by the following formula (VIII). In the succinimidyl ester compound represented by the formula (VIII), it is preferable that Ar, $R^2$, and $R^3$ represent a phenyl group, a hydrogen atom, and a bond, respectively, in terms of improving the affinity between the peptide derivative to be produced and pancreatic β-cells, preferably the affinity between the peptide derivative and GLP-1R of pancreatic β-cells; and it is more preferable that Ar, $R^1$, $R^2$, and $R^3$ represent a phenyl group, [$^{18}$F]fluorine atom or [$^{123/124/125/131}$I]Iodo atom, a hydrogen atom, and a bond, respectively. The labeling compound having the group represented by the formula (III) preferably is a compound represented by the following formula (VIIIa), and more preferably a compound represented by the following formula (VIIIb) ([$^{18}$F]N-succinimidyl 4-fluorobenzoate) and a compound represented by the following formula (VIIIc) ([$^{123/124/125/131}$I]N-succinimidyl 3-iodobenzoate). The labeling compound having the group represented by the formula (III) preferably is a compound represented by the following formula (VIIId) in terms of the general versatility.

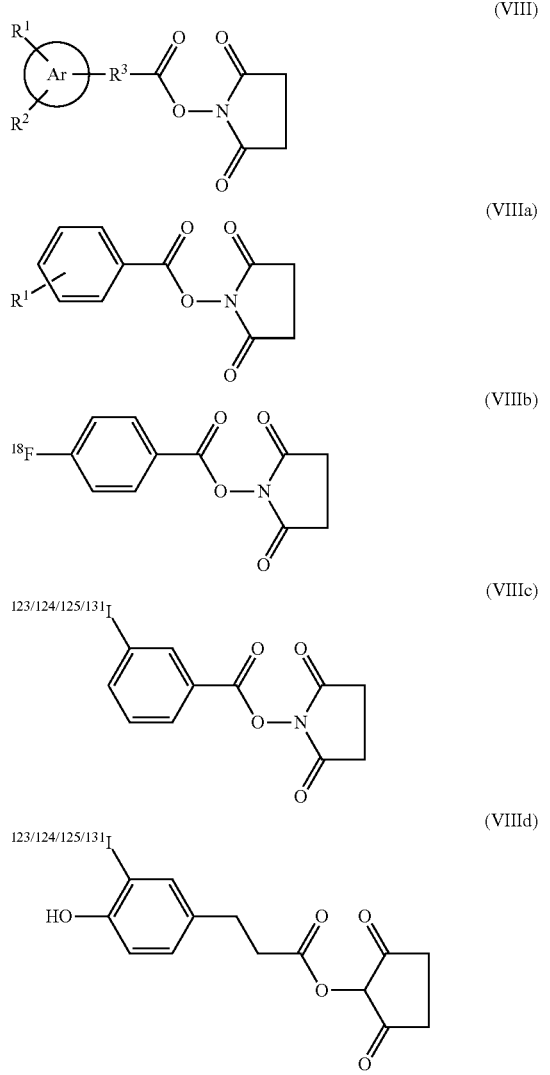

The method for producing the peptide derivative of the present invention may include removing protecting groups bonded to the labeled peptide derivative to deprotect the peptide derivative. The deprotection can be performed by way of a known method in accordance with the type of the protective groups.

In terms of producing a radioactively labeled peptide derivative with high purity, the method for producing the peptide derivative of the present invention may further include purifying the labeled peptide derivative. For the purifying, any known separation operation for purifying peptide or protein can be used, for example. Examples of separation operations include ion-exchange chromatography, hydrophobic chromatography, reversed-phase chromatography, and high-performance liquid chromatography (HPLC) and they can be used in combination as needed.

The method for producing the peptide derivative of the present invention may include synthesizing a labeling compound having the group represented by the formula (III) used in the labeling and/or synthesizing the labeling precursor. In this case, the synthesis of the labeling compound and the labeling of the labeling precursor can be performed using a single automatic synthesizing device or the synthesis of the labeling precursor, the synthesis of the labeling compound and the labeling of the labeling precursor can be performed using a single automatic synthesizing device.

Another aspect of the method for producing the peptide derivative of the present invention relates to a method for producing a peptide derivative, which includes labeling a labeling precursor in which Y in the formula (IV) represents a radioactive labeling introduction group. In the method for producing peptide according to this aspect, the labeling precursor may be, for example, a labeling precursor in which Y represents a chelating site or the group represented by the formula (VI). Examples of the labeling precursor in which Y represents the group represented by the formula (VI) include a labeling precursor represented by the following formula (IX). In the formula (IX), the polypeptide ExP-P, l, m and $R^4$ are as described above.

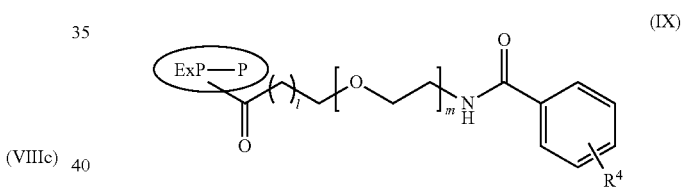

Examples of the labeling compound used in the labeling according to this aspect include compounds containing radioactive halogen nuclides such as [$^{18}$F]F$_2$, [$^{18}$F]KF, [$^{123/124/125/131}$I]NaI, and [$^{123/124/125/131}$I]NH$_4$I and compounds containing radioactive metal nuclides. A reaction used in the labeling is not particularly limited and electrophilic substitution, nucleophilic substitution, and the like can be used. Also in this aspect, the method may further include the deprotection process and/or the purifying process like the method described above.

[Reagent for Imaging]

Still another aspect of the present invention relates to a reagent for imaging, which contains the peptide derivative represented by the general formula (I).

The reagent for imaging according to the present invention contains, as an effective ingredient, the peptide derivative represented by the general formula (I), preferably a peptide derivative in which Z in the general formula (I) represents a labeling group containing a radionuclide in terms of performing PET and SPECT imaging.

The form of the reagent for imaging is not particularly limited, and the reagent may be in the form of a solution or powder, for example. When Z in the general formula (I) represents a labeling group containing a radionuclide, the reagent preferably is in the form of a solution, and more preferably in the form of a parenteral solution in terms of the half-life and radioactive decay of the radionuclide. When Z in the general formula (I) represents a labeling group containing a non-radioisotope of a radionuclide, the reagent may be in the form of a solution or powder. However, the reagent preferably is in the form of a powder, and more preferably in the form of a freeze-dried powder (freeze-dried formulation) in terms of the handling and the storage stability.

The reagent for imaging according to the present invention may contain medicinal additives such as a carrier. In the present specification, medicinal additives refer to compounds that have been approved as medicinal additives in the Japanese, US and/or European pharmacopoeia. Aqueous solvents and non-aqueous solvents can be used as the carrier. Examples of aqueous solvents include a potassium phosphate buffer solution, a physiological saline solution, a Ringer's solution, and distilled water. Examples of non-aqueous solvents include polyethylene glycol, vegetable oils, ethanol, glycerin, dimethylsulfoxide and propylene glycol.

[Kit]

Still another aspect of the present invention relates to a kit including the peptide derivative represented by the general formula (I) and/or the labeling precursor represented by the general formula (IV). Examples of embodiments of the kit include a kit for producing the peptide derivative of the present invention, a kit for imaging pancreatic β-cells, a kit for imaging GLP-1R of pancreatic β-cells, a kit for determining an amount of pancreatic islets, and a kit for prevention, treatment, or diagnosis of diabetes. Preferably, in each of these embodiments, the kit of the present invention includes an instruction manual suitable for each embodiment. The instruction manual may be packed with the kit or may be provided on the web.

The form of the peptide derivative represented by the general formula (I) is not particularly limited, and it may be in the form of solution or powder, for example. When Z in the general formula (I) represents a labeling group containing a radionuclide, the peptide derivative preferably is in the form of a parenteral solution in terms of the half-life and radioactive decay of the radionuclide. When Z in the general formula (I) represents a labeling group containing a non-radioisotope of a radionuclide, the peptide derivative may be in the form of a solution or powder. However, the peptide derivative preferably is in the form of a powder, and more preferably in the form of a freeze-dried powder (freeze-dried formulation) in terms of the handling and the storage stability.

The form of the labeling precursor represented by the general formula (IV) is not particularly limited, and it may be in the form of a solution or powder, for example. The labeling precursor preferably is in the form of a powder, and more preferably in the form of a freeze-dried powder (freeze-dried formulation) in terms of the handling.

The kit including the labeling precursor may contain a labeling compound used for labeling the labeling precursor, compounds to be starting materials of the labeling compound and other reagents used in radioactive labeling. The labeling compound is as described above. In particular, the compound represented by the formula (VIIIa) is preferred and the compound represented by the formula (VIIIb) and the compound represented by the formula (VIIIc) are more preferred. Examples of starting materials include starting materials of the labeling compound represented by the formula (VIIIb) and those of the labeling compound represented by the formula (VIIIc).

Examples of starting materials of the labeling compound represented by the formula (VIIIb) include ester derivatives of 4-(trimethylammonium triflate) benzoic acid. Examples of ester derivatives of 4-(trimethylammonium triflate) benzoic acid include methyl ester, ethyl ester, t-butyl ester and pentamethyl ester. Examples of other starting materials of the labeling compound represented by the formula (VIIIb) include ethyl 4-(trimethylammonium triflate) benzoate, ethyl 4-(tosyloxy)benzoate, and ethyl 4-(methylsulfonyloxy)benzoate. Examples of starting materials of the labeling compound represented by the formula (VIIc) include 2,5-dioxopyrrolidin-1-yl 3-(tributylstannyl)benzoate, 2,5-dioxopyrrolidin-1-yl 3-bromobenzoate, 2,5-dioxopyrrolidin-1-yl 3-chlorobenzoate and 2,5-dioxopyrrolidin-1-yl 3-iodobenzoate. Examples of other reagents used in radioactive labeling include reagents containing a radionuclide used for synthesizing the labeling compound.

The kit of the present invention further may include a container for containing the peptide derivative represented by the general formula (I) and/or the labeling precursor represented by the general formula (IV). Examples of the container include a syringe and a vial.

The kit of the present invention may further contain components for preparing a molecular probe, such as a buffer and an osmotic regulator, and an instrument used in administration of the peptide derivative, such as a syringe.

The kit including the labeling precursor may include, for example, an automatic synthesizing device for synthesizing the labeling compound. In addition to synthesizing the labeling compound, the automatic synthesizing device may also be capable of labeling the labeling precursor using the synthesized labeling compound, deprotecting the labeled peptide derivative, and synthesizing the labeling precursor.

[Method for Imaging]

Still another aspect of the present invention relates to a method for imaging pancreatic β-cells, which includes imaging pancreatic β-cells using the peptide derivative represented by the general formula (I). With the method for imaging of the present invention, it is possible to image pancreatic β-cells, preferably GLP-1R of pancreatic β-cells because the peptide derivative of the present invention is used. Examples of the analyte include humans and/or mammals other than humans. The peptide derivative preferably is a peptide derivative in which Z in the general formula (I) represents a labeling group containing a radionuclide.

The method for imaging of the present invention includes, as the first embodiment, detecting a signal of a radionuclide of the peptide derivative represented by the general formula (I) from an analyte to which the peptide derivative has been administered in advance. The signal preferably is detected after a lapse of sufficient time from the administration of the peptide derivative.

The method for imaging of the present invention may include, for example, reconfiguring the detected signal to convert the signal into an image, and displaying the image, and/or converting the detected signal into numbers and presenting an accumulation amount. Displaying includes, for example, displaying the image on a monitor and printing the same. Presenting includes, for example, storing the calculated accumulation amount and outputting the same to the outside.

The detection of the signal can be determined appropriately in accordance with the type of the radionuclide of the peptide derivative to be used, and PET and SPECT can be used to perform the detection. SPECT include, for example, determining, with use of a gamma camera, γ-rays emitted from an analyte to which the peptide derivative of the present invention has been administered. The determination with use of the gamma camera includes, for example, measuring radiation (γ-rays) emitted from the radionuclide of the peptide derivative during a certain time unit, and preferably includes determining a direction in which the radiation is emitted and a radiation dose during a certain time unit. The method for imaging of the present invention further may include presenting the determined distribution of the peptide derivative obtained by the measurement of the radiation as a cross-sectional image, and reconfiguring the obtained cross-sectional image.

PET include, for example, simultaneously measuring γ-rays generated upon annihilation of positrons with electrons, with use of a detector for PET, from an analyte to which the peptide derivative has been administered, and further may include figuring a three-dimensional distribution of positions of radionuclides emitting positrons, based on the measurement results.

The determination by means of X-ray CT and/or MRI may be performed, together with the determination by means of SPECT or PET. This makes it possible to obtain, for example, a fusion image obtained by fusion of an image obtained by SPECT or PET (functional image), with an image obtained by CT or MRI (morphological image).

The method for imaging of the present invention includes, as the second embodiment, administering the peptide derivative represented by the general formula (I) to an analyte and detecting a signal of a radionuclide of the peptide derivative from the analyte to which the peptide derivative has been administered. The detection of the signal and the reconfiguration can be performed in the same manner as in the first embodiment.

The administration of the peptide derivative to an analyte may be local administration or systemic administration. A path for administration may be determined appropriately according to a state of an analyte and the like, and it may be, for example, intravenous, intraarterial, intradermal, and intraabdominal injection or infusion. The administration amount (dosage) of the peptide derivative is not particularly limited and the peptide derivative may be administered in an enough amount to obtain a desired contrast for imaging, for example, not more than 1 µg. The peptide derivative preferably is administered with medicinal additives, such as a carrier. The medicinal additives are as described above. The time period from the administration to the determination may be decided appropriately according to, for example, a time that it takes for the molecular probe to be bound to pancreatic β-cells, the type of the molecular probe, the decomposition time of the molecular probe, etc.

The method for imaging according to the second embodiment may include determining a state of pancreatic islets or pancreatic β-cells based on the obtained image using the peptide derivative of the present invention. Determining a state of pancreatic islets or pancreatic β-cells includes, for example, determining the presence/absence of pancreatic islets or pancreatic β-cells and determining an increase/decrease in the amount of pancreatic islets by analyzing an image of the imaging of pancreatic β-cells.

[Method for Determining Amount of Pancreatic Islets]

Still another aspect of the present invention relates to a method for determining an amount of pancreatic islets using the peptide derivative represented by the general formula (I). The method for determining an amount of pancreatic islets according to the present invention preferably includes detecting a signal of the peptide derivative represented by the general formula (I) from an analyte to which the peptide derivative has been administered, and calculating an amount of the pancreatic islets from the detected signal of the peptide derivative. The peptide derivative preferably is a peptide derivative in which Z in the general formula (I) is a labeling group containing a radionuclide.

The calculation of the amount of pancreatic islets can be performed by, for example, analyzing the detected signal amount, and an image obtained by reconfiguration of the signal. Further, the quantification of a subject of the imaging from results of the imaging can be performed easily by any person skilled in the art, using a calibration curve, an appropriate program, or the like. The subject of imaging is, for example, pancreatic islets, preferably pancreatic β-cells, and more preferably GLP-1R of pancreatic β-cells. The method for determining an amount of pancreatic islets according to the present invention preferably is a method for determining an amount of pancreatic β-cells from the viewpoint of the application of the same to the examination and diagnosis.

The method for determining an amount of pancreatic islets according to the present invention further may include presenting the calculated amount of pancreatic islets. Presenting the calculated amount of pancreatic islets includes, for example, storing the calculated amount of pancreatic islets or outputting the same to the outside. Outputting the same to the outside includes, for example, displaying the same on a monitor and printing the same.

[Methods for Prevention, Treatment, and Diagnosis of Diabetes]

Still another aspect of the present invention relates to a method for prevention, treatment, or diagnosis of diabetes. As described above, in the diabetes developing process, the amount of pancreatic islets (particularly, the amount of pancreatic β-cells) decreases prior to the occurrence of glucose tolerance abnormalities, and therefore, when functional abnormalities are detected or there are subjective symptoms, diabetes has already reached the stage where it is too difficult to be treated. With the method for imaging using the peptide derivative of the present invention and/or the method for determining an amount of the pancreatic islets using the same, however, a decrease in the amount of the pancreatic islets and/or the amount of the pancreatic β-cells can be detected at an early stage, and further, new methods for prevention, treatment, and diagnosis of diabetes can be created. Examples of a subject (analyte) on which prevention, treatment, and diagnosis of diabetes is carried out include humans and/or mammals other than humans.

A method for diagnosis of diabetes according to the present invention includes: imaging of pancreatic β-cells with use of the peptide derivative of the present invention; and determining a state of the pancreatic islets based on the obtained image of the pancreatic islets and/or the obtained amount of the pancreatic islets; and further may include performing diagnosis of diabetes based on the determination results. The determination of a state of pancreatic islets includes, for example, determining an increase/decrease, or a change, in the amount of pancreatic islets by comparing the obtained image of pancreatic islets with an image of pancreatic islets as a reference, or comparing the obtained amount of pancreatic islets with an amount of pancreatic islets as a reference. Further, the determination of a state of pancreatic islets may be carried out using an information processing device. When it is determined that the amount of pancreatic islets has decreased, preferably this information is presented, and when it is determined that the amount of pancreatic islets has increased or has been maintained, preferably this information is presented. The diagnosis of diabetes on the basis of the determination results includes, for example, determining a risk of development of diabetes, judging it to be diabetes, and determining a degree of development of diabetes.

A method for treatment of diabetes of the present invention includes, in addition to imaging of pancreatic islets with use of the peptide derivative of the present invention and performing diagnosis of diabetes based on the results of the imaging, treating diabetes on the basis of the diagnosis. The imaging of pancreatic islets and the diagnosis of diabetes can be performed in the same manner as those in the method for diagnosis of diabetes according to the present invention. The method for treatment of diabetes may include evaluating an effect of treatment such as medication and diet performed on a subject, focusing on a change in an amount of pancreatic islets. Further, the method for treatment of diabetes of the present invention may include imaging pancreatic islets and/or determining an amount of pancreatic islets by the method of the present invention, and evaluating functional recovery of the pancreatic islets on the basis of the obtained image of the pancreatic islets and/or the determined amount of the pancreatic islets.

A method for prevention of diabetes of the present invention includes imaging of pancreatic islets with use of the peptide derivative of the present invention, and determining a state of pancreatic islets based on the results of the imaging so as to determine a risk of development of diabetes. The method for prevention of diabetes of the present invention may include, for example, regularly determining an amount of pancreatic islets, and checking presence/absence of a tendency of a decrease in the amount of pancreatic islets.

Still another preferable aspect of the present invention relates to a method for ultra-early diagnosis of diabetes. The method for ultra-early diagnosis of diabetes of the present invention may include, for example, imaging pancreatic islets and/or determining an amount of pancreatic islets in comprehensive or ordinary medical examination by the method of the present invention, and determining a state of the pancreatic islets on the basis of the obtained image of the pancreatic islets and/or the determined amount of the pancreatic islets.

[Other Applications]

The peptide derivative of the present invention has the amino acid sequence of exendin-4(1-39) (SEQ ID NO. 1) completely or partially. As described above, it is known that exendin-4(1-39) is an analog of GLP-1, and bonds to GLP-1R expressed on the pancreatic β-cell. Therefore, the peptide derivative of the present invention can be bonded to GLP-1R, preferably to GLP-1R in a specific manner. Thus, it can be used in, for example, the imaging and quantification of GLP-1R-positive cells, and diagnosis and treatment of diseases involving the expression of GLP-1R. With the present invention, it is possible to perform the imaging and quantification of GLP-1R-positive cells, like the imaging, quantification, and the like of the pancreatic cells, as well as to perform the diagnosis and/or treatment of the diseases involving the expression of GLP-1R. The disease involving the expression of GLP-1R is, for example, a neuroendocrine tumor (NET). Examples of the neuroendocrine tumor include insulinoma, small cell bronchial carcinoma, and pancreatic cancer.

Hereinafter, the present invention will be described further by way of Examples and Reference Examples. It should be noted that the present invention is, when interpreted, not limited to the following Examples.

In the description of the present specification, the following abbreviations are used.
IB: 3-iodobenzoyl
Rink Amide MBHA Resin (trade name, manufactured by Merck & Co., Inc): 4-(2',4'-Dimethoxyphenyl-Fmoc-aminomethyl)-phenoxyacetamido-norleucyl-MBA
HBTu: 1-[bis(dimethylamino)methylene]-1H-benzotriazolium-3-oxide-hexafluorophosphate
HOBt: 1-hydroxybenzotriazole
DMF: dimethyl formamide
Boc-mini-PEG-3™ (trade name, manufactured by Peptide International Inc):
Boc-11-Amino-3,6,9-trioxaundecanoic acid.DCHA
Boc: butoxy carbonyl group
DCHA: dicyclohexylamine
WSCD: water-soluble carbodiimide
TFA: tetrahydrofuran
HOSu: N-hydroxysuccinimide
IB-Cl: 3-iodobenzoyl chloride
DIEA: N,N-diisopropyl ethylamine
OBu: butyl ester group
Trt: trityl group
Pdf  2,2,4,6,7-pentamethyldihydrobenzofuran-5-sulfonyl group
Mmt: 4-methoxytrityl group
Fmoc: 9-fluorenylmethyloxycarbonyl group
PEG3: —C(O)—CH$_2$—(OC$_2$H$_4$)$_3$—NH—
ePEG12: —C(O)—C$_2$H$_4$—(OC$_2$H$_4$)$_{12}$—NH—
Note that amino acid in L-form was used unless mentioned otherwise.

EXAMPLES

Production Example 1

Synthesis of Peptide Derivative Represented by Formula (6): (IB-PEG$_3$)$_{12}$-Ex(9-39)

A peptide derivative represented by the following formula (6) (SEQ ID NO. 6) (hereinafter referred also to as "(IB-PEG$_3$)12-Ex(9-39)") was prepared as follows. In (IB-PEG$_3$) 12-Ex(9-39), [$^{125}$I]3-iodobenzoyl group ([$^{125}$I]IB) was bonded to, through PEG3 as a linker, the amino group of the side chain of the lysine residue at position 4 of the amino acid sequence of SEQ ID NO. 4 and the carboxyl group at the C-terminus was amidated.

(6)

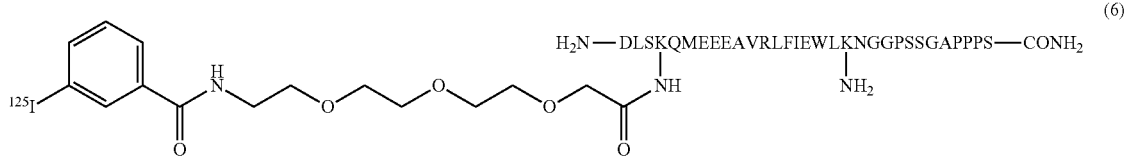

(1) Synthesis of Protected Peptide Resin A (SEQ ID NO. 7)
Fmoc-DLSK(Boc-PEG3)QMEEEAVRLFIEWLK(Fmoc)NGGPSSG
APPPS-Rink Amide MBHA (7)

A protected peptide resin A represented by the formula (7) was synthesized by solid phase synthesis using a peptide synthesizer (ACT90) manufactured by Advanced Chemtech.

In the formula (7), the protecting groups of the side chains other than Lys(Boc-PEG3) and Lys(Fmoc) are not recited.

Rink Amide MBHA Resin (0.39 mol/g, 0.25 mmol scale) was used as a starting resin carrier. Fmoc-amino acid derivatives used in a general Fmoc-peptide synthesis was used as raw materials of amino acids. Among the Fmoc-amino acid derivatives used, Asp(OBu), Ser(OBu), Gln(Trt), Glu(OBu), Trp(Boc), Arg(Pbf) and Asn(Trt) were used for the amino acids having functional groups at their side chain and Fmoc-Lys(Boc-PEG3) was used for the lysine at position 4 and Fmoc-Lys(Mmt) was used for the lysine at position 19. The Fmoc-amino acid derivatives as the raw materials were placed in the reaction container of the peptide synthesizer to dissolve them in HOBt and HBTu as activators and DMF, and put them in a reaction vessel to let them react with each other. The obtained resin was stirred gently in piperidine-containing N-methylpyrolidone to eliminate the Fmoc group. After rinsing, the next amino acid derivative condensation was performed, where peptide chains were extended one after another in accordance with the peptide sequence, and thus obtaining a protected peptide resin A1 represented by the following formula (8). Note that the protecting groups of the side chains other than Lys(Mmt) are not recited in the formula (8).

```
                                                    (SEQ ID NO. 8)
Fmoc-QMEEEAVRLFIEWLK(Mmt)NGGPSSGAPPPS-Rink Amide

MBHA (8)
```

Further, the amino acids were extended in accordance with the sequence using Fmoc-Lys(Boc-PEG3), Fmoc-Ser(OBu), Fmoc-Leu, and Fmoc-Asp(OBu) to obtain a protected peptide resin A2 represented by the following formula (9). Note that the protecting groups of the side chains other than Lys (Boc-PEG3) and Lys(Mmt) are not recited in the formula (9).

```
                                                    (SEQ ID NO. 9)
Fmoc-DLSK(Boc-PEG3)QMEEEAVRLFIEWLK(Mmt)NGGPSSGAP PPS-Rink Amide MBHA (9)
```

Subsequently, the protecting group (Mmt) of the side chain of Lys at position 19 of the protected peptide resin A2 was removed by TFA-TIS-DCM (1.5:5:93.5 v/v), and then the amino group of the side chain of Lys at position 19 was Fmoc-protected using FmocOsu, thus obtaining the protected peptide resin A represented by the formula (7).

The Fmoc-Lys(Boc-PEG3) was prepared as follows. Boc-mini-PEG-3™ was dissolved in THF and 0.5N of HCl/ethyl acetate was dropped thereto (pH: 3 to 5). After removing precipitated DCHA salt, the obtained Boc-PEG3 was converted to an activated ester body using WSCD.HCl and HOSu. The activated ester body and Fmoc-Lys were stirred in DMF at ambient temperature (pH: 7 to 8), and thus obtaining Fmoc-Lys(Boc-PEG3).

(2) Deprotection and Excision from Resin

The obtained protected peptide resin A was treated for 2 hours at ambient temperature under typical deprotection conditions using trifluoroacetate (TFA-TIS-H$_2$O-DT (95/2.5/2.5/2.5, v/v) to perform deprotection and excision of the peptide from the resin at the same time. After filtering the reaction solution to remove the carrier resin, TFA was distilled off. Ether was added to the residue to precipitate a crude product, and then the crude product was obtained by filteration.

(3) Isolation and Purification of Crude Peptide

The obtained crude peptide was fractionated and purified in a system of water-acetonitrile containing 0.1% of trifluoroacetate using a preparative high performance liquid chromatograph (HPLC) (trade name: LC-8A-2, manufactured by Shimadzu Corp, column: OSD 30×250 mm) to obtain intended peptide fractions. After distilling off the acetonitrile, the peptide fractions were made into the form of freeze-dried powder, and thus obtaining a peptide derivative represented by the following formula (10) (SEQ ID NO. 10) in the form of trifluoroacetate salt. The peptide derivative represented by the formula (10) was the labeling precursor of (IB-PEG$_3$)12-Ex (9-39).

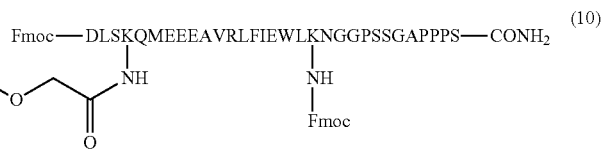

(4) Labeling of Labeling Precursor

Labeling was performed as follows. The peptide derivative represented by the formula (10) (410 µg) was dissolved in acetonitrile and a borate buffer (pH: 7.8), [$^{125}$I]N-succinimidyl 3-iodobenzoate ([$^{125}$I]SIB) was added thereto and the reaction solution was adjusted to have a pH of 8.5 to 9.0 and let them react with each other for 30 minutes. Thereafter, DMF and piperidine were added thereto to carry out a deprotection reaction, and thus obtaining intended (IB-PEG$_3$)12-Ex(9-39) (the peptide derivative represented by the formula (6)) (radiochemical yield: 48.6%, radiochemical purity: >99%). Further, the time involved in the labeling was 2.5 hours. Note that the time involved in the labeling refers to time until the intended labeled product was obtained by labeling the labeling precursor and the time includes the reaction time with the labeling compound, the deprotection reaction time after the reaction with the labeling compound, the LC purification time and the concentration time (the same applies to the following).

Reference Production Example 1

A peptide derivative represented by the following formula (11) was prepared. In the peptide derivative represented by the formula (11), [$^{125}$I]IB was directly bonded to the amino group of the side chain of the lysine residue at position 4 of the amino acid sequence of SEQ ID NO. 4 and the carboxyl group at the C-terminus was amidated.

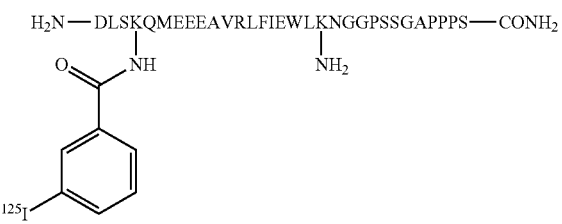

Labeling was performed in the same manner as in Production Example 1 except that a labeling precursor represented by the following formula (12) (1050 μg) was used in place of the peptide derivative represented by the formula (10), and 40-Ex(9-39), [$^{125}$I]IB was bonded to, through a PEG3 linker, the amino group of the side chain of the lysine residue at position 40 of the amino acid sequence of SEQ ID NO. 5 and the carboxyl group at the C-terminus was amidated.

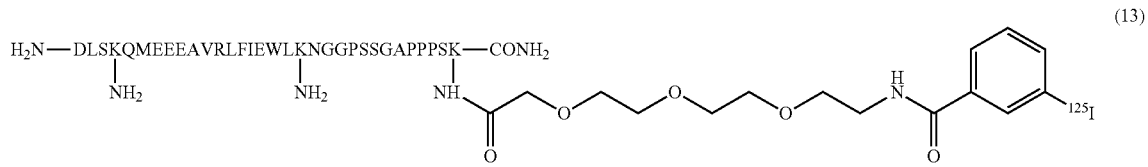

(13)

thus obtaining the intended peptide derivative represented by the formula (11) (radiochemical yield: 18.4%, radiochemical purity: 96.4%). The time involved in the labeling was 5.5 hours.

(SEQ ID NO. 12)
Fmoc-DLSKQMEEEAVRLFIEWLK(Fmoc)NGGPSSGAPPPS-CONH$_2$ (12)

As Production Example 1 and Reference Production Example 1 show, due to performing the radioactive labeling using the peptide derivative represented by the formula (10) in which PEG3 as a linker was bonded to the amino group of the side chain of the lysine, the yield of the radioactively labeled peptide derivative significantly improved and the time involved in the labeling was significantly reduced in comparison with the case of using the labeling precursor represented by the formula (12) in which PEG3 was not bonded to the amino group of the side chain of the lysine. Specifically, the yield was improved by twice or more, from 18.4% to 48.6%. Further, the time involved in the labeling was reduced by 3 hours, from 5.5 hours to 2.5 hours, so that the labeling was performed by half the conventional time. Therefore, with the labeling precursor of the present invention, labeling can be performed in an efficient manner, so that a radioactively labeled peptide derivative can be provided efficiently.

Production Example 2

Synthesis of Peptide Derivative Represented by Formula (13): (IB-PEG$_3$)40-Ex(9-39)

A peptide derivative represented by the following formula (13) (SEQ ID NO. 13) (hereinafter referred also to as "(IB-PEG$_3$)40-Ex(9-39)") was prepared as follows. In (IB-PEG$_3$)

First, a protected peptide resin B represented by the following formula (14) (SEQ ID NO. 14) was synthesized. The protected peptide resin B was synthesized in the same manner as in Production Example 1 except that Fmoc-Lys(Mmt) was used for lysines at positions 4 and 19 and Fmoc-Lys(Boc-PEG3) was used for lysine at position 32. Note that the protecting groups of the side chains other than Lys(Boc-PEG3) and Lys(Fmoc) are not recited in the formula (14).

(SEQ ID NO. 14)
Fmoc-DLSK(Fmoc)QMEEEAVRLFIEWLK(Fmoc)NGGPSSGAPPPSK
(Boc-PEG3)-Rink Amide MBHA (14)

In the same manner as in Production Example 1, the obtained protected peptide resin B was deprotected and excised from the resin. Also, a peptide derivative was isolated and purified. Thus, the peptide derivative represented by the following formula (15) was obtained in the form of trifluoroacetate salt (freeze-dried powder). The peptide derivative represented by the formula (15) was the labeling precursor of (IB-PEG$_3$)40-Ex(9-39).

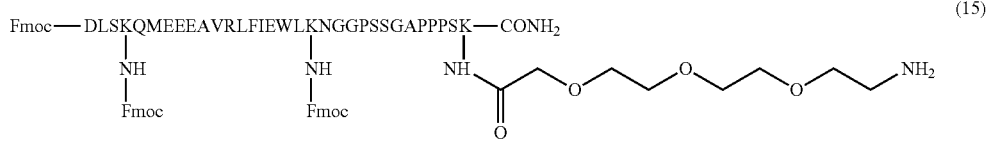

(15)

Then, the peptide derivative represented by the formula (15) (580 μg) was labeled and deprotected in the same manner as in Production Example 1, thus obtaining intended (IB-PEG$_3$)40-Ex(9-39) (the peptide derivative represented by the formula (11)) (radiochemical yield: 30.1%, radiochemical purity: 96.7%). The time involved in the labeling was 4 hours.

Reference Production Example 2

A peptide derivative represented by the following formula (16) (SEQ ID NO. 16) was prepared. In the peptide derivative represented by the formula (16), [$^{125}$I]IB was directly bonded to the amino group of the side chain of the lysine residue at position 32 of the amino acid sequence of SEQ ID NO. 5 and the carboxyl group at the C-terminus was amidated.

(16)

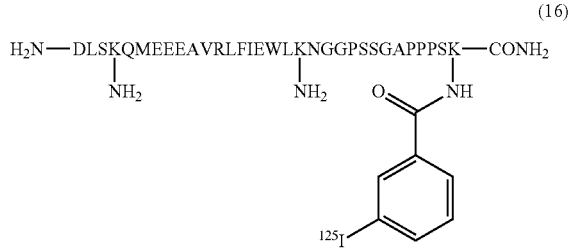

Labeling was performed in the same manner as in Production Example 1 except that a labeling precursor represented by the following formula (17) (400 μg) was used in place of the peptide derivative represented by the formula (10), thus obtaining the intended peptide derivative represented by the formula (16) (radiochemical yield: 33.6%, radiochemical purity: >99%). Further, the time involved in the labeling was 6 hours.

```
                                             (SEQ ID NO. 17)
Fmoc-DLSK(Fmoc)QMEEEAVRLFIEWLK(Fmoc)NGGPSSGAPPPSK-
CONH₂ (17)
```

Example 1

Biodistribution experiments and two-dimensional imaging analysis were performed using the peptide derivative represented by the formula (6) ((IB-PEG$_3$)12-Ex(9-39)).

[Biodistribution]

(IB-PEG$_3$)12-Ex(9-39) (0.93 μCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (IB-PEG$_3$)12-Ex(9-39) was calculated from the radioactivity per unit weight. The exemplary results are shown in Table 1 and FIG. 1. FIG. 1 is a graph showing, by way of example, how the accumulation of (IB-PEG$_3$)12-Ex(9-39) in each organ varied with time.

TABLE 1

| | Time after administration | | | | |
|---|---|---|---|---|---|
| | 5 min | 15 min | 30 min | 60 min | 120 min |
| Pancreas | 26.20 | 40.21 | 35.77 | 38.70 | 21.49 |
| | (5.96) | (7.72) | (5.23) | (6.09) | (7.71) |
| Blood | 8.35 | 4.35 | 2.64 | 1.55 | 0.68 |
| | (1.08) | (0.56) | (0.62) | (0.14) | (0.08) |
| Heart | 4.35 | 2.52 | 1.90 | 1.33 | 0.55 |
| | (0.61) | (0.40) | (0.34) | (0.30) | (0.18) |
| Lung | 85.31 | 110.66 | 77.81 | 70.41 | 45.36 |
| | (20.79) | (25.84) | (19.43) | (9.15) | (18.09) |
| Stomach | 3.77 | 4.77 | 9.52 | 11.87 | 8.74 |
| | (1.00) | (1.13) | (4.36) | (5.65) | (4.18) |
| Intestine | 2.83 | 3.47 | 6.12 | 11.58 | 10.74 |
| | (0.29) | (0.48) | (0.83) | (1.24) | (2.00) |
| Liver | 9.74 | 7.26 | 7.03 | 5.57 | 2.17 |
| | (0.93) | (0.69) | (0.65) | (0.96) | (0.38) |
| Spleen | 2.96 | 2.43 | 1.44 | 1.11 | 0.42 |
| | (0.46) | (0.62) | (0.11) | (0.15) | (0.06) |
| Kidney | 26.29 | 38.98 | 34.00 | 22.83 | 10.98 |
| | (2.64) | (9.27) | (2.23) | (4.76) | (2.61) |
| Thyroid gland | 5.24 | 2.89 | 2.05 | 2.63 | 2.93 |
| | (1.26) | (1.12) | (0.45) | (0.32) | (1.09) |

Each numerical value indicates an average (SD) of 5 mice.

As shown in Table 1 and FIG. 1, the accumulation of (IB-PEG$_3$)12-Ex(9-39) in the pancreas reached a level exceeding 25% dose/g at an early stage after the administration, and the accumulation was maintained at a high level thereafter. In particular, during the time period between 15 minutes and 60 minutes after the administration, the accumulation was greater than 35% dose/g. In terms of the accumulation per unit weight, (IB-PEG$_3$)12-Ex(9-39) accumulated the most in the pancreas other than the lung during the time period from 15 minutes after the administration. Further, no great change was seen in the accumulation of (IB-PEG$_3$)12-Ex(9-39) in the thyroid gland. This suggests that the peptide derivative was not subjected to deiodization metabolism in vivo. For these reasons, (IB-PEG$_3$)12-Ex(9-39) is considered suitable for noninvasive imaging, particularly noninvasive imaging of pancreatic β-cells.

Reference Example 1

Figure 2:
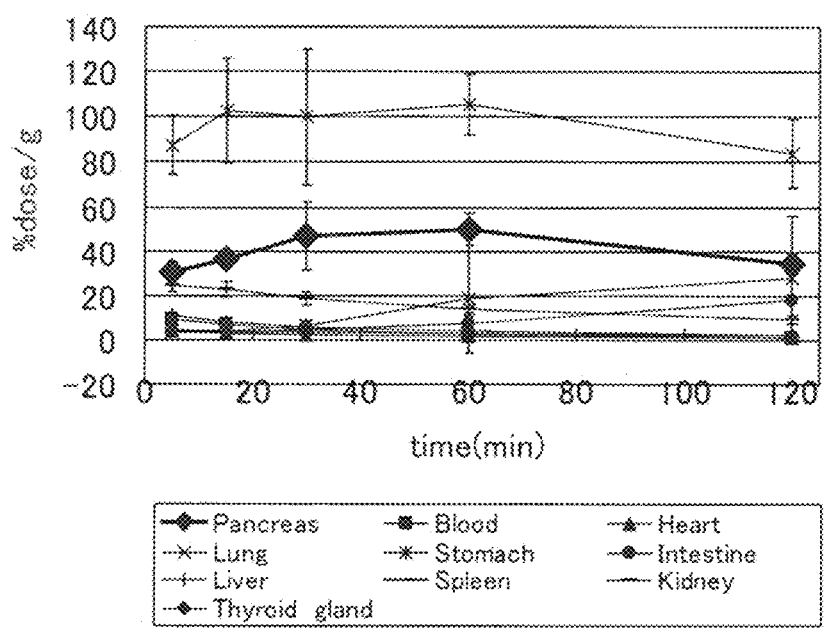
FIG. 2 is a graph showing exemplary time-variations of biodistribution of a peptide derivative of Reference Example 1.

As Reference Example 1, the peptide derivative represented by the formula (11) and prepared in Reference Production Example 1 was used to determine the biodistribution of the peptide derivative in mice in the same manner as in Example 1. The exemplary results are provided in Table 2 and FIG. 2.

TABLE 2

| | Time after administration | | | | |
|---|---|---|---|---|---|
| | 5 min | 15 min | 30 min | 60 min | 120 min |
| Pancreas | 30.26 | 36.10 | 46.87 | 49.94 | 34.36 |
| | (5.12) | (3.53) | (15.31) | (7.37) | (4.76) |
| Blood | 9.37 | 6.72 | 4.34 | 2.57 | 1.33 |
| | (0.26) | (0.98) | (0.77) | (0.28) | (0.20) |
| Heart | 4.89 | 3.42 | 2.39 | 1.87 | 0.99 |
| | (0.41) | (0.65) | (0.38) | (0.36) | (0.28) |
| Lung | 87.32 | 102.62 | 99.94 | 105.47 | 83.77 |
| | (13.16) | (23.24) | (30.05) | (13.68) | (15.02) |
| Stomach | 3.39 | 4.23 | 6.10 | 18.45 | 27.98 |
| | (1.37) | (0.53) | (2.34) | (24.20) | (27.99) |
| Intestine | 3.23 | 3.53 | 4.56 | 7.66 | 17.81 |
| | (0.44) | (0.72) | (0.51) | (3.41) | (19.02) |
| Liver | 11.34 | 8.03 | 5.83 | 3.74 | 2.22 |
| | (1.10) | (1.29) | (0.56) | (0.64) | (0.51) |
| Spleen | 4.14 | 3.03 | 2.37 | 1.61 | 0.85 |
| | (0.86) | (0.47) | (0.30) | (0.26) | (0.20) |
| Kidney | 24.77 | 23.02 | 18.58 | 13.92 | 9.14 |
| | (3.21) | (3.51) | (2.87) | (1.70) | (1.74) |
| Thyroid gland | 4.68 | 3.95 | 3.65 | 3.14 | 2.24 |
| | (0.98) | (0.54) | (0.62) | (1.31) | (0.60) |

Each numerical value indicates an average (SD) of 5 mice.

As shown Tables 1 and 2, in comparison with the peptide derivative represented by the formula (11), the peptide derivative represented by the formula (6) ((IB-PEG$_3$)12-Ex(9-30) accumulated less in the liver as an adjacent organ to the pancreas at an early stage after the administration as well as in blood.

Based on the accumulation amount in each organ during the biodistribution experiments in Example 1 and Reference Example 1, the ratio of pancreas/liver (accumulation amount in pancreas/accumulation amount in liver) for each peptide derivative is shown in Table 3, the ratio of pancreas/kidney (accumulation amount in pancreas/accumulation amount in kidney) for each peptide derivative is shown in Table 4, and the ratio of pancreas/blood (accumulation amount in pancreas/accumulation amount in blood) for each peptide derivative is shown in Table 5.

TABLE 3

Pancreas/Liver Ratio

| | Time after administration | | | | |
|---|---|---|---|---|---|
| | 5 min | 15 min | 30 min | 60 min | 120 min |
| Ex. 1 | 2.74 (0.84) | 5.61 (1.33) | 5.16 (1.12) | 7.00 (0.80) | 9.71 (1.94) |
| Ref. Ex. 1 | 2.67 (0.45) | 4.56 (0.62) | 8.16 (2.81) | 13.47 (1.51) | 15.95 (3.54) |

TABLE 4

Pancreas/Kidney Ratio

| | Time after administration | | | | |
|---|---|---|---|---|---|
| | 5 min | 15 min | 30 min | 60 min | 120 min |
| Ex. 1 | 0.99 (0.13) | 1.07 (0.28) | 1.06 (0.17) | 1.75 (0.47) | 1.99 (0.65) |
| Ref. Ex. 1 | 1.23 (0.19) | 1.60 (0.28) | 2.59 (1.01) | 3.61 (0.54) | 3.88 (0.94) |

TABLE 5

Pancreas/Blood Ratio

| | Time after administration | | | | |
|---|---|---|---|---|---|
| | 5 min | 15 min | 30 min | 60 min | 120 min |
| Ex. 1 | 3.19 (0.94) | 9.40 (2.29) | 14.57 (5.59) | 24.96 (2.96) | 31.08 (7.49) |
| Ref. Ex. 1 | 3.22 (0.47) | 5.44 (0.71) | 11.47 (4.97) | 19.49 (2.16) | 26.21 (4.42) |

As shown in Tables 3 and 4, the ratio of pancreas/liver and the ratio of pancreas/kidney for (IB-PEG$_3$)12-Ex(9-39) increased with time, and the ratio of pancreas/liver was greater than 2 at an early stage after the administration. As shown in Table 5, the ratio of pancreas/blood for (IB-PEG$_3$)12-Ex(9-39) increased remarkably with time in comparison with that for the peptide derivative represented by the formula (11). The ratio of pancreas/blood for (IB-PEG$_3$)12-Ex(9-39) was greater than 3 at an early stage after the administration, and showed a satisfactory blood clearance. Thus, the results suggest that clear images of pancreatic β-cells can be obtained when performing imaging using (IB-PEG$_3$)12-Ex(9-39), which accumulates in the pancreas in a large amount while accumulating less in the organs surrounding the pancreas and has an excellent blood clearance.

[Two-Dimensional Imaging Analysis]

(IB-PEG$_3$)12-Ex(9-39) (5 µCi/100 µl) was administered to an unanesthetized MIP-GFP mouse (male, weight: 20 g) by intravenous injection, and after 30 minutes and 60 minutes from the administration, the pancreas was dissected out of the mouse (n=1). Sections were cut out of the dissected pancreas, and each section was placed on a slide glass, covered with a cover glass. The fluorescence and the radioactivity (autoradiography) of each section were determined using an image analyzer (trade name: Typhoon 9410, manufactured by GE Health Care Inc.) (exposure time: 21 hours). The exemplary results are shown in lanes 3 to 8 of FIG. 3.

Further, non-labeled exendin(9-39) (cold probe, SEQ ID NO. 21) was administered preliminarily to unanesthetized MIP-GFP mice (male, weight: 20 g) by intravenous injection (50 µg/100 µl). After 30 minutes from the preliminary administration, (IB-PEG$_3$)12-Ex(9-39) (5 µCi/100 µl) was administered to the mice by intravenous injection, and after 30 minutes from the administration of (IB-PEG$_3$)12-Ex(9-39), the pancreases were dissected out of the mice (n=2). Sections were cut out of the dissected pancreases, and the fluorescence and the radioactivity of each section were determined in the same manner as in the above. The results are shown in lanes 1 and 2 of FIG. 3.

Figure 3:
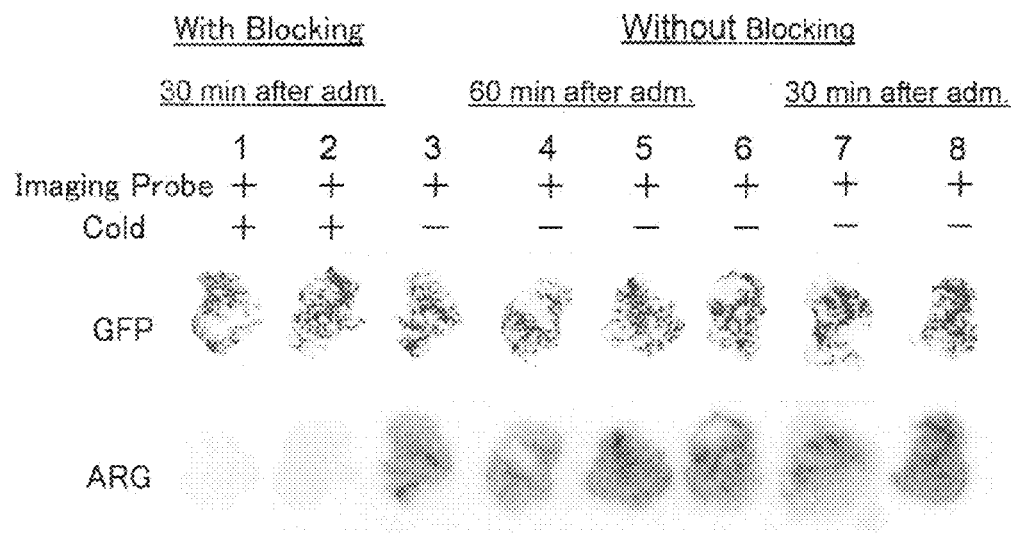
FIG. 3 shows images showing exemplary results of a two-dimensional imaging analysis using the peptide derivative of Example 1.

FIG. 3 illustrates exemplary results of the imaging analysis of the pancreas sections of the MIP-GFP mice to which (IB-PEG$_3$)12-Ex(9-39) was administered. The images shown therein are images showing a fluorescence signal (upper row) and a radioactivity signal (lower row) of (IB-PEG$_3$)12-Ex(9-39). In FIG. 3, the wording "with blocking" indicates that the results are of the case where the cold probe was administered prior to the administration of (IB-PEG$_3$)12-Ex(9-39) and the wording "without blocking" indicates that the results are of the case where (IB-PEG$_3$)12-Ex(9-39) was administered without preliminarily administering the cold probe.

Here, all of $^{125}$I, $^{123}$I, and $^{131}$I were γ-ray emitting nuclides. Still further, $^{125}$I and $^{123}$I have the same numbers of nuclear spins. In view of these, it can be presumed that even when (IB-PEG$_3$)12-Ex(9-39) is modified to replace its radioactive iodine atom with [$^{123}$I] iodine atom or [$^{131}$I] iodine atom, it will exhibit behaviors substantially identical to those of (IB-PEG$_3$)12-Ex(9-39). Further, it also can be presumed that even when (IB-PEG$_3$)12-Ex(9-39) is modified to replace its radioactive iodine atom with [$^{124}$I] iodine atom, it will exhibit behaviors substantially identical to those of (IB-PEG$_3$)12-Ex(9-39). Thus, it was suggested that using (IB-PEG$_3$)12-Ex(9-39) obtained by replacing its [$^{125}$I] iodine atom with [$^{123/124/131}$I] iodine atom, the noninvasive three-dimensional imaging of GLP-1R of pancreatic β-cells by SPECT, PET, or the like, for example, is enabled, and preferably, the quantification of GLP-1R of pancreatic β-cells is enabled.

Example 2

Three-dimensional SPECT imaging was performed using a peptide derivative represented by the following formula (18) (SEQ ID NO. 18) as follows. In the peptide derivative represented by the formula (18), [$^{123}$I]3-iodobenzoyl group ([$^{123}$I]IB) was bonded, through a PEG3 linker, to the amino group of the side chain of the lysine residue at position 4 of the amino acid sequence of SEQ ID NO. 4 and the carboxyl group at the C-terminus was amidated.

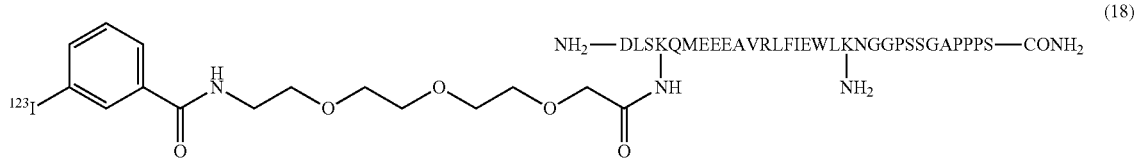

(18)

[Preparation of Peptide Derivative]

The peptide derivative represented by the formula (18) was prepared in the same manner as in Production Example 1 except that [$^{123}$I]SIB was used in place of [$^{125}$I] SIB.

[Three-Dimensional Imaging]

With use of the peptide derivative represented by the formula (18), SPECT imaging of mice was performed. The peptide derivative represented by the formula (18) (491 µCi (18.2 MBq)/120 µl) was administered to 6-week-old ddY mice (male, weight: about 30 g) by intravenous injection, and then after 20 minutes from the administration of the peptide derivative the mice were subjected to inhalation anesthesia with enflurane. And after 30 minutes from the administration of the peptide derivative, the SPECT imaging was performed under the following imaging conditions with use of a gamma camera (product name: SPECT 2000H-40, manufactured by Hitachi Medical Corporation). Images obtained were reconfigured under the following reconfiguration condition.

Imaging Conditions
Collimator: LEPH collimator
Collecting range: 360°
Step angle: 11.25°
Collecting time: 60 sec per direction
  1×32 frames per 60 sec (total: 32 min)
Reconfiguration Condition
Preprocessing filter: Butterworth filter (order: 10, cutoff frequency: 0.10)

Figure 4:
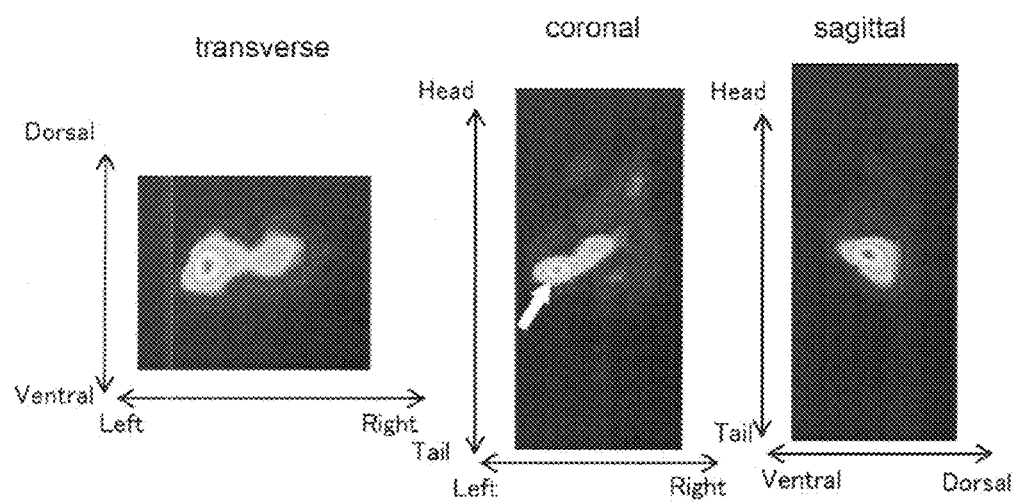
FIG. 4 shows images showing exemplary results of SPECT imaging using a peptide derivative of Example 2.

The exemplary results are shown in FIG. 4. The images shown in FIG. 4 were taken after 30 minutes from the administration of the peptide derivative. Shown in FIG. 4 are, starting from the left, a transverse view, a coronal view and a sagittal view. In the coronal view of FIG. 4, the position of the pancreas is indicated by a while arrow.

As shown in FIG. 4, the position of the pancreas was confirmed noninvasively in mice as a result of the SPECT imaging using the peptide derivative represented by the formula (18). Thus, in view of that the position of the pancreas was confirmed noninvasively in a mouse that has the pancreas in a smaller size than that of a human and in which the organs are present more densely than in a human, this suggests that in a human that has the pancreas in a greater size than that of a mouse and in which the organs are present not as densely as in a mouse, the position of the pancreas and the size of the pancreas can be determined more clearly, and moreover, an amount of the peptide derivative bonding to GLP-1R of pancreatic β-cells can be determined.

These results suggest that the peptide derivative of the present invention allows noninvasive three-dimensional imaging of pancreatic islets, particularly three-dimensional imaging of pancreatic β-cells or noninvasive three-dimensional imaging of GLP-1R of pancreatic β-cells, in a human.

Example 3

Biodistribution experiments and two-dimensional imaging analysis were performed using the peptide derivative represented by the formula (13) ((IB-PEG$_3$)40-Ex(9-39)).

[Biodistribution]

Figure 5:
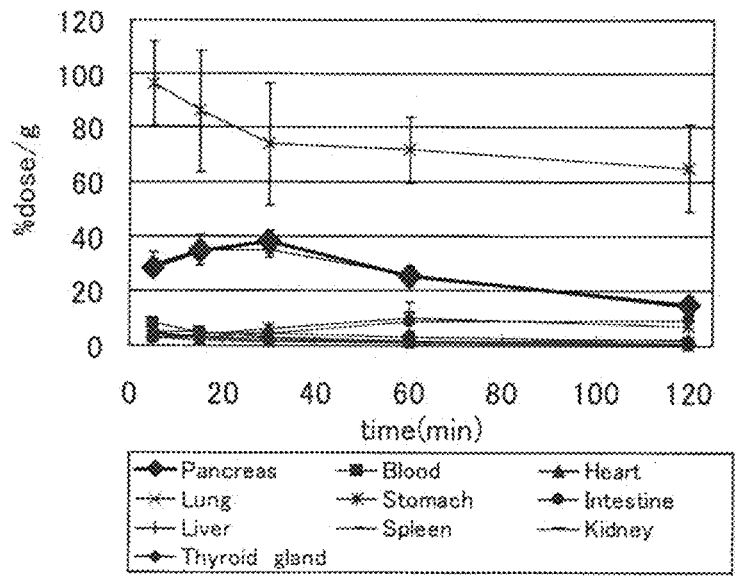
FIG. 5 is a graph showing exemplary time-variations of biodistribution of a peptide derivative of Example 3.

(IB-PEG$_3$)40-Ex(9-39) (0.69 µCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (IB-PEG$_3$)40-Ex(9-39) was calculated from the radioactivity per unit weight. The exemplary results are shown in Table 6 and FIG. 5. FIG. 5 is a graph showing, by way of example, how the accumulation of (IB-PEG$_3$)40-Ex(9-39) in each organ varied with time.

TABLE 6

| | Time after administration | | | | |
|---|---|---|---|---|---|
| | 5 min | 15 min | 30 min | 60 min | 120 min |
| Pancreas | 28.67 | 34.58 | 37.93 | 25.46 | 14.84 |
| | (2.94) | (3.02) | (4.22) | (3.66) | (3.10) |
| Blood | 8.15 | 4.80 | 3.19 | 1.80 | 0.93 |
| | (1.13) | (0.40) | (0.32) | (0.29) | (0.07) |
| Heart | 4.43 | 2.70 | 1.86 | 1.11 | 0.61 |
| | (0.60) | (0.51) | (0.26) | (0.24) | (0.10) |
| Lung | 96.22 | 86.15 | 73.84 | 71.65 | 64.92 |
| | (15.76) | (22.61) | (22.41) | (12.12) | (16.02) |
| Stomach | 3.24 | 4.08 | 5.96 | 10.17 | 6.99 |
| | (0.74) | (1.57) | (1.66) | (5.71) | (4.24) |
| Intestine | 2.65 | 2.99 | 4.45 | 8.81 | 9.13 |
| | (0.45) | (0.89) | (0.97) | (3.51) | (2.36) |
| Liver | 5.39 | 4.76 | 4.53 | 2.99 | 1.64 |
| | (0.46) | (0.56) | (0.16) | (0.42) | (0.14) |
| Spleen | 3.05 | 1.91 | 1.24 | 0.81 | 0.42 |
| | (0.50) | (0.24) | (0.10) | (0.14) | (0.07) |
| Kidney | 29.83 | 35.04 | 35.15 | 25.89 | 14.03 |
| | (4.46) | (5.69) | (2.65) | (2.31) | (2.84) |
| Thyroid gland | 4.61 | 3.04 | 2.51 | 1.29 | 2.07 |
| | (1.97) | (0.48) | (1.06) | (0.67) | (0.91) |

Each numerical value indicates an average (SD) of 5 mice.

As shown in Table 6 and FIG. 5, the accumulation of (IB-PEG$_3$)40-Ex(9-39) in the pancreas reached a level exceeding 25% dose/g at an early stage after the administration, and the accumulation was maintained at a high level thereafter. Further, no great change was seen in the accumulation of (IB-PEG$_3$)40-Ex(9-39) in the thyroid gland. This suggests that the peptide derivative was not subjected to deiodization metabolism in vivo. For these reasons, (IB-PEG$_3$)40-Ex(9-39) is considered suitable for noninvasive imaging, particularly noninvasive imaging of GLP-1R of pancreatic β-cells.

Reference Example 2

Figure 6:
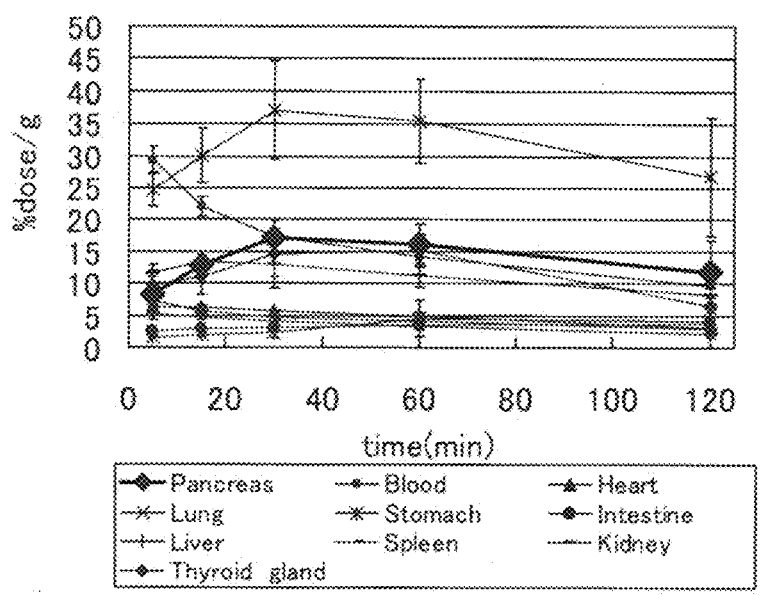
FIG. 6 is a graph showing exemplary time-variations of biodistribution of a peptide derivative of Reference Example 2.

As Reference Example 2, the peptide derivative represented by the formula (16) and produced in Reference Production Example 2 was used to determine the biodistribution of the peptide derivative in mice in the same manner as in Example 2. The exemplary results are provided in Table 7 and FIG. 6.

TABLE 7

| | Time after administration | | | | |
|---|---|---|---|---|---|
| | 5 min | 15 min | 30 min | 60 min | 120 min |
| Pancreas | 8.28 | 12.80 | 17.20 | 16.18 | 11.82 |
| | (0.96) | (1.49) | (1.22) | (3.03) | (5.00) |
| Blood | 29.39 | 21.99 | 17.24 | 14.10 | 9.62 |
| | (2.05) | (1.54) | (0.91) | (1.41) | (1.82) |
| Heart | 6.28 | 6.27 | 5.71 | 4.99 | 3.10 |
| | (0.37) | (0.45) | (0.20) | (0.56) | (0.52) |
| Lung | 24.64 | 30.00 | 37.09 | 35.52 | 26.83 |
| | (2.51) | (4.21) | (7.49) | (6.50) | (9.26) |
| Stomach | 1.61 | 2.06 | 2.29 | 4.62 | 4.23 |
| | (0.10) | (0.32) | (0.77) | (2.89) | (2.28) |
| Intestine | 2.57 | 2.90 | 3.06 | 3.59 | 3.77 |
| | (0.35) | (0.29) | (0.23) | (0.80) | (1.81) |
| Liver | 7.29 | 5.73 | 4.64 | 4.04 | 2.93 |
| | (0.75) | (0.49) | (0.81) | (0.55) | (0.83) |
| Spleen | 5.41 | 4.71 | 4.08 | 3.32 | 2.18 |
| | (0.98) | (0.45) | (0.36) | (0.46) | (0.54) |

TABLE 7-continued

| | Time after administration | | | | |
|---|---|---|---|---|---|
| | 5 min | 15 min | 30 min | 60 min | 120 min |
| Kidney | 11.57 | 13.39 | 12.92 | 11.14 | 8.22 |
| | (0.51) | (0.56) | (1.96) | (1.75) | (2.18) |
| Thyroid gland | 9.61 | 11.07 | 14.63 | 15.17 | 6.55 |
| | (3.36) | (2.78) | (5.30) | (2.54) | (2.83) |

Each numerical value indicates an average (SD) of 5 mice.

As shown in Tables 6 and 7, in comparison with the peptide derivative represented by the formula (16), the accumulation of the peptide derivative represented by the formula (13) ((IB-PEG$_3$)40-Ex(9-39)) in the pancreas was extremely large while the accumulation in the liver as an adjacent organ to the pancreas was small. Consequently, (IB-PEG$_3$)40-Ex(9-39) is considered to have excellent organ specificity to the pancreas in comparison with the peptide derivative represented by the formula (16).

Based on the accumulation amount in each organ during the biodistribution experiments in Example 3 and Reference Example 2, the ratio of pancreas/liver for each peptide derivative is shown in Table 8, the ratio of pancreas/kidney for each peptide derivative is shown in Table 9, and the ratio of pancreas/blood for each peptide derivative is shown in Table 10.

TABLE 8

Pancreas/Liver Ratio

| | Time after administration | | | | |
|---|---|---|---|---|---|
| | 5 min | 15 min | 30 min | 60 min | 120 min |
| Ex. 3 | 5.34 | 7.34 | 8.37 | 8.65 | 9.04 |
| | (0.51) | (1.02) | (0.94) | (1.84) | (1.72) |
| Ref. Ex. 2 | 1.15 | 2.25 | 3.80 | 4.01 | 3.99 |
| | (0.24) | (0.32) | (0.70) | (0.56) | (1.18) |

TABLE 9

Pancreas/Kidney Ratio

| | Time after administration | | | | |
|---|---|---|---|---|---|
| | 5 min | 15 min | 30 min | 60 min | 120 min |
| Ex. 3 | 0.98 | 1.01 | 1.09 | 0.99 | 1.09 |
| | (0.18) | (0.21) | (0.19) | (0.20) | (0.32) |
| Ref. Ex. 2 | 0.72 | 0.96 | 1.36 | 1.46 | 1.39 |
| | (0.08) | (0.12) | (0.27) | (0.20) | (0.31) |

TABLE 10

Pancreas/Blood Ratio

| | Time after administration | | | | |
|---|---|---|---|---|---|
| | 5 min | 15 min | 30 min | 60 min | 120 min |
| Ex. 3 | 3.57 | 7.24 | 12.07 | 14.49 | 15.85 |
| | (0.58) | (0.82) | (2.29) | (3.54) | (2.46) |
| Ref. Ex. 2 | 0.28 | 0.58 | 1.00 | 1.14 | 1.22 |
| | (0.04) | (0.08) | (0.08) | (0.15) | (0.45) |

As shown in Table 8, the results show that the ratio of pancreas/liver for (IB-PEG$_3$)40-Ex(9-39) was greater than 5 at an early stage after the administration. In particular, during the time period between 5 minutes and 30 minutes after the administration, the ratio of pancreas/liver for (IB-PEG$_3$)40-Ex(9-39) was more than 5 times as much as the ratio of pancreas/liver for the peptide derivative represented by the formula (16). Further, as shown in Table 9, the ratio of pancreas/kidney for (IB-PEG$_3$)40-Ex(9-39) reached approximately 1 at an early stage after the administration. As shown in Table 10, the ratio of pancreas/blood for (IB-PEG$_3$)40-Ex (9-39) was extremely higher than that for the peptide derivative represented by the formula (16), was greater than 3.5 at an early stage after the administration, and showed a satisfactory blood clearance. Thus, the results suggest that clear images of pancreatic β-cells can be obtained when performing imaging using (IB-PEG$_3$)40-Ex(9-39), which accumulates in the pancreas in a large amount while accumulating less in the organs surrounding the pancreas and has an excellent blood clearance.

[Two-Dimensional Imaging Analysis]

(IB-PEG$_3$)40-Ex(9-39) (5 μCi/100 μl) was administered to an unanesthetized MIP-GFP mouse (male, weight: 20 g) by intravenous injection, and after 30 minutes and 60 minutes from the administration, the pancreas was dissected out of the mouse (n=1). Sections were cut out of the dissected pancreas, and each section was placed on a slide glass, covered with a cover glass. The fluorescence and the radioactivity (autoradiography) of each section were determined using an image analyzer (trade name: Typhoon 9410, manufactured by GE Health Care Inc.) (exposure time: 19 hours). The exemplary results are shown in lanes 3, 4, 7 and 8 of FIG. 7.

Further, non-labeled exendin(9-39) (cold probe, SEQ ID NO. 20) was administered preliminarily to an unanesthetized MIP-GFP mouse (male, weight: 20 g) by intravenous injection (50 μg/100 μl). After 30 minutes from the preliminary administration, (IB-PEG$_3$)40-Ex(9-39) (5 μCi/100 μl) was administered to the mouse by intravenous injection, and after 30 minutes from the administration of (IB-PEG$_3$)40-Ex(9-39), the pancreas was dissected out of the mouse (n=1). Sections were cut out of the dissected pancreas, and the fluorescence and the radioactivity of each section were determined in the same manner as above. The exemplary results are shown in lanes 1, 2, 5 and 6 of FIG. 7.

Figure 7:
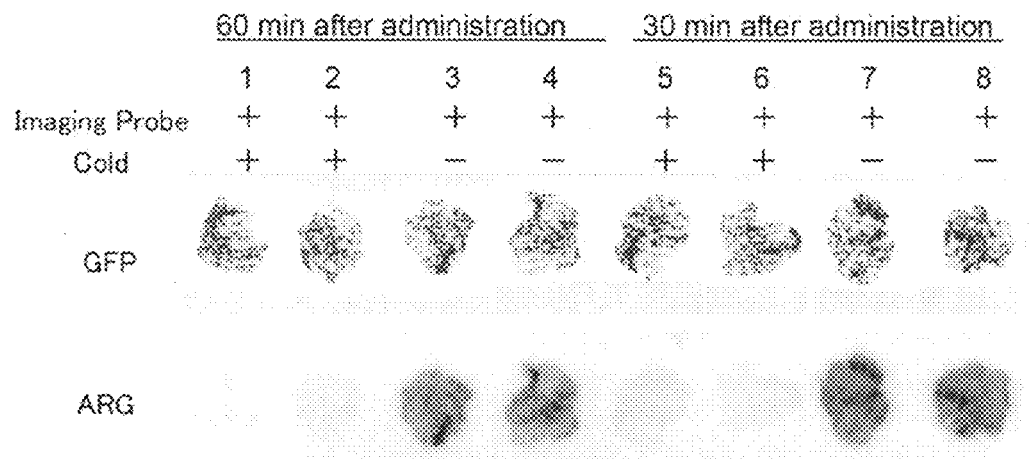
FIG. 7 shows images showing exemplary results of a two-dimensional imaging analysis using the peptide derivative of Example 3.

FIG. 7 illustrates exemplary results of the imaging analysis of the pancreas sections of the MIP-GFP mice to which (IB-PEG$_3$)40-Ex(9-39) was administered. The images shown therein are images showing a fluorescence signal (upper row) and a radioactivity signal (lower row) of (IB-PEG$_3$)40-Ex(9-39). In FIG. 7, the wording "with blocking" indicates that the results are of the case where the cold probe was administered prior to the administration of (IB-PEG$_3$)40-Ex(9-39) and the wording "without blocking" indicates that the results are of the case where (IB-PEG$_3$)40-Ex(9-39) was administered without preliminarily administering the cold probe.

From the results described above, it was suggested that, similarly to (IB-PEG$_3$)12-Ex(9-39), use of (IB-PEG$_3$)40-Ex (9-39) obtained by replacing its [$^{125}$I] iodine atom with [$^{123/124/131}$I] iodine atom allows, for example, the noninvasive three-dimensional imaging of GLP-1R of pancreatic β-cells by SPECT, PET, or the like preferably, the quantification of GLP-1R of pancreatic β-cells.

Example 4

Three-dimensional SPECT imaging was performed using a peptide derivative represented by the following formula (19) (SEQ ID NO. 19) as follows. In the peptide derivative represented by the formula (19), [$^{123}$I]3-iodobenzoyl group ([$^{123}$I]IB) was bonded, through a PEG3 linker, to the amino group of the side chain of the lysine residue at position 32 of the amino acid sequence of SEQ ID NO. 5 and the carboxyl group at the C-terminus was amidated.

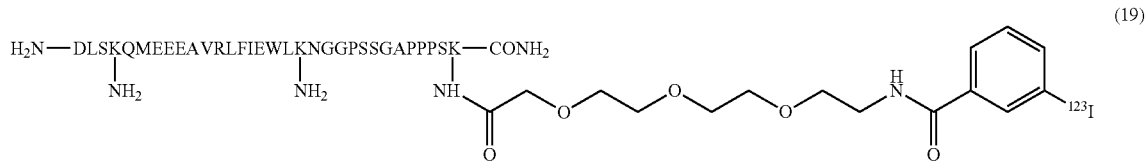

(19)

[Preparation of Peptide Derivative]

The peptide derivative represented by the formula (19) was prepared in the same manner as in Production Example 2 except that [$^{123}$I]SIB was used in place of [$^{125}$I] SIB.

[Three-Dimensional Imaging]

With use of the peptide derivative represented by the formula (19), SPECT imaging of mice was performed. The peptide derivative represented by the formula (18) (500 µCi (18.2 MBq)) was administered to 6-week-old ddY mice (male, weight: about 30 g) by intravenous injection, and then after 20 minutes from the administration of the peptide derivative the mice were subjected to inhalation anesthesia with enflurane. And after 30 minutes from the administration of the peptide derivative, the SPECT imaging was performed under the following imaging conditions with use of a gamma camera (product name: SPECT 2000H-40, manufactured by Hitachi Medical Corporation). Images obtained were reconfigured under the following reconfiguration condition.

Imaging Conditions
Collimator: LEPH collimator
Collecting range: 360°
Step angle: 11.25°
Collecting time: 60 sec per direction
1×32 frames per 60 sec (total: 32 min)
Reconfiguration Condition
Preprocessing filter: Butterworth filter (order: 10, cutoff frequency: 0.14)

Figure 8:
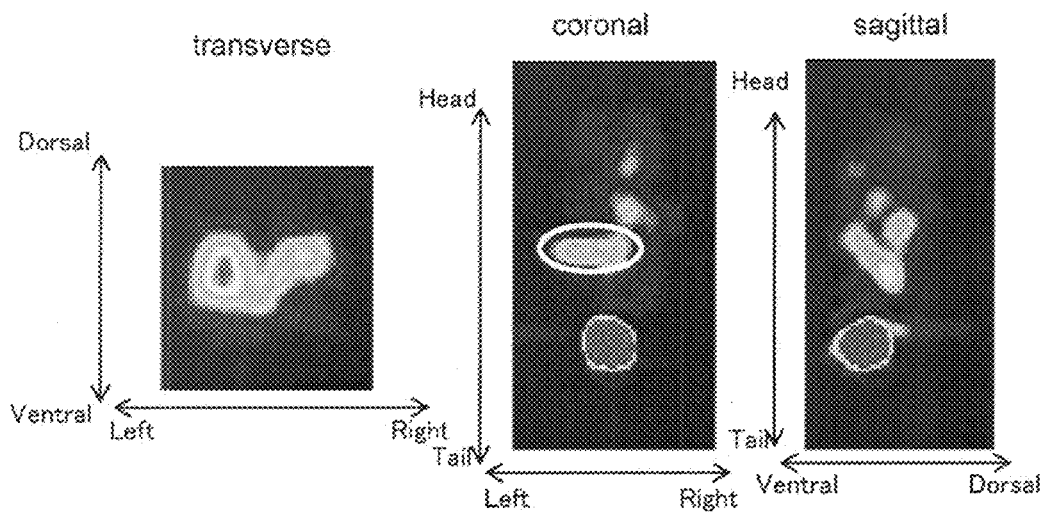
FIG. 8 shows images showing exemplary results of SPECT imaging using a peptide derivative of Example 4.

The exemplary results are shown in FIG. 8. The images shown in FIG. 8 were taken after 30 minutes from the administration of the peptide derivative. Shown in FIG. 8 are, starting from the left, a transverse view, a coronal view and a sagittal view. In the coronal view of FIG. 8, the portion circled with a white line indicates the position of the pancreas.

As shown in FIG. 8, the position of the pancreas was confirmed noninvasively in mice as a result of the SPEC imaging using the peptide derivative represented by the formula (19). Thus, in view of that the position of the pancreas was confirmed noninvasively in a mouse that has the pancreas in a smaller size than that of a human and in which the organs are present more densely than in a human, this suggests that in a human that has the pancreas in a greater size than that of a mouse and in which the organs are present not as densely as in a mouse, the position of the pancreas and the size of the pancreas can be determined more clearly, and moreover, an amount of the peptide derivative bonding to GLP-1R of pancreatic β-cells can be determined.

These results suggest that the peptide derivative of the present invention allows noninvasive three-dimensional imaging of pancreatic islets, particularly three-dimensional imaging of pancreatic β-cells or noninvasive three-dimensional imaging of GLP-1R of pancreatic β-cells, in a human.

Production Example 3

Synthesis of Peptide Derivative Represented by Formula (21): (FB-PEG$_3$)12-Ex4

A peptide derivative represented by the following formula (21) (SEQ ID NO. 21) (hereinafter referred also to as "(FB-PEG$_3$)12-Ex4") was prepared.

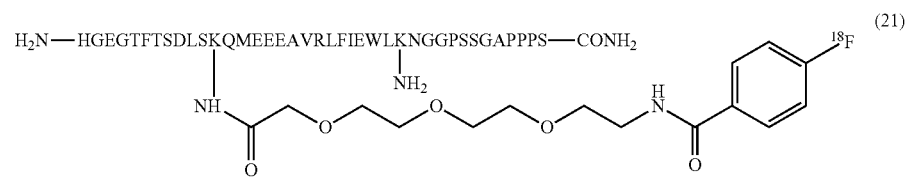

(21)

First, a peptide derivative represented by the following formula (22) (SEQ ID NO. 22, labeling precursor) was prepared using the same procedure as (1) to (3) of Production Example 1 except that the amino acid sequence of exendin4 (SEQ ID NO. 1) was adopted as the base sequence of the peptide to be synthesized.

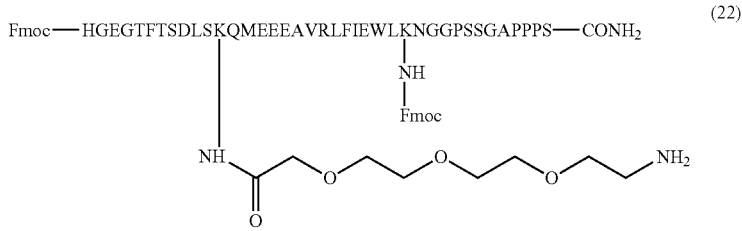

(22)

Next, labeling was performed as follows. The peptide derivative represented by the formula (22) (470 μg) was dissolved in a borate buffer (pH: 7.8), [$^{18}$F]N-succinimidyl 4-fluorobenzoate ([$^{18}$F]SFB) was added thereto and the reaction solution was adjusted to have a pH of 8.5 to 9.0 and let them react with each other for 40 minutes. Thereafter, DMF and piperidine were added thereto to carry out a deprotection reaction, and thus obtaining intended (FB-PEG$_3$)12-Ex4 (the peptide derivative represented by the formula (20)) (radiochemical yield: 10.0%, radiochemical purity: >99%). Further, the time involved in the labeling was 2 hours.

Reference Production Example 3

Labeling was performed in the same manner as in Production Example 3 except that a labeling precursor represented by the following formula (23) (220 μg) was used in place of the peptide derivative represented by the formula (22) and the reaction time with [$^{18}$F]SFB was changed to 73 minutes, thus obtaining intended peptide derivative represented by the formula (24) (SEQ ID NO. 24) (radiochemical yield: 1.3%, radiochemical purity: >99%). Further, the time involved in the labeling was 2.9 hours.

(SEQ ID NO. 23)
Fmoc-HGEGTFTSDLSKQMEEEAVRLFIEWLK(Fmoc)NGGPSSGAPPPS-CONH$_2$ (23)

peptide derivative (labeling precursor) in which PEG3 was bonded to the amino group of the side chain of Lys12, the yield of the radioactively labeled peptide derivative improved by seven times or more and the time involved in the labeling was reduced by approximately one hour in comparison with the labeling precursor of the formula (23) in which PEG3 was not bonded to the amino group of the side chain of the lysine. Therefore, with the labeling precursor of the present invention, it is possible to produce a peptide derivative that is radioactively labeled in an efficient manner.

Production Example 4

Synthesis of Peptide Derivative Represented by Formula (25): (IB-PEG$_3$)12-Ex4

Labeling was performed in the same manner as in (4) of Production Example 1 except that the peptide derivative represented by the formula (22) (240 μg) was used as the labeling precursor in place of the peptide derivative represented by the formula (10), thus obtaining intended (IB-PEG$_3$)12-Ex4 (a peptide derivative represented by the formula (25), (SEQ ID NO. 25)) (radiochemical yield: 18.7%, radiochemical purity: >95.1%). Further, the time involved in the labeling was 3.5 hours. Note that the time involved in the labeling includes the reaction time with the labeling compound, the HPLC purification time, the deprotection reaction time after the reaction

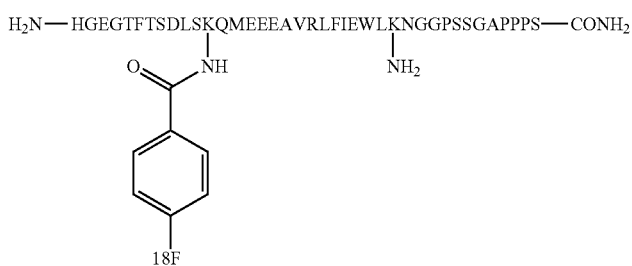

(24)

As Production Example 3 and Reference Production Example 3 show, as a result of radioactively labeling the with the labeling compound, the LC purification time and the concentration time.

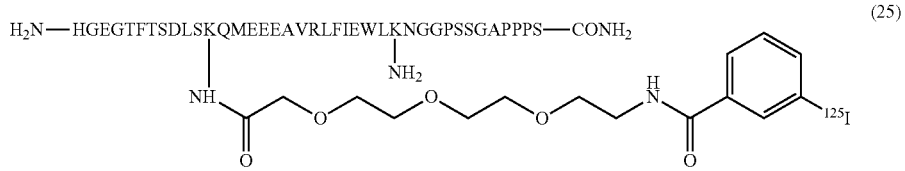

(25)

Reference Production Example 4

Labeling was performed in the same manner as in Production Example 4 except that the labeling precursor represented by the formula (23) (570 μg) was used in place of the peptide derivative represented by the formula (22) and the reaction time with [$^{125}$I]SIB was changed to 174 minutes, thus obtaining an intended peptide derivative represented by the formula (26) (SEQ ID NO. 26) (radiochemical yield: 18.4%, radiochemical purity: >97.2%). Further, the time involved in the labeling was 4.6 hours.

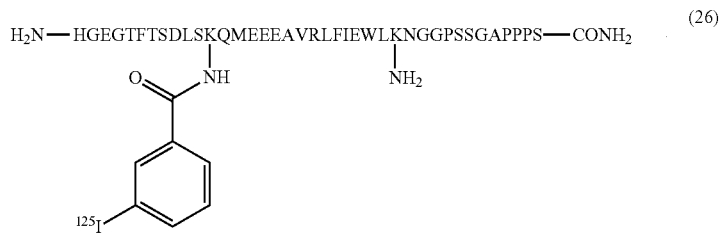

As Production Example 4 and Reference Production Example 4 show, as a result of radioactively labeling the peptide derivative of the formula (22) in which PEG3 was bonded to the amino group of the side chain of Lys12, the purity of the radioactively labeled peptide derivative obtained was improved and the time involved in the labeling was reduced by 1.1 hours in comparison with the case of using the labeling precursor of the formula (23) in which PEG3 was not bonded to the amino group of the side chain of the lysine.

Production Example 5

Synthesis of Peptide Derivative Represented by Formula (27): (IB-PEG$_3$)40-Ex4

Labeling was performed in the same manner as in (4) of Production Example 1 except that a peptide derivative represented by the formula (28) (SEQ ID NO. 28) (320 μg) was used as the labeling precursor in place of the peptide derivative represented by the formula (10) and the reaction time with [$^{125}$I]SIB was changed to 40 minutes, thus obtaining intended (IB-PEG$_3$)40-Ex4 (a peptide derivative represented by the formula (27), (SEQ ID NO. 27)) (radiochemical yield: 32.4%, radiochemical purity: >99%). Further, the time involved in the labeling was 4.3 hours.

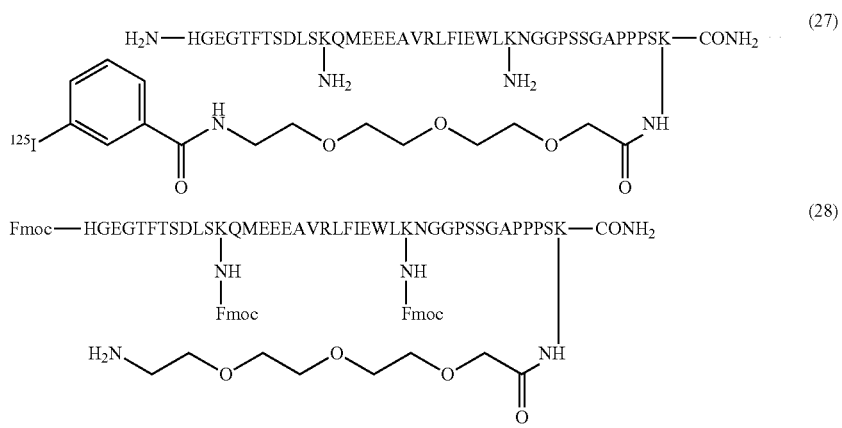

Reference Production Example 5

Labeling was performed in the same manner as in Production Example 5 except that a labeling precursor represented by the formula (29) (510 μg) was used in place of the peptide derivative represented by the formula (28) and the reaction time with [$^{125}$I]SIB was changed to 61 minutes, thus obtaining an intended peptide derivative represented by the formula (30) (SEQ ID NO. 30) (radiochemical yield: 28.3%, radiochemical purity: >99%). Further, the time involved in the labeling was 4.5 hours.

(SEQ ID NO. 29)
Fmoc-HGEGTFTSDLSK(Fmoc)QMEEEAVRLFIEWLK(Fmoc)NGGPSSG
APPPSK-CONH$_2$ (29)

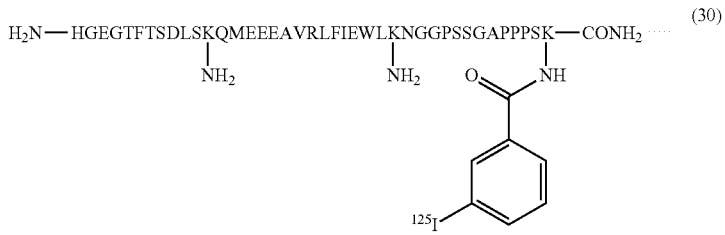

(30)

As Production Example 5 and Reference Production Example 5 show, as a result of performing radioactive labeling using, as the labeling precursor, the peptide derivative of the formula (28) in which PEG3 was bonded to the amino group of the side chain of the lysine, the yield of the radioactively labeled peptide derivative was improved in comparison with the case of using the labeling precursor of the formula (29) in which PEG3 was not bonded to the amino group of the side chain of the lysine.

[Binding Assay]

A binding assay was performed using four kinds of polypeptides (formulae (31) to (34); all cold probes) listed in Table 11 below.

(Procedure of Binding Assay)

The binding assay was performed using the following procedure. First, pancreatic islets isolated from a mouse was recovered in a 50 ml-tube and after it was subjected to centrifugation (2000 rpm, 2 minutes), it was washed once with 20 ml of cold PBS. To this, 15 ml of trypsin-EDTA (which was prepared by adding 12 ml of PBS-containing 0.53 mM EDTA (pH 7.4 (NaOH)) to 3 ml of trypsine-EDTA (0.05%/0.53 mM)) was added. This was incubated at 37° C. for one minute while shaken, then immediately placed on ice. Subsequently, after it was subjected to pipetting vigorously 20 times with a 10 ml pipette dropper without being foamed, the cold PBS was added so that the final amount would be 30 ml. After centrifugation (3000 rpm, 2 minutes), it was washed twice with 30 ml of cold PBS. The supernatant was removed, whereby a pancreatic islet cells sample was obtained. The obtained pancreatic islet cells sample was reserved at −80° C.

The pancreatic islet cells sample was suspended in a buffer (20 mM HEPES (pH 7.4), 1 mM $MgCl_2$, 1 mg/ml bacitracin, 1 mg/ml BSA) so as to make 100 μL/tube. Then, 880 μL of the buffer and 10 μL of a solution including each polypeptide (final concentration of polypeptide: 0, $1\times10^{-6}$ to $1\times10^{-12}$ M), and 10 μL of a solution including [$^{125}$I] Bolton-Hunter labeled Exendin(9-39) (prepared by adding 90 μL of a buffer to 10 μL of [$^{125}$I] Bolton-Hunter labeled Exendin(9-39) (product code: NEX335, 1.85 MBq/ml=50 μCi/ml, 22.73 pmol/ml=76.57 ng/ml, manufactured by Perkin Elmer) were added thereto, which was incubated for 60 minutes at room temperature. Here, the final concentration of the [$^{125}$I] Bolton-Hunter labeled Exendin(9-39) was set to 0.05 μCi/tube. Next, after B/F separation by aspirating with use of an aspirator to which a pre-moistened glass fiber filter (Whatman GF/C filter) was attached, the filter was washed three times with 5 ml of an ice-cold PBS. The filter was set in the tube, and the radioactivity measurement was carried out with a gamma counter. Table 11 below provides the obtained results ($IC_{50}$ of each polypeptide).

TABLE 11

|  | $IC_{50}$(nM) |
| --- | --- |
| ($^{127}$IB-PEG$_3$)12-Ex(9-39) (formula (31), SEQ ID NO. 31) | 3.9 |
| ($^{127}$IB-PEG$_3$)40-Ex(9-39) (formula (32), SEQ ID NO. 32) | 5.7 |
| ($^{127}$IB-PEG$_3$)12-Ex4 (formula (33), SEQ ID NO. 33) | 2.6 |
| ($^{127}$IB-PEG$_3$)40-Ex4 (formula (34), SEQ ID NO. 34) | 2.7 |
| exendin(9-39) (SEQ ID NO. 20) | 1.4 |

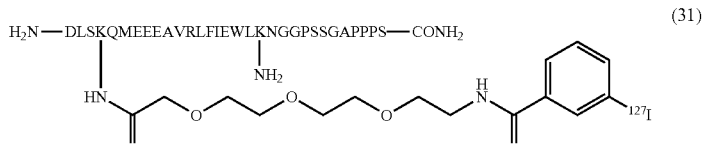

(31)

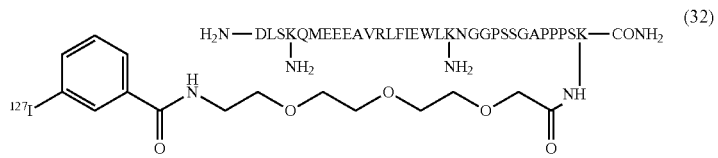

(32)

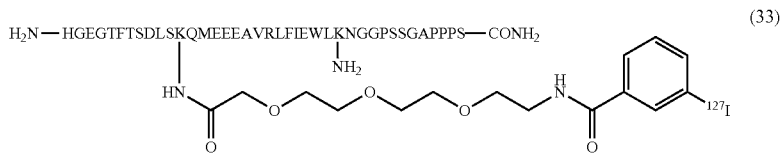

(33)

TABLE 11-continued

IC$_{50}$(nM)

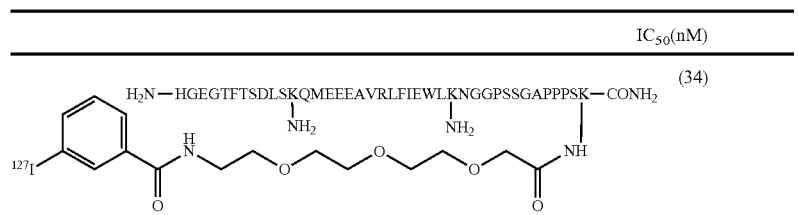

(34)

Each of the polypeptides of the formulae (31) to (34) inhibited in a concentration-dependent manner the binding between the GLP-1R of pancreatic islets and the [$^{125}$I] Bolton-Hunter labeled Exendin(9-39). In particular, ($^{127}$IB-PEG$_3$)12-Ex4 and ($^{127}$IB-PEG$_3$)40-Ex4 exhibited a high affinity for the GLP-1R of pancreatic islets.

Example 5

Biodistribution experiments and two-dimensional imaging analysis were performed using the peptide derivative represented by the formula (25) ((IB-PEG$_3$)12-Ex4).

[Biodistribution Experiment]

Figure 9:
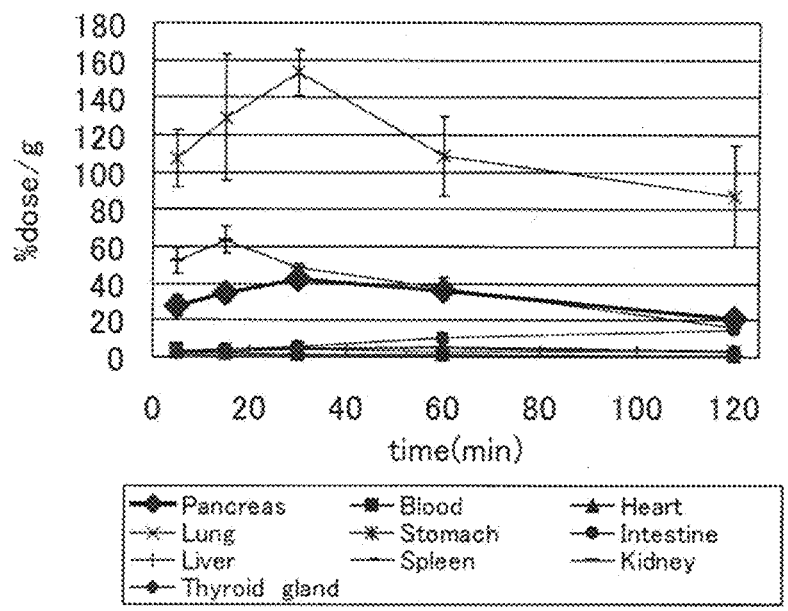
FIG. 9 is a graph showing exemplary time-variations of biodistribution in Example 5.

(IB-PEG$_3$)12-Ex4 (0.77 µCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (IB-PEG$_3$)12-Ex4 was calculated from the radioactivity per unit weight. The exemplary results are shown in Tables 12 and 13 and FIG. 9. FIG. 9 is a graph showing, by way of example, how the accumulation of (IB-PEG$_3$)12-Ex4 in each organ varied with time.

TABLE 12

| | Time after administration | | | | |
|---|---|---|---|---|---|
| | 5 min | 15 min | 30 min | 60 min | 120 min |
| Pancreas | 27.66 | 34.63 | 42.36 | 35.94 | 20.77 |
| | (5.61) | (4.39) | (3.77) | (3.90) | (2.97) |
| Blood | 4.39 | 2.05 | 1.10 | 0.72 | 0.37 |
| | (0.76) | (0.27) | (0.07) | (0.09) | (0.08) |
| Heart | 2.78 | 1.92 | 1.54 | 1.18 | 0.77 |
| | (0.56) | (0.56) | (0.43) | (0.59) | (0.11) |
| Lung | 107.21 | 129.24 | 153.27 | 108.74 | 87.27 |
| | (15.40) | (33.76) | (12.31) | (21.29) | (27.49) |
| Stomach | 3.47 | 4.30 | 5.04 | 5.93 | 3.49 |
| | (1.08) | (0.90) | (1.30) | (3.28) | (1.06) |
| Intestine | 3.07 | 3.91 | 5.85 | 10.29 | 14.56 |
| | (0.27) | (0.48) | (1.17) | (2.45) | (2.03) |
| Liver | 2.07 | 3.10 | 4.50 | 4.63 | 3.05 |
| | (0.29) | (0.19) | (0.58) | (0.66) | (0.68) |
| Spleen | 1.44 | 1.03 | 0.60 | 0.51 | 0.39 |
| | (0.21) | (0.20) | (0.12) | (0.11) | (0.21) |
| Kidney | 52.05 | 63.78 | 48.55 | 37.34 | 15.73 |
| | (7.05) | (7.49) | (2.44) | (6.15) | (2.11) |
| Thyroid gland | 2.66 | 2.67 | 4.11 | 2.85 | 3.15 |
| | (0.77) | (0.74) | (3.36) | (1.07) | (1.06) |

Each numerical value indicates an average (SD) of 5 mice.

TABLE 13

| | Time after administration | | | | |
|---|---|---|---|---|---|
| | 5 min | 15 min | 30 min | 60 min | 120 min |
| Pancreas/Liver Ratio | 13.64 | 11.25 | 9.54 | 7.81 | 6.95 |
| | (3.98) | (1.93) | (1.35) | (0.72) | (1.09) |
| Pancreas/Kidney Ratio | 0.54 | 0.55 | 0.88 | 0.97 | 1.35 |
| | (0.15) | (0.12) | (0.11) | (0.11) | (0.33) |
| Pancreas/Blood Ratio | 6.48 | 17.27 | 38.92 | 50.07 | 56.86 |
| | (1.76) | (4.03) | (6.07) | (3.51) | (7.06) |

As shown in Table 12 and FIG. 9, the accumulation of (IB-PEG$_3$)12-Ex4 in the pancreas reached a level exceeding 25% dose/g at an early stage after the administration, and the accumulation was maintained at a high level thereafter. Further, no great change was seen in the accumulation of (IB-PEG$_3$)12-Ex4 in the thyroid gland. This suggests that (IB-PEG$_3$)12-Ex4 was not subjected to deiodization metabolism in vivo.

As shown in Table 13, the ratio of pancreas/liver for (IB-PEG$_3$)12-Ex4 was greater than 10 at an early stage after the administration. Further, the ratio of pancreas/blood for (IB-PEG$_3$)12-Ex4 was greater than 5 at an early stage after the administration, indicating a satisfactory blood clearance. In this way, the results suggest that clear images of pancreatic β-cells, preferably GLP-1R of pancreatic β-cells can be obtained when performing imaging using (IB-PEG$_3$)12-Ex4, which accumulates in the pancreas in a large amount while showing a high pancreas/liver ratio and has an excellent blood clearance.

[Two-Dimensional Imaging Analysis]

(IB-PEG$_3$)12-Ex4 (5.6 µCi/100 µl) was administered to an unanesthetized MIP-GFP mouse (male, weight: 20 g) by intravenous injection, and after 30 minutes from the administration, the pancreas was dissected out of the mouse (n=1). Sections were cut out of the dissected pancreas, and each section was placed on a slide glass, covered with a cover glass. The fluorescence and the radioactivity (autoradiography) of each section were determined using an image analyzer (trade name: Typhoon 9410, manufactured by GE Health Care Inc.) (exposure time 24 hours). The exemplary results are shown in FIG. 10 under Blocking (−).

Further, non-labeled exendin(9-39) (cold probe, SEQ ID NO. 20) was administered preliminarily to an unanesthetized MIP-GFP mouse (male, weight: 20 g) by intravenous injection (50 µg/100 µl. After 30 minutes from the preliminary administration, (IB-PEG$_3$)12-Ex4 (5.6 µCi/100 µl) was administered to the mouse by intravenous injection. Other than these, the fluorescence and the radioactivity were determined in the same manner as in the above. The exemplary results are shown in FIG. 10 under Blocking (+).

Figure 10:
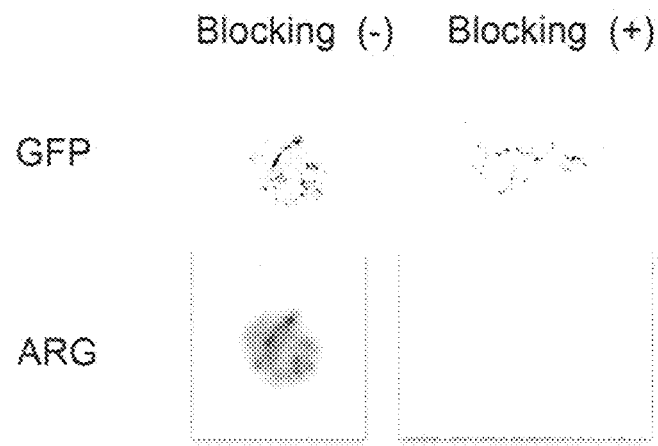
FIG. 10 shows images showing exemplary results of a two-dimensional imaging analysis in Example 5.

FIG. 10 illustrates the exemplary results of the imaging analysis of the pancreas sections of the MIP-GFP mice to which (IB-PEG$_3$)12-Ex4 was administered. The images in the upper row show a fluorescence signal and the images on the lower row show a radioactivity signal. As shown in FIG. 10, the localization of the radioactivity signal was substantially consistent with that of the GFP signal. From this, it was confirmed that (IB-PEG$_3$)12-Ex4 accumulated specifically in the pancreatic β-cells.

Example 6

With use of a peptide derivative represented by the following formula (35) (SEQ ID NO. 35), three-dimensional SPECT imaging was performed.

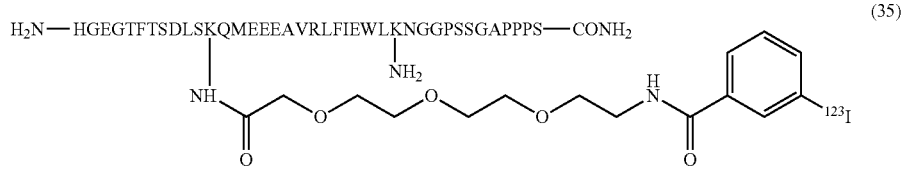

(35)

[Preparation of Peptide Derivative]

The peptide derivative represented by the formula (35) was prepared using the same procedure as the one used in Production Example 4 except that [$^{123}$I]SIB was used in place of [$^{125}$I]SIB.

[Three-Dimensional Imaging]

The peptide derivative represented by the formula (35) (153 μCi (5.66 MBq)/250 μl) was administered to 6-week-old ddY mice (male, weight: about 30 g) by intravenous injection, and then after 20 minutes from the administration of the peptide derivative the mice were subjected to inhalation anesthesia with enflurane. And after 30 minutes from the administration of the peptide derivative, the SPECT imaging was performed under the following imaging conditions with use of a gamma camera (product name: SPECT 2000H-40, manufactured by Hitachi Medical Corporation). Images obtained were reconfigured under the following reconfiguration condition.

Imaging Conditions
Collimator: LEPH collimator
Collecting range: 360°
Step angle: 11.25°
Collecting time: 60 sec per direction
  1×32 frames per 60 sec (total: 32 min)
Reconfiguration Condition
Preprocessing filter: Butterworth filter (order: 10, cutoff frequency: 0.10)

Figure 11:
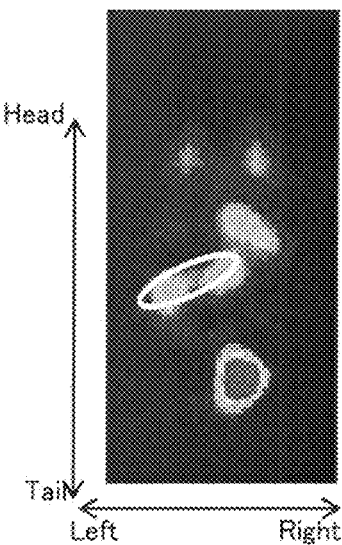
FIG. 11 shows an image showing exemplary results of SPECT imaging in Example 6.

FIG. 11 shows an exemplary image obtained. The image shown in FIG. 11 is a coronal view taken after 30 minutes from the administration of the peptide derivative. The portion circled with a white line indicates the position of the pancreas. As shown in FIG. 11, the position of the pancreas was confirmed noninvasively in mice as a result of the SPECT imaging using the peptide derivative represented by the formula (35). In this way, the position of the pancreas was confirmed noninvasively in a mouse that has the pancreas in a smaller size than that of a human and in which the organs are present more densely than in a human. This suggests that in a human that has the pancreas in a greater size than that of a mouse and in which the organs are present not as densely as in a mouse, the position of the pancreas and the size of the pancreas can be determined more clearly, and moreover, an amount of the peptide derivative bonding to GLP-1R of pancreatic β-cells can be determined.

Example 7

Biodistribution experiments and two-dimensional imaging analysis were performed using the peptide derivative represented by the formula (27) ((IB-PEG$_3$)40-Ex4).

[Biodistribution Experiment]

Figure 12:
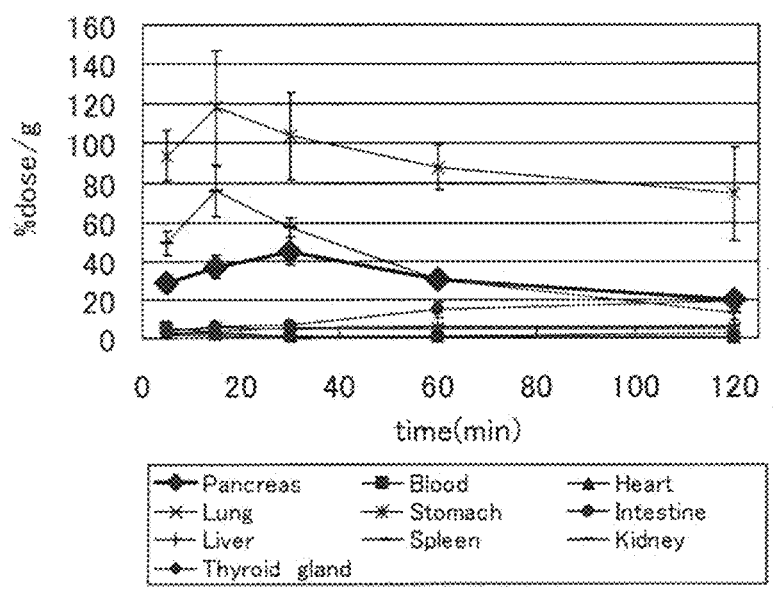
FIG. 12 is a graph showing exemplary time-variations of biodistribution in Example 7.

(IB-PEG$_3$)40-Ex4 (0.74 μCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (IB-PEG$_3$) 40-Ex4 was calculated from the radioactivity per unit weight. The exemplary results are shown in Tables 14 and 15 below and FIG. 12. FIG. 12 is a graph showing, by way of example, how the accumulation of (IB-PEG$_3$)40-Ex4 in each organ varied with time.

TABLE 14

| | Time after administration | | | | |
|---|---|---|---|---|---|
| | 5 min | 15 min | 30 min | 60 min | 120 min |
| Pancreas | 28.70 | 36.93 | 45.09 | 30.76 | 19.65 |
| | (4.48) | (5.97) | (7.01) | (2.63) | (2.21) |
| Blood | 5.71 | 2.85 | 1.32 | 0.75 | 0.35 |
| | (0.68) | (0.25) | (0.17) | (0.08) | (0.07) |
| Heart | 3.10 | 2.41 | 1.16 | 1.14 | 0.78 |
| | (0.41) | (0.17) | (0.26) | (0.08) | (0.26) |
| Lung | 93.55 | 118.10 | 103.68 | 88.00 | 74.43 |
| | (12.68) | (29.03) | (22.13) | (11.65) | (23.81) |
| Stomach | 3.61 | 5.70 | 4.83 | 4.73 | 4.67 |
| | (0.45) | (0.51) | (1.25) | (1.68) | (1.90) |
| Intestine | 4.02 | 6.06 | 6.89 | 14.79 | 19.17 |
| | (0.46) | (0.92) | (1.07) | (3.91) | (3.58) |
| Liver | 2.18 | 3.68 | 5.43 | 5.96 | 6.33 |
| | (0.26) | (0.45) | (0.78) | (0.81) | (7.23) |
| Spleen | 2.07 | 1.23 | 0.80 | 0.46 | 0.39 |
| | (0.21) | (0.22) | (0.23) | (0.06) | (0.18) |
| Kidney | 48.95 | 75.81 | 57.29 | 30.78 | 12.92 |
| | (6.16) | (12.71) | (5.02) | (4.24) | (3.81) |
| Thyroid gland | 2.45 | 2.63 | 1.25 | 1.43 | 2.69 |
| | (0.64) | (2.01) | (0.60) | (1.02) | (1.55) |

Each numerical value indicates an average (SD) of 5 mice.

TABLE 15

| | Time after administration | | | | |
|---|---|---|---|---|---|
| | 5 min | 15 min | 30 min | 60 min | 120 min |
| Pancreas/Liver Ratio | 13.24 | 10.25 | 8.42 | 5.25 | 5.20 |
| | (2.08) | (2.73) | (1.54) | (0.94) | (2.39) |
| Pancreas/Kidney Ratio | 0.60 | 0.49 | 0.79 | 1.01 | 1.59 |
| | (0.14) | (0.09) | (0.08) | (0.06) | (0.34) |
| Pancreas/Blood Ratio | 5.08 | 12.99 | 35.04 | 41.31 | 56.74 |
| | (0.90) | (2.00) | (9.20) | (6.23) | (11.08) |

As shown in Table 14 and FIG. 12, the accumulation of (IB-PEG$_3$)40-Ex4 in the pancreas reached a level exceeding 25% dose/g at an early stage after the administration, and the accumulation was maintained at a high level thereafter. Further, no great change was seen in the accumulation of (IB-PEG$_3$)40-Ex4 in the thyroid gland. This suggests that (IB-PEG$_3$)40-Ex4 was not subjected to deiodization metabolism in vivo.

As shown in Table 15, the ratio of pancreas/liver for (IB-PEG$_3$)40-Ex4 was greater than 10 at an early stage after the administration. Further, the ratio of pancreas/blood for (IB-PEG$_3$)40-Ex4 was greater than 5 at an early stage after the administration, indicating a satisfactory blood clearance. In this way, the results suggest that clear images of pancreatic β-cells, preferably GLP-1R of pancreatic β-cells can be obtained when performing imaging using (IB-PEG$_3$)40-Ex4, which accumulates in the pancreas in a large amount while showing a high pancreas/liver ratio and has an excellent blood clearance.

[Two-Dimensional Imaging Analysis]

(IB-PEG$_3$)40-Ex4 (5.6 µCi/100 µl) was administered to an unanesthetized MIP-GFP mouse (male, weight: 20 g) by intravenous injection, and after 30 minutes from the administration, the pancreas was dissected out of the mouse (n=1). Sections were cut out of the dissected pancreas, and each section was placed on a slide glass, covered with a cover glass. The fluorescence and the radioactivity (autoradiography) of each section were determined using an image analyzer (trade name: Typhoon 9410, manufactured by GE Health Care Inc.) (exposure time 48 hours). The exemplary results are shown in FIG. 13 under Blocking (−).

Further, non-labeled exendin(9-39) (cold probe, SEQ ID NO. 20) was administered preliminarily to an unanesthetized MIP-GFP mouse (male, weight: 20 g) by intravenous injection (50 µg/100 µl). After 30 minutes from the preliminary administration, (IB-PEG$_3$)40-Ex4 (5.6 µCi/100 µl) was administered to the mouse by intravenous injection. Other than these, the fluorescence and the radioactivity were determined in the same manner as above. The exemplary results are shown in FIG. 13 under Blocking (+).

Figure 13:
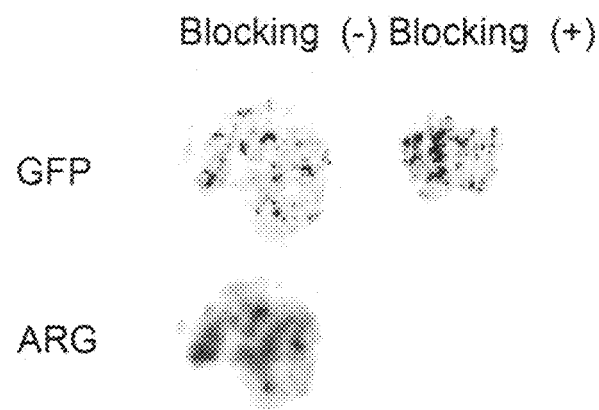
FIG. 13 shows images showing exemplary results of a two-dimensional imaging analysis in Example 7.

FIG. 13 illustrates the exemplary results of the imaging analysis of the pancreas sections of the MIP-GFP mice to which (IB-PEG$_3$)40-Ex4 was administered. The images in the upper row show a fluorescence signal and the images on the lower row show a radioactivity signal. As the images under Blocking (−) in FIG. 13 show, the localization of the radioactivity signal was substantially consistent with that of the GFP signal. From this, it was confirmed that (IB-PEG$_3$)40-Ex4 accumulated specifically in the pancreatic β-cells. Further, as the images under Blocking (+) in FIG. 13 show, the radioactivity signal of (IB-PEG$_3$)40-Ex4 was hardly detected because the receptors were blocked. This suggests that (IB-PEG$_3$)40-Ex4 was accumulated specifically in GLP-1R of the pancreatic β-cells.

Example 8

With use of a peptide derivative represented by the following formula (36) (SEQ ID NO. 36), three-dimensional SPECT imaging was performed.

[Preparation of Peptide Derivative]

The peptide derivative represented by the formula (36) was prepared in the same manner as in Production Example 5 except that [$^{123}$I]SIB was used in place of [$^{125}$I]SIB.

[Three-Dimensional Imaging]

The peptide derivative represented by the formula (36) (154 µCi (5.7 MBq)/100 µl) was administered to 6-week-old ddY mice (male, weight: about 30 g) by intravenous injection, and then after 20 minutes from the administration of the peptide derivative the mice were subjected to inhalation anesthesia with enflurane. And after 30 minutes from the administration of the peptide derivative, the SPECT imaging was performed under the following imaging conditions with use of a gamma camera (product name: SPECT 2000H-40, manufactured by Hitachi Medical Corporation). Images obtained were reconfigured under the following reconfiguration condition.

Imaging Conditions

Collimator: LEPH collimator

Collecting range: 360°

Step angle: 11.25°

Collecting time: 60 sec per direction

1×32 frames per 60 sec (total: 32 min)

Reconfiguration Condition

Preprocessing filter: Butterworth filter (order: 10, cutoff frequency: 0.10)

Figure 14:
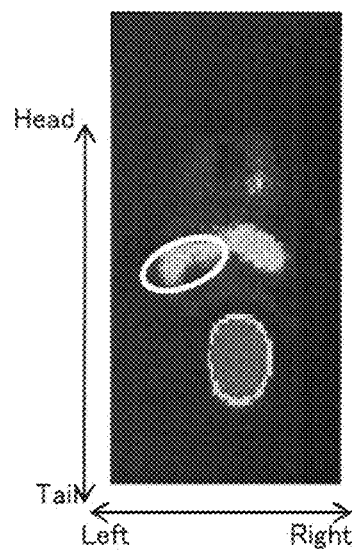
FIG. 14 shows an image showing exemplary results of SPECT imaging in Example 8.

FIG. 14 shows an exemplary image obtained. The image shown in FIG. 14 is a coronal view taken after 30 minutes from the administration of the peptide derivative. The portion circled with a white line indicates the position of the pancreas. As shown in FIG. 14, the position of the pancreas was confirmed noninvasively in mice as a result of the SPECT imaging using the peptide derivative represented by the formula (36).

Example 9

Biodistribution experiments and two-dimensional imaging analysis were performed using the peptide derivative represented by the formula (24) ((FB-PEG$_3$)12-Ex4).

[Biodistribution Experiment]

Figure 15:
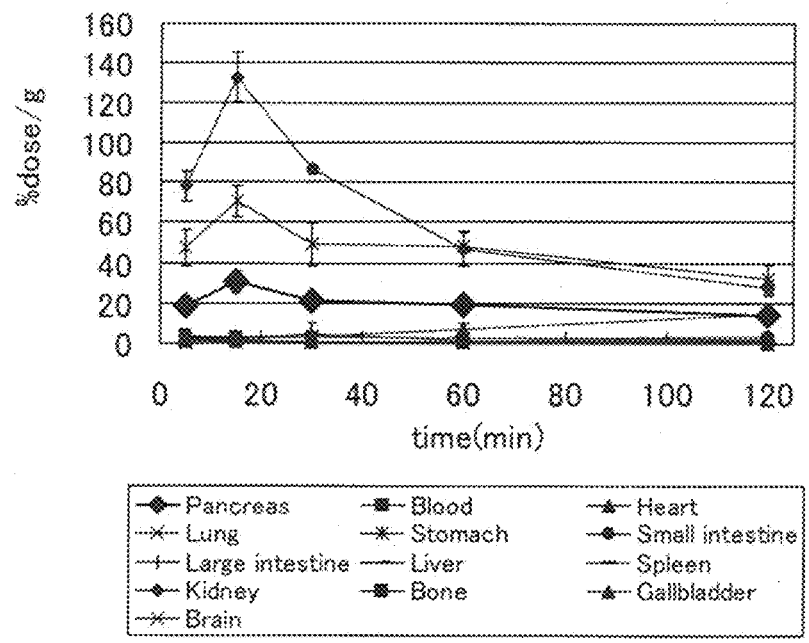
FIG. 15 is a graph showing exemplary time-variations of biodistribution in Example 9.

(FB-PEG$_3$)12-Ex4 (5 µCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (FB-PEG$_3$)12-Ex4 was calculated from the radioactivity per unit weight. The exemplary results are shown in Tables 16 and 17 below and FIG. 15. FIG. 15 is a graph showing, by way of example, how the accumulation of (FB-PEG$_3$)40-Ex4 in each organ varied with time.

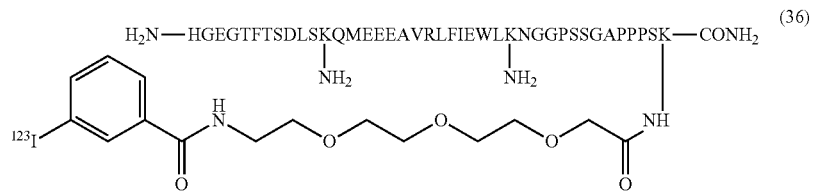

(36)

TABLE 16

| | Time after administration | | | | |
|---|---|---|---|---|---|
| | 5 min | 15 min | 30 min | 60 min | 120 min |
| Pancreas | 18.70 | 30.43 | 21.31 | 19.26 | 14.06 |
| | (1.84) | (5.56) | (2.75) | (3.06) | (0.48) |
| Blood | 3.74 | 1.81 | 0.70 | 0.26 | 0.15 |
| | (0.48) | (0.15) | (0.04) | (0.02) | (0.01) |
| Heart | 2.46 | 1.75 | 0.82 | 0.48 | 0.29 |
| | (0.24) | (0.23) | (0.23) | (0.09) | (0.08) |
| Lung | 47.25 | 70.49 | 49.08 | 47.88 | 31.83 |
| | (8.82) | (7.90) | (10.75) | (8.10) | (7.09) |
| Stomach | 2.21 | 2.95 | 3.16 | 2.61 | 2.09 |
| | (0.57) | (1.05) | (0.68) | (1.33) | (1.33) |
| Small intestine | 3.00 | 3.47 | 3.12 | 2.49 | 3.29 |
| | (0.62) | (0.35) | (0.39) | (0.43) | (0.72) |
| Large intestine | 1.13 | 1.16 | 0.67 | 0.49 | 0.50 |
| | (0.14) | (0.21) | (0.07) | (0.07) | (0.07) |
| Liver | 1.88 | 2.52 | 4.73 | 1.57 | 1.17 |
| | (0.24) | (0.12) | (5.28) | (0.31) | (0.08) |
| Spleen | 2.00 | 1.54 | 0.64 | 0.45 | 0.19 |
| | (0.44) | (0.59) | (0.11) | (0.23) | (0.06) |
| Kidney | 78.02 | 132.66 | 86.15 | 46.63 | 27.73 |
| | (7.32) | (12.35) | (2.29) | (8.42) | (3.90) |
| Bone | 1.17 | 0.87 | 0.55 | 0.43 | 0.18 |
| | (0.23) | (0.24) | (0.05) | (0.31) | (0.10) |
| Gall-bladder | 1.22 | 2.81 | 2.98 | 6.91 | 14.53 |
| | (0.81) | (2.43) | (1.05) | (3.32) | (3.11) |
| Brain | 0.16 | 0.10 | 0.04 | 0.03 | 0.07 |
| | (0.03) | (0.03) | (0.01) | (0.03) | (0.10) |

Each numerical value indicates an average (SD) of 5 mice.

TABLE 17

| | Time after administration | | | | |
|---|---|---|---|---|---|
| | 5 min | 15 min | 30 min | 60 min | 120 min |
| Pancreas/Liver Ratio | 10.14 | 12.10 | 7.85 | 12.52 | 12.08 |
| | (1.98) | (2.45) | (3.94) | (2.58) | (0.66) |
| Pancreas/Kidney Ratio | 0.24 | 0.23 | 0.25 | 0.42 | 0.52 |
| | (0.04) | (0.05) | (0.03) | (0.06) | (0.09) |
| Pancreas/Blood Ratio | 5.08 | 17.04 | 30.73 | 73.47 | 92.83 |
| | (0.94) | (4.47) | (4.91) | (7.06) | (5.34) |

As shown in Table 16 and FIG. 15, the accumulation of (FB-PEG$_3$)12-Ex4 in the pancreas reached a level exceeding 15% dose/g at an early stage after the administration, and the accumulation was maintained at a high level thereafter. Further, the radioactive accumulation of (FB-PEG$_3$)12-Ex4 in the bone was small, suggesting that (FB-PEG$_3$)12-Ex4 was not subjected to deiodization metabolism in viva As shown in Table 17, the ratio of pancreas/liver for (FB-PEG$_3$)12-Ex4 was greater than 10 at an early stage after the administration. Further, the ratio of pancreas/blood for (FB-PEG$_3$)12-Ex4 was greater than 5 at an early stage after the administration, indicating a satisfactory blood clearance. In this way, the results suggest that clear images of pancreatic β-cells, preferably GLP-1R of pancreatic β-cells can be obtained when performing imaging using (FB-PEG$_3$)12-Ex4, which accumulates in the pancreas in a large amount while showing a high pancreas/liver ratio and has an excellent blood clearance.

[Two-Dimensional Imaging Analysis]

(FB-PEG$_3$)12-Ex4 (292 μCi/220 μl) was administered to an unanesthetized MIP-GFP mouse (male, weight: 20 g) by intravenous injection, and after 15 minutes from the administration, the pancreas was dissected out of the mouse (n=1). Sections were cut out of the dissected pancreas, and each section was placed on a slide glass, covered with a cover glass. The fluorescence and the radioactivity (autoradiography) of each section were determined using an image analyzer (trade name: Typhoon 9410, manufactured by GE Health Care Inc.) (exposure time 24 hours). The exemplary results are shown in FIG. 16.

Figure 16:
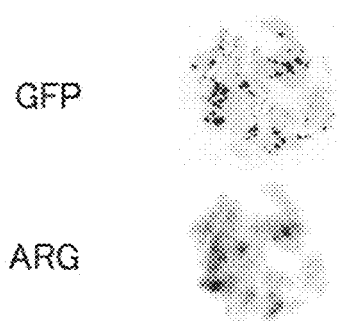
FIG. 16 shows images showing exemplary results of a two-dimensional imaging analysis in Example 9.

FIG. 16 illustrates the exemplary results of the imaging analysis of the pancreas sections of the MIP-GFP mice to which (FB-PEG$_3$)12-Ex4 was administered. The image in the upper row shows a fluorescence signal and the image on the lower row shows a radioactivity signal. As shown in FIG. 16, the localization of the radioactivity signal was substantially consistent with that of the GFP signal. From this, it was confirmed that (FB-PEG$_3$)12-Ex4 accumulated specifically in the pancreatic β-cells.

Production Example 6

Synthesis of Peptide Derivative Represented by Formula (37): (IB-ePEG$_{12}$)12-Ex4

A peptide derivative represented by the following formula (38) (SEQ ID NO. 38) was prepared in the same manner as in Production Example 3 except that Fmoc-Lys (Boc-ePEG12) was used in place of Fmoc-Lys (Boc-PEG3). Next, labeling was performed in the same manner as in (4) of Production Example 1 except that the obtained peptide derivative represented by the formula (38) (540 μg) was used in place of the peptide derivative represented by the formula (10), thus obtaining intended (IB-ePEG$_{12}$)12-Ex4 (peptide derivative represented by the following formula (37) (SEQ ID NO. 37) (radiochemical yield: 41.8%, radiochemical purity: 95.7%). Further, the time involved in the labeling was 2.75 hours. Note that the time involved in the labeling includes the reaction time with the labeling compound, the HPLC purification time, the deprotection reaction time after the reaction with the labeling compound, the LC purification time and the concentration time.

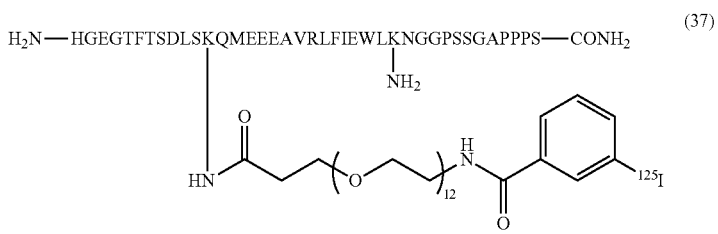

(37)

-continued

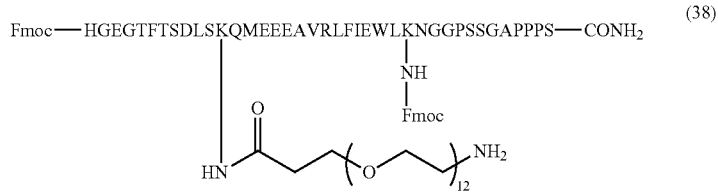

(38)

Example 10

Biodistribution experiments were performed using the peptide derivative represented by the formula (37) ((IB-ePEG$_{12}$)12-Ex4).

[Biodistribution Experiment]

Figure 17:
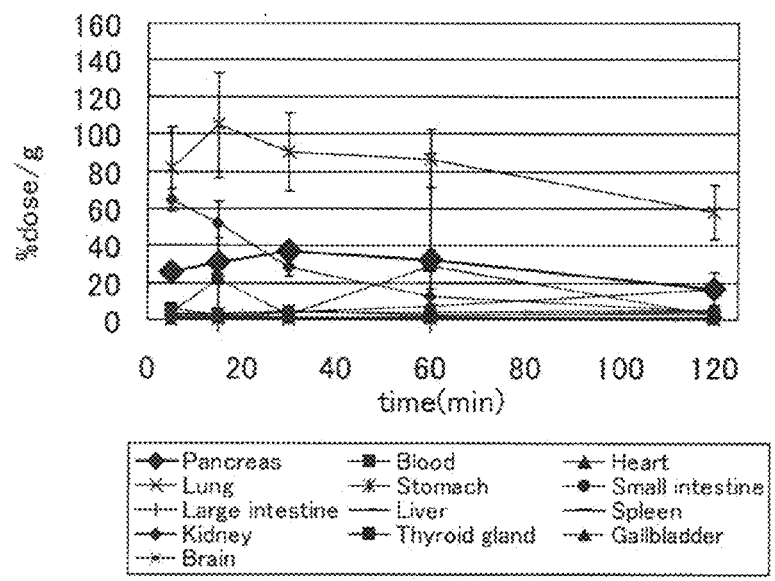
FIG. 17 is a graph showing exemplary time-variations of biodistribution in Example 10.

(IB-ePEG$_{12}$)12-Ex4 (0.21 µCi) was administered to unanesthetized 6-week-old ddY mice (male, weight: 30 g) by intravenous injection (through the tail vein). After 5 minutes, 15 minutes, 30 minutes, 60 minutes, and 120 minutes from the administration, organs were dissected out of the mice (n=5). The weight and the radioactivity of each organ were determined, and an accumulation amount (% dose/g) of (IB-ePEG$_{12}$)12-Ex4 was calculated from the radioactivity per unit weight. The exemplary results are shown in Tables 18 and 19 and FIG. 17. FIG. 17 is a graph showing, by way of example, how the accumulation of (IB-ePEG$_{12}$)12-Ex4 in each organ varied with time.

TABLE 18

| | Time after administration | | | | |
|---|---|---|---|---|---|
| | 5 min | 15 min | 30 min | 60 min | 120 min |
| Pancreas | 25.87 | 30.87 | 36.95 | 32.07 | 16.47 |
| | (2.33) | (1.82) | (3.35) | (5.74) | (1.18) |
| Blood | 5.72 | 2.36 | 1.25 | 0.70 | 0.37 |
| | (0.67) | (0.21) | (0.22) | (0.05) | (0.04) |
| Heart | 3.07 | 1.83 | 1.48 | 1.10 | 0.73 |
| | (0.47) | (0.15) | (0.32) | (0.13) | (0.15) |
| Lung | 81.86 | 104.67 | 90.49 | 86.48 | 57.99 |
| | (21.39) | (28.35) | (21.11) | (15.69) | (14.71) |
| Stomach | 3.44 | 3.23 | 4.33 | 2.92 | 3.09 |
| | (1.76) | (0.95) | (1.68) | (0.64) | (1.42) |
| Small intestine | 3.13 | 3.58 | 3.77 | 4.17 | 5.56 |
| | (0.44) | (0.57) | (0.27) | (0.40) | (1.71) |
| Large intestine | 1.13 | 0.95 | 0.89 | 1.77 | 4.51 |
| | (0.25) | (0.18) | (0.09) | (1.30) | (1.25) |
| Liver | 1.96 | 1.53 | 1.37 | 0.91 | 1.25 |
| | (0.20) | (0.14) | (0.17) | (0.12) | (0.82) |
| Spleen | 1.44 | 0.96 | 0.61 | 0.25 | 0.24 |
| | (0.19) | (0.47) | (0.20) | (0.08) | (0.02) |
| Kidney | 64.47 | 52.07 | 28.22 | 12.45 | 4.47 |
| | (6.11) | (7.89) | (4.76) | (3.84) | (1.09) |
| Thyroid gland | 3.77 | 21.86 | 2.86 | 28.74 | 2.88 |
| | (3.06) | (42.17) | (3.24) | (61.14) | (2.72) |
| Gallbladder | 0.55 | 1.23 | 3.96 | 6.96 | 16.73 |
| | (0.47) | (0.78) | (3.25) | (1.24) | (8.83) |
| Brain | 0.15 | 0.08 | 0.04 | 0.03 | 0.03 |
| | (0.03) | (0.02) | (0.02) | (0.01) | (0.02) |

Each numerical value indicates an average (SD) of 5 mice.

TABLE 19

| | Time after administration | | | | |
|---|---|---|---|---|---|
| | 5 min | 15 min | 30 min | 60 min | 120 min |
| Pancreas/Liver Ratio | 13.32 | 20.27 | 27.39 | 35.74 | 17.98 |
| | (1.81) | (2.30) | (5.03) | (7.00) | (9.31) |
| Pancreas/Kidney Ratio | 0.40 | 0.60 | 1.35 | 2.77 | 3.80 |
| | (0.02) | (0.08) | (0.29) | (0.94) | (0.61) |
| Pancreas/Blood Ratio | 4.56 | 13.18 | 30.36 | 45.68 | 44.77 |
| | (0.58) | (1.58) | (6.54) | (5.91) | (5.91) |

As shown in Table 18 and FIG. 17, the accumulation of (IB-ePEG$_{12}$)12-Ex4 in the pancreas reached a level exceeding 25% dose/g at an early stage after the administration, and the accumulation was maintained at a high level thereafter. Further, no great change was seen in the accumulation of (IB-ePEG$_{12}$)12-Ex4 in the thyroid gland. This suggests that (IB-ePEG$_{12}$)12-Ex4 was not subjected to deiodization metabolism in vivo.

As shown in Table 19, the ratio of pancreas/liver for (IB-ePEG$_{12}$)12-Ex4 was greater than 10 at an early stage after the administration and the ratio was maintained at a high level thereafter. Further, the ratio of pancreas/blood for (IB-ePEG$_{12}$)12-Ex4 was greater than 5 at an early stage after the administration and the ratio was maintained at a high level thereafter, indicating a satisfactory blood clearance. In this way, the results suggest that clear images of pancreatic β-cells, preferably GLP-1R of pancreatic β-cells can be obtained when performing imaging using (IB-ePEG$_{12}$)12-Ex4, which accumulates in the pancreas in a large amount while showing a high pancreas/liver ratio and has an excellent blood clearance.

Example 11

With use of a peptide derivative represented by the following formula (39) (SEQ ID NO. 39), three-dimensional SPECT imaging was performed.

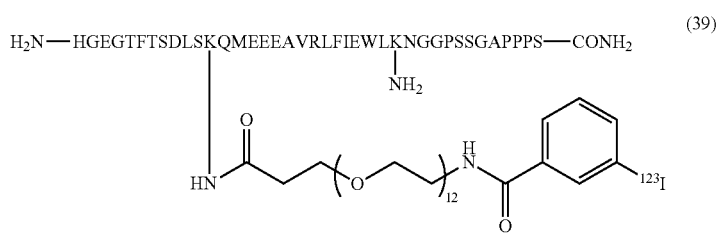

(39)

[Preparation of Peptide Derivative]

The peptide derivative represented by the formula (39) was prepared using the same procedure as in Production Example 6 except that [$^{123}$I]SIB was used in place of [$^{125}$I]SIB.

[Three-Dimensional Imaging]

Figure 18:
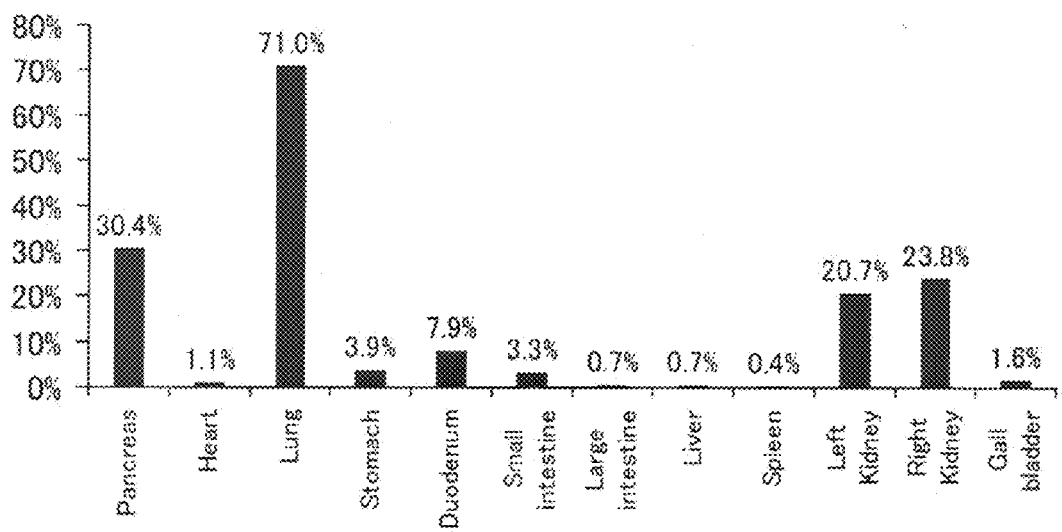
FIG. 18 is a graph showing, by way of example, a percentage of radioactive accumulation per gram of each organ in Example 11.

SPECT imaging of a mouse was performed in the same manner as in Example 8 except that the peptide derivative represented by the formula (39) was used in place of the peptide derivative of the formula (36) and the administration amount was changed to 233 µCi ((8.6 MBq)/120 µl). The exemplary results are shown in FIG. 18. FIG. 18 is a graph showing the percentage of administered radiation per gram of each organ of the mouse (percentage of radioactive accumulation per gram of organ (% dose/g)). As shown in FIG. 18, the accumulation was hardly seen in the liver and the large intestine, indicating favorable results. Further, the position of the pancreas was confirmed noninvasively from the images obtained (data not shown).

As described above, the present invention is useful in, for example, the medical field, the molecule imaging field, and the field relating to diabetes.

The invention may be embodied in other forms without departing from the spirit of essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

SEQUENCE LISTING FREE TEXT

SEQ ID NO. 1: an amino acid sequence of exendin-4

SEQ ID NO. 2: an exemplary amino acid sequence of a peptide derivative of the present invention SEQ ID NO. 3: an exemplary amino acid sequence of a peptide derivative of the present invention SEQ ID NO. 4: an exemplary amino acid sequence of a peptide derivative of the present invention SEQ ID NO. 5: an exemplary amino acid sequence of a peptide derivative of the present invention SEQ ID NO. 6: an amino acid sequence of a peptide derivative produced in Production Example 1

SEQ ID NO. 7: an amino acid sequence of the protected peptide resin A produced in Production Example 1

SEQ ID NO. 8: an amino acid sequence of the protected peptide resin A1 produced in Production Example 1

SEQ ID NO. 9: an amino acid sequence of the protected peptide resin A2 produced in Production Example 1

SEQ ID NO. 10: an amino acid sequence of the labeling precursor produced in Production Example 1

SEQ ID NO. 11: an amino acid sequence of a peptide derivative produced in Reference Production Example 1

SEQ ID NO. 12: an amino acid sequence of a labeling precursor used in Reference Production Example 1

SEQ ID NO. 13: an amino acid sequence of a peptide derivative produced in Production Example 2

SEQ ID NO. 14: an amino acid sequence of the protected peptide resin B produced in Production Example 2

SEQ ID NO. 15: an amino acid sequence of a labeling precursor produced in Production Example 2

SEQ ID NO. 16: an amino acid sequence of a peptide derivative produced in Reference Production Example 2

SEQ ID NO. 17: an amino acid sequence of a labeling precursor used in Reference Production Example 2

SEQ ID NO. 18: an amino acid sequence of a peptide derivative used in Example 2

SEQ ID NO. 19: an amino acid sequence of a peptide derivative used in Example 4

SEQ ID NO. 20: an amino acid sequence of exendin(9-39)

SEQ ID NO. 21: an amino acid sequence of a peptide derivative produced in Production Example 3

SEQ ID NO. 22: an amino acid sequence of a labeling precursor produced in Production Example 3

SEQ ID NO. 23: an amino acid sequence of a labeling precursor produced in Reference Production Example 3

SEQ ID NO. 24: an amino acid sequence of a peptide derivative produced in Reference Production Example 3

SEQ ID NO. 25: an amino acid sequence of a peptide derivative produced in Production Example 4

SEQ ID NO. 26: an amino acid sequence of a peptide derivative produced in Reference Production Example 4

SEQ ID NO. 27: an amino acid sequence of a peptide derivative produced in Production Example 5

SEQ ID NO. 28: an amino acid sequence of a labeling precursor produced in Production Example 5

SEQ ID NO. 29: an amino acid sequence of a labeling precursor produced in Reference Production Example 5

SEQ ID NO. 30: an amino acid sequence of a peptide derivative produced in Reference Production Example 5

SEQ ID NO. 31: an amino acid sequence of polypeptide used in a binding assay

SEQ ID NO. 32: an amino acid sequence of polypeptide used in a binding assay

SEQ ID NO. 33: an amino acid sequence of polypeptide used in a binding assay

SEQ ID NO. 34: an amino acid sequence of polypeptide used in a binding assay

SEQ ID NO. 35: an amino acid sequence of a peptide derivative used in Example 6

SEQ ID NO. 36: an amino acid sequence of a peptide derivative used in Example 8

SEQ ID NO. 37: an amino acid sequence of a peptide derivative produced in Production Example 6

SEQ ID NO. 38: an amino acid sequence of a labeling precursor produced in Production Example 6

SEQ ID NO. 39: an amino acid sequence of a peptide derivative used in Example 10

What is claimed is:

1. A peptide derivative represented by formula (I)

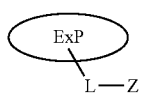
(I)

where ExP represents a polypeptide that is represented by an amino acid sequence of formula (1), Ex4(x-y)-K$_n$     (1)

where Ex4(x-y) represents the amino acid sequence starting at a first residue at position x of SEQ ID NO: 1 and ending at a last residue at position y of SEQ ID NO: 1, x is an integer of 1 to 9, y is an integer of 30 to 39, K represents lysine, and n is 0 or 1, wherein the amino acid at position 1 of SEQ ID NO: 1 is the first residue of SEQ ID NO: 1 and the amino acid at position 30 of SEQ ID NO: 1 is the thirtieth residue of SEQ ID NO: 1;

(SEQ ID NO: 1)
HGEGTFTSDLSKQMEEEAVRLFIEWLKNGGPSSGAPPPS, an α-amino group at an N-terminus of the polypeptide ExP is not modified, modified with a modifying group having no electric charge, or bonded to the -L-Z group of formula (I), a carboxylic group at a C-terminus of the polypeptide ExP is amidated, the -L-Z group of formula (I) represents a group represented by formula (II),

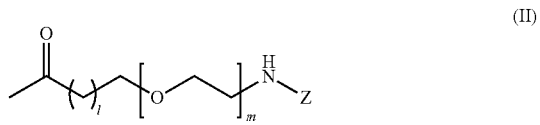
(II)

where when n in the formula (1) is 1, l is 0, 1 or 2, and m is an integer of 1 to 30, when n in the formula (1) is 0, l is an integer of 0 to 8, and m is an integer of 0 to 30, the -L-Z group of formula (I) is bonded to a side group of any lysine residue or the α-amino group at the N-terminus of the polypeptide ExP, Z represents a labeling group comprising a radionuclide or isotope thereof, and the modifying group having no electric charge is selected from the group consisting of 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having a carbon number of 3 to 20, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy-2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group, 2-bromobenzyloxycarbonyl group, benzyloxymethyl group (Bom), cyclohexyloxy group (cHxO), t-butoxymethyl group (Burn), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl group, cyclohexyl group, cyclopentyl group, isopropyl group, pivalyl group, tetrahydropyran-2-yl group, and trimethylsilyl group.

2. The peptide derivative according to claim 1, wherein Ex4(x-y)-K$_n$ is selected from the group consisting of amino acid sequences represented by SEQ ID NO: 2, 3, 4 and 5:

```
                                              (SEQ ID NO: 2)
HGEGTFTSDLSKQMEEEAVRLFIEWLKNGGPSSGAPPPS (SEQ ID NO: 3)
HGEGTFTSDLSKQMEEEAVRLFIEWLKNGGPSSGAPPPSK (SEQ ID NO: 4)
DLSKQMEEEAVRLFIEWLKNGGPSSGAPPPS (SEQ ID NO: 5)
DLSKQMEEEAVRLFIEWLKNGGPSSGAPPPSK.
```

3. The peptide derivative according to claim 1, wherein the -L-Z group is bonded to an amino group of a side chain of lysine that corresponds to position 12 of the amino acid sequence of SEQ ID NO: 1 or to an amino group of a side chain of K$_n$ in the formula (1).

4. The peptide derivative according to claim 1, wherein Z is a group represented by formula (III),

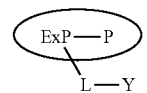

(III)

where Ar represents an aromatic hydrocarbon group or aromatic heterocyclic group,
R$^1$ represents a substituent selected from the group consisting of radionuclides, radionuclide-substituted C$_1$-C$_3$ alkyl groups, radionuclide-substituted C$_1$-C$_3$ alkoxy groups, R$^2$ represents a substituent selected from the group consisting of hydrogen atom, hydroxyl group, cyano group, nitro group, halogen atoms, carbonyl group, sulfonyl group, acetyl group, phenyl group, C$_1$-C$_6$ alkyl groups, C$_2$-C$_6$ alkenyl groups, and C$_2$-C$_6$ alkynyl groups, and R$^2$ is different from the substituent represented by R$^1$, and
R$^3$ represents a bond, alkylene group having 1 to 6 carbon atoms or oxyalkylene group having 1 to 6 carbon atoms.

5. The peptide derivative according to claim 1, wherein Z represents a labeling group containing a radionuclide.

6. A composition comprising the peptide derivative according to claim 1.

7. A reagent for imaging comprising the peptide derivative according to claim 5.

8. A peptide derivative represented by formula (IV),

(IV)

where ExP-P represents polypeptide that is represented by an amino acid sequence of formula (1), Ex4(x-y)-K$_n$                              (1)

where Ex4(x-y) represents the amino acid sequence starting at a first residue at position x of SEQ ID NO: 1 and ending at a last residue at position y of SEQ ID NO: 1, x is an integer of 1 to 9, y is an integer of 30 to 39, K represents lysine, and n is 0 or 1, wherein the amino acid at position 1 of SEQ ID NO: 1 is the first residue of SEQ ID NO: 1 and the amino acid at position 30 of SEQ ID NO: 1 is the thirtieth residue of SEQ ID NO: 1;

```
                                              (SEQ ID NO: 1)
HGEGTFTSDLSKQMEEEAVRLFIEWLKNGGPSSGAPPPS,
``` an α-amino group at an N-terminus of the polypeptide ExP-P is bonded to a protecting group or the -L-Y group of formula (IV), modified with a modifying group having no electric charge, or not modified,
a carboxylic group at a C-terminus of the polypeptide ExP-P is amidated,
the -L-Y group of formula (IV) represents a group represented by formula (V),

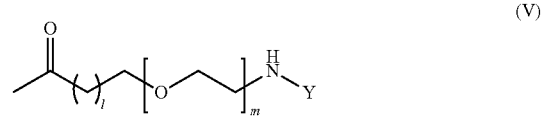

(V)

where when n in the formula (1) is 1, l is 0, 1 or 2, and m is an integer of 1 to 30,
when n in the formula (1) is 0, l is an integer of 0 to 8, and m is an integer of 0 to 30,
the -L-Y group of formula (IV) is bonded to a side group of any lysine residue or the α-amino group at the N-terminus of the polypeptide ExP,
Y represents a hydrogen atom; a chelating site selected from the group consisting of diethylenetriaminepentaacetic acid (DTPA), 6-hydrazinopyridine-3-carboxylic acid (HYNIC), tetraazacyclododecanetetraacetic acid (DOTA), dithisosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO); or formula (VI),

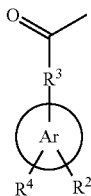

where Ar represents an aromatic hydrocarbon group or aromatic heterocyclic group,
$R^4$ represents a substituent selected from the group consisting of a mesylate (OMs) group, tosylate (OTs) group, triflate (OTf) group, $^{80}$Br bromine atom, $^{127}$I iodine atom, chlorine atom, nitro group, trimethylammonium group, tin atom, alkyltin group, and alkylsilicon group,
$R^2$ represents a substituent selected from the group consisting of hydrogen atom, hydroxyl group, cyano group, nitro group, halogen atoms, carbonyl group, sulfonyl group, acetyl group, phenyl group, $C_1$-$C_6$ alkyl groups, $C_2$-$C_6$ alkenyl groups, and $C_2$-$C_6$ alkynyl groups, and $R^2$ is different from the substituent represented by $R^4$, and
$R^3$ represents a bond, alkylene group having 1 to 6 carbon atoms or oxyalkylene group having 1 to 6 carbon atoms, and the modifying group having no electric charge is selected from the group consisting of 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having a carbon number of 3 to 20, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy-2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group, 2-bromobenzyloxycarbonyl group, benzyloxymethyl group (Bom), cyclohexyloxy group (cHxO), t-butoxymethyl group (Bum), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl group, cyclohexyl group, cyclopentyl group, isopropyl group, pivalyl group, tetrahydropyran-2-yl group, and trimethylsilyl group.

9. The peptide derivative according to claim 8, wherein Ex4(x-y)-$K_n$ is selected from the group consisting of amino acid sequences represented by SEQ ID NO: 2, 3, 4 and 5:

HGEGTFTSDLSKQMEEEAVRLFIEWLKNGGPSSGAPPPS (SEQ ID NO. 2)

HGEGTFTSDLSKQMEEEAVRLFIEWLKNGGPSSGAPPPSK (SEQ ID NO. 3)

DLSKQMEEEAVRLFIEWLKNGGPSSGAPPPS (SEQ ID NO. 4)

DLSKQMEEEAVRLFIEWLKNGGPSSGAPPPSK. (SEQ ID NO. 5)

10. A method of detecting pancreatic β-cells, comprising administering the peptide derivative according to claim 5 to an subject, and
detecting a signal from the radionuclide of the peptide derivative from the subject.

11. The method of imaging pancreatic β-cells, comprising administering the peptide derivative according to claim 5 to a subject,
detecting a signal from the radionuclide of the peptide derivative from the subject, generating an image by reconfiguring the detected signal to convert the signal into the image using a collimator and a filter, and displaying the image.

12. A method of determining an amount of pancreatic islets, the method comprising:
administering the peptide derivative according to claim 5 to a subject,
detecting a signal from the radionuclide of the peptide derivative from the subject, and
calculating an amount of pancreatic islets based on a calibration curve generated from the detected signal of the peptide derivative.

13. The method according to claim 12, further comprising displaying the calculated amount of pancreatic islets.

14. The peptide derivative according to claim 1, wherein Ex4(x-y)-$K_n$ is SEQ ID NO: 2.

15. The peptide derivative according to claim 1, wherein
x, y, and n are 1, 39 and 0, respectively;
the α-amino group is not modified; and
l and m are 1 and 12, respectively.

16. The peptide derivative according to claim 4, wherein
x, y, and n are 1, 39 and 0, respectively;
the α-amino group is not modified;
l, m, Ar, $R_2$, and $R_3$, are 1, 12, a phenyl group, H, and a bond, respectively; and
$R_1$ is $^{18}$F or $^{123/124/125/131}$I.

17. The peptide derivative according to claim 1, wherein
when n in the formula (1) is 1, l is 1 or 2, and m is an integer of 1 to 30, and
when n in the formula (1) is 0, l is an integer of 1 to 8, and m is an integer of 1 to 30.

18. The peptide derivative according to claim 1, wherein the modifying group having no electric charge is selected from the group consisting of acetyl group, benzyl group, benzyloxymethyl group, o-bromobenzyloxycarbonyl group, t-butyl group, t-butyldimethylsilyl group, 2-chlorobenzyl group, 2,6-dichlorobenzyl group, cyclohexyl group, cyclopentyl group, isopropyl group, pivalyl group, tetrahydropyran-2-yl group, tosyl group, trimethylsilyl group, or trityl group.

19. The peptide derivative according to claim 1, wherein the modifying group having no electric charge is acetyl group.

20. The peptide derivative according to claim 1, wherein the radionuclide is selected from the group consisting of $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{82}$Rb, $^{99m}$Tc, $^{111}$In, $^{123}$I, $^{124}$I, $^{125}$I, $^{131}$I and $^{186}$Re.

21. The peptide derivative according to claim 1, wherein the radionuclide is a positron emission nuclide or a γ-emission nuclide.

22. The peptide derivative according to claim 1, wherein the radionuclide is selected from the group consisting of $^{18}$F, $^{75}$Br, $^{76}$Br, $^{77}$Br, $^{123}$I, and $^{124}$I.

23. The peptide derivative according to claim 4, wherein Ar represents (i) an aromatic hydrocarbon group having a carbon number of 6 to 18, or (ii) a 5 to 10-membered heterocyclic group comprising one or two nitrogen atoms, oxygen atoms, or sulfur atoms.

24. The peptide derivative according to claim 4, wherein Ar is selected from the group consisting of phenyl group, o-tolyl group, m-tolyl group, p-tolyl group, 2,4-xylyl group, p-cumenyl group, mesityl group, 1-naphthyl group, 2-naphthyl group, 1-anthryl group, 2-anthryl group, 9-anthryl group, 1-phenanthryl group, 9-phenanthryl group, 1-acenanthryl group, 2-azulenyl group, 1-pyrenyl group, 2-triphenylenyl group, o-biphenylyl group, m-biphenylyl group, p-biphenylyl group, terphenyl group, triazolyl group, 3-oxadiazolyl group, 2-furyl group, 3-furyl group, 2-thienyl group, 3-thienyl group, 1-pyrrolyl group, 2-pyrrolyl group, 3-pyrrolyl group, 2-pyridyl group, 3-pyridyl group, 4-pyridyl group, 2-pyradyl group, 2-oxazolyl group, 3-isoxyazolyl group, 2-thiazolyl group, 3-isothiazolyl group, 2-imidazolyl group, 3-pyrazolyl group, 2-quinolyl group, 3-quinolyl group, 4-quinolyl group, 5-quinolyl group, 6-quinolyl group, 7-quinolyl group, 8-quinolyl group, 1-isoquinolyl group, 2-quinoxalynyl group, 2-benzofuryl group, 2-benzothienyl group, N-indolyl group, and N-carbazolyl group.

25. The peptide derivative according to claim 4, wherein Ar is selected from the group consisting of phenyl group, triazolyl group, and pyridyl group.

26. The peptide derivative according to claim 4, wherein R$^1$ represents a substituent comprising a radioactive halogen nuclide selected from the group consisting of $^{18}$F, $^{75/76/77}$Br, and $^{123/124/125/131}$I.

27. The peptide derivative according to claim 4, wherein R$^2$ represents a hydrogen atom.

28. The peptide derivative according to claim 1, wherein Z is a group represented by formula (IIIa), (IIIb), (IIIc), or (IIId),

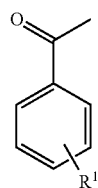

(IIIa)

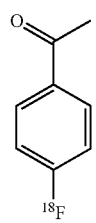

(IIIb)

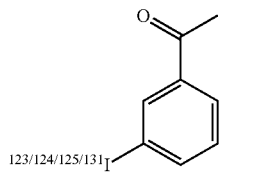

(IIIc)

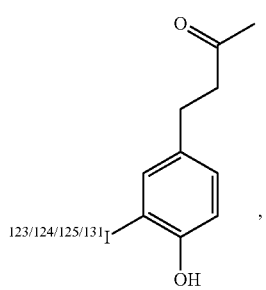

(IIId)

wherein R$^1$ represents a substituent selected from the group consisting of radionuclides, radionuclide-substituted C$_1$-C$_3$ alkyl groups, radionuclide-substituted C$_1$-C$_3$ alkoxy groups.

29. A kit comprising the peptide derivative of claim 1.

30. A kit comprising the peptide derivative of claim 8.

31. The peptide derivative according to claim 8, wherein Y represents the formula (VI),

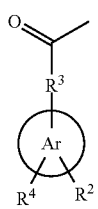

(VI)

where Ar represents an aromatic hydrocarbon group or aromatic heterocyclic group, R$^4$ represents a substituent selected from the group consisting of a mesylate (OMs) group, tosylate (OTs) group, triflate (OTf) group, $^{80}$Br bromine atom, $^{127}$I iodine atom, chlorine atom, nitro group, trimethylammonium group, tin atom, alkyltin group, and alkylsilicon group, R$^2$ represents a substituent selected from the group consisting of hydrogen atom, hydroxyl group, cyano group, nitro group, halogen atoms, carbonyl group, sulfonyl group, acetyl group, phenyl group, C$_1$-C$_6$ alkyl groups, C$_2$-C$_6$ alkenyl groups, and C$_2$-C$_6$ alkynyl groups, and R$^2$ is different from the substituent represented by R$^4$, and R$^3$ represents a bond, alkylene group having 1 to 6 carbon atoms or oxyalkylene group having 1 to 6 carbon atoms, and the modifying group having no electric charge is selected from the group consisting of 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having a carbon number of 3 to 20, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy-2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group, 2-bromobenzyloxycarbonyl group, benzyloxymethyl group (Bom), cyclohexyloxy group (cHxO), t-butoxymethyl group (Bum), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl group, cyclohexyl group, cyclopentyl group, isopropyl group, pivalyl group, tetrahydropyran-2-yl group, and trimethylsilyl group.

32. The peptide derivative according to claim 8, wherein when n in the formula (1) is 1, l is 1 or 2, and m is an integer of 1 to 30, and
when n in the formula (1) is 0, l is an integer of 1 to 8, and m is an integer of 1 to 30.

33. The peptide derivative according to claim 8, wherein Y is a hydrogen atom.

34. The peptide derivative according to claim 8, wherein Y represents a chelating site selected from the group consisting of diethylenetriaminepentaacetic acid (DTPA), 6-hydrazinopyridine-3-carboxylic acid (HYNIC), tetraazacyclododecanetetraacetic acid (DOTA), dithisosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO).

35. The peptide derivative according to claim 1, wherein Z is a group represented by formula (III),

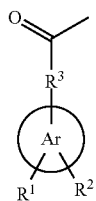
(III)

where Ar represents an aromatic hydrocarbon group or aromatic heterocyclic group,
$R^1$ represents a substituent selected from the group consisting of isotopes of radionuclides, isotopes of radionuclide-substituted $C_1$-$C_3$ alkyl groups, and isotopes of radionuclide-substituted $C_1$-$C_3$ alkoxy groups,
$R^2$ represents a substituent selected from the group consisting of hydrogen atom, hydroxyl group, cyano group, nitro group, halogen atoms, carbonyl group, sulfonyl group, acetyl group, phenyl group, $C_1$-$C_6$ alkyl groups, $C_2$-$C_6$ alkenyl groups, and $C_2$-$C_6$ alkynyl groups, and $R^2$ is different from the substituent represented by $R^1$, and
$R^3$ represents a bond, alkylene group having 1 to 6 carbon atoms or oxyalkylene group having 1 to 6 carbon atoms.

36. The peptide derivative according to claim 1, wherein Z is a group represented by formula (IIIa), (IIIb), (IIIc), or (IIId),

(IIIa)

(IIIb)

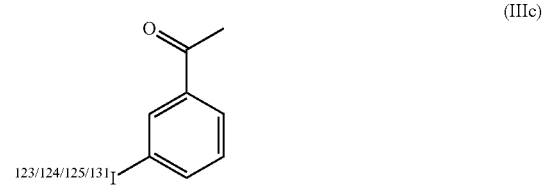
(IIIc)

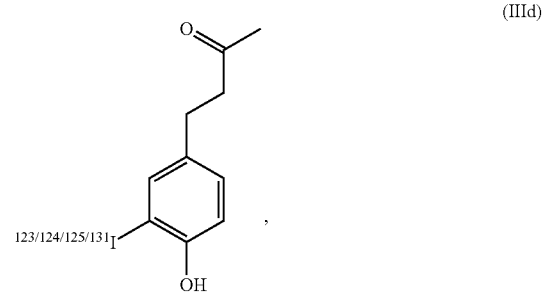
(IIId)

wherein $R^1$ represents a substituent selected from the group consisting of isotopes of radionuclides, isotopes of radionuclide-substituted $C_1$-$C_3$ alkyl groups, and isotopes of radionuclide-substituted $C_1$-$C_3$ alkoxy groups.

* * * * *